(12) United States Patent
Thornton et al.

(10) Patent No.: US 10,596,027 B2
(45) Date of Patent: *Mar. 24, 2020

(54) APPARATUS FOR IMPROVED BREATHING

(71) Applicant: AirWay Technologies, LLC, Carrollton, TX (US)

(72) Inventors: W. Keith Thornton, Dallas, TX (US); Alastair Edwin McAuley, Warkworth (NZ)

(73) Assignee: AirWay Technologies, LLC, Carrollton, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/224,112

(22) Filed: Jul. 29, 2016

(65) Prior Publication Data

US 2016/0331577 A1 Nov. 17, 2016

Related U.S. Application Data

(63) Continuation of application No. 14/009,821, filed as application No. PCT/US2012/032407 on Apr. 5, (Continued)

(51) Int. Cl.
*A61F 5/56* (2006.01)
*A61M 16/06* (2006.01)
(Continued)

(52) U.S. Cl.
CPC ......... *A61F 5/566* (2013.01); *A61M 16/0057* (2013.01); *A61M 16/0488* (2013.01);
(Continued)

(58) Field of Classification Search
CPC ........ A61F 5/566; A61F 5/56–58; A61C 7/08; A61C 19/03; A61C 7/10; A61C 7/36;
(Continued)

(56) References Cited

U.S. PATENT DOCUMENTS 690,663 A 1/1902 Pratt
746,869 A 12/1903 Moulton
(Continued)

FOREIGN PATENT DOCUMENTS

CN 101553194 10/2009
DE 156627 12/1904
(Continued)

OTHER PUBLICATIONS

Sekisui, Volara Grades Technical Data Sheets, 2017, https://www.sekisuivoltek.com/products/volara-polyolefin-foams/ (Year: 2017).*
(Continued)

*Primary Examiner* — Alireza Nia
*Assistant Examiner* — Michelle J Lee
(74) *Attorney, Agent, or Firm* — Baker Botts L.L.P.

(57) ABSTRACT

According to one embodiment, an apparatus for improved breathing is provided. The apparatus may include an improved oral appliance, an improved mask, an improved coupler to couple an oral appliance to a mask, and/or a combination of these improvements.

26 Claims, 27 Drawing Sheets

Related U.S. Application Data 2012, which is a continuation of application No. 13/080,050, filed on Apr. 5, 2011, now Pat. No. 8,671,946, and a continuation of application No. 13/080,103, filed on Apr. 5, 2011, now Pat. No. 8,783,261, and a continuation of application No. 13/080,167, filed on Apr. 5, 2011, now Pat. No. 8,662,084.

(51) Int. Cl.
| | | |
|---|---|---|
| *B29C 65/56* | (2006.01) | |
| *B29B 13/08* | (2006.01) | |
| *B29B 13/02* | (2006.01) | |
| *A61M 16/04* | (2006.01) | |
| *A61M 16/00* | (2006.01) | |
| *B29L 31/00* | (2006.01) | |
| *B29K 667/00* | (2006.01) | |

(52) U.S. Cl.
CPC .... *A61M 16/0605* (2014.02); *A61M 16/0666* (2013.01); *A61M 16/0683* (2013.01); *B29B 13/02* (2013.01); *B29B 13/08* (2013.01); *B29C 65/562* (2013.01); *B29K 2667/00* (2013.01); *B29L 2031/753* (2013.01)

(58) Field of Classification Search
CPC ...... A61C 9/00–0013; A61C 19/06–08; A61C 13/0025; A61C 2201/00; A61C 2201/007; A63B 71/085; A63B 2071/086; A63B 2071/088; A63B 71/081; A63B 71/08–085; A61M 16/0488–0497
See application file for complete search history.

(56) References Cited

U.S. PATENT DOCUMENTS

| | | |
|---|---|---|
| 774,446 A | 11/1904 | Moulton |
| 781,516 A | 1/1905 | Guthrie, Jr. |
| 885,196 A | 4/1908 | Steil |
| 893,213 A | 7/1908 | Whiteway |
| 911,476 A | 2/1909 | Cheesman |
| 955,562 A | 4/1910 | Thomas |
| 996,783 A | 7/1911 | Moreau |
| 1,076,534 A | 10/1913 | Wallen |
| 1,077,272 A | 11/1913 | Graybill |
| 1,146,264 A | 7/1915 | Kelly |
| 1,483,694 A | 2/1924 | Stukey |
| 1,592,345 A | 7/1926 | Drager |
| 1,649,664 A | 11/1927 | Carter |
| 1,674,336 A | 6/1928 | King |
| 1,675,202 A | 6/1928 | Warne |
| 1,679,748 A | 8/1928 | Stratton |
| 2,171,695 A | 9/1939 | Harper |
| 2,178,128 A | 10/1939 | Waite |
| 2,383,649 A | 8/1945 | Heidbrink |
| 2,387,522 A | 10/1945 | Maurer |
| 2,424,533 A | 7/1947 | Faires |
| 2,505,028 A | 4/1950 | Boeger |
| 2,521,039 A | 9/1950 | Carpenter |
| 2,521,084 A | 9/1950 | Oberto |
| 2,531,222 A | 11/1950 | Kesling |
| 2,574,623 A | 11/1951 | Clyde |
| 2,590,118 A | 3/1952 | Oddo, Jr. |
| 2,627,268 A | 2/1953 | Leppich |
| 2,671,446 A | 3/1954 | Mann |
| 2,833,278 A | 5/1958 | Ross |
| 2,867,212 A | 1/1959 | Nunn, Jr. |
| 2,882,893 A | 4/1959 | Godfroy |
| 2,917,045 A | 12/1959 | Schildknecht |
| 2,922,418 A | 1/1960 | Heffernan |
| 2,977,636 A | 4/1961 | McGuire |
| 3,037,501 A | 6/1962 | Miller |
| 3,064,354 A | 11/1962 | Pos |
| 3,107,668 A | 10/1963 | Thompson |
| 3,124,129 A | 3/1964 | Grossberg |
| 3,132,647 A | 5/1964 | Corniello |
| 3,219,033 A | 11/1965 | Wallshein |
| 3,277,892 A | 10/1966 | Tepper |
| 3,312,216 A | 4/1967 | Wallshein |
| 3,321,832 A | 5/1967 | Weisberg |
| 3,330,274 A | 7/1967 | Bennett |
| 3,360,860 A | 1/1968 | Roland |
| 3,434,470 A | 3/1969 | Strickland |
| 3,457,916 A | 7/1969 | Wolicki |
| 3,513,838 A | 5/1970 | Foderick |
| 3,522,805 A | 8/1970 | Wallshein |
| 3,658,058 A | 4/1972 | Neidhart |
| 3,690,004 A | 9/1972 | Frush |
| 3,695,265 A | 10/1972 | Brevik |
| 3,845,768 A | 11/1974 | Garrahan |
| 3,854,208 A | 12/1974 | Arant |
| 3,864,832 A | 2/1975 | Carlson |
| 3,871,370 A | 3/1975 | McDonald |
| 3,882,601 A | 5/1975 | Jahn |
| 3,884,226 A | 5/1975 | Tepper |
| 4,016,650 A | 4/1977 | Leusner |
| 4,026,024 A | 5/1977 | Tradowsky |
| 4,050,457 A | 9/1977 | Davidson |
| 4,114,614 A | 9/1978 | Kesling |
| 4,169,473 A | 10/1979 | Samelson |
| 4,182,312 A | 1/1980 | Mushabac |
| 4,227,877 A | 10/1980 | Tureaud |
| 4,233,972 A | 11/1980 | Hauff |
| 4,240,415 A * | 12/1980 | Wartman ............... A61L 15/12 528/359 |
| 4,258,710 A | 3/1981 | Reber |
| 4,289,127 A | 9/1981 | Nelson |
| 4,294,243 A | 10/1981 | Ernsting |
| 4,304,227 A | 12/1981 | Samelson |
| 4,345,592 A | 8/1982 | Giorgini |
| 4,345,593 A | 8/1982 | Sullivan |
| 4,376,628 A | 3/1983 | Aardse |
| 4,382,783 A | 5/1983 | Rosenberg |
| 4,392,490 A | 7/1983 | Mattingly |
| 4,397,701 A | 8/1983 | Johnson |
| 4,419,992 A | 12/1983 | Chorbajian |
| 4,433,956 A | 2/1984 | Witzig |
| 4,439,147 A | 3/1984 | Magill |
| 4,439,149 A | 3/1984 | Devincenzo |
| 4,454,090 A | 6/1984 | Saumell |
| 4,470,413 A | 9/1984 | Warncke |
| 4,495,945 A | 1/1985 | Liegner |
| 4,505,672 A | 3/1985 | Kurz |
| 4,530,662 A | 7/1985 | Andersson |
| 4,553,549 A | 11/1985 | Pope |
| 4,568,280 A | 2/1986 | Ahlin |
| 4,569,342 A | 2/1986 | von Nostitz |
| 4,593,686 A | 6/1986 | Lloyd |
| 4,602,905 A | 7/1986 | O'Keefe, III |
| 4,639,220 A | 1/1987 | Nara |
| 4,655,213 A | 4/1987 | Rapoport |
| 4,668,188 A | 5/1987 | Wolfenson |
| 4,669,459 A | 6/1987 | Spiewak |
| 4,676,240 A | 6/1987 | Gardy |
| 4,706,683 A | 11/1987 | Chilton |
| 4,715,368 A | 12/1987 | George |
| 4,725,323 A * | 2/1988 | Ostreicher ............ B01D 29/111 156/303.1 |
| 4,741,696 A | 5/1988 | Cetlin |
| 4,773,853 A | 9/1988 | Kussick |
| 4,784,123 A | 11/1988 | Robeson |
| 4,796,621 A | 1/1989 | Barle |
| 4,799,500 A | 1/1989 | Newbury |
| 4,858,605 A | 8/1989 | Levy |
| 4,858,606 A | 8/1989 | Hamlin |
| 4,862,903 A | 9/1989 | Campbell |
| 4,870,962 A | 10/1989 | Sitnik |
| 4,886,056 A | 12/1989 | Simpson |
| 4,892,478 A | 1/1990 | Tateosian |
| 4,901,737 A | 2/1990 | Toone |
| 4,906,234 A | 3/1990 | Voychehovski |
| 4,919,128 A | 4/1990 | Kopala |

(56) References Cited

U.S. PATENT DOCUMENTS

| | | |
|---|---|---|
| 4,932,867 A | 6/1990 | Ueno |
| 4,941,212 A | 7/1990 | Liff |
| 4,955,393 A | 9/1990 | Adell |
| RE33,442 E | 11/1990 | George |
| 5,003,994 A | 4/1991 | Cook |
| 5,011,407 A | 4/1991 | Pelerin |
| 5,018,533 A | 5/1991 | Hawkins |
| 5,026,278 A | 6/1991 | Oxman |
| 5,028,232 A | 7/1991 | Snow |
| 5,040,976 A | 8/1991 | Ubel, III |
| 5,042,478 A | 8/1991 | Kopala |
| 5,042,506 A | 8/1991 | Liberati |
| 5,046,512 A | 9/1991 | Murchie |
| 5,052,409 A | 10/1991 | Tepper |
| 5,055,039 A | 10/1991 | Abbatte |
| 5,056,534 A | 10/1991 | Wright |
| 5,062,421 A | 11/1991 | Burns |
| 5,064,371 A | 11/1991 | Smeltzer |
| 5,065,756 A | 11/1991 | Rapoport |
| 5,066,231 A | 11/1991 | Oxman |
| 5,078,600 A | 1/1992 | Austin |
| 5,092,346 A | 3/1992 | Hays |
| 5,103,838 A | 4/1992 | Yousif |
| 5,112,225 A | 5/1992 | Diesso |
| 5,117,816 A | 6/1992 | Shapiro |
| 5,154,184 A | 10/1992 | Alvarez |
| 5,154,609 A | 10/1992 | George |
| 5,183,057 A | 2/1993 | Syrop |
| 5,188,529 A | 2/1993 | Lüth |
| 5,190,457 A | 3/1993 | Schreinemakers |
| 5,193,532 A | 3/1993 | Moa |
| 5,213,498 A | 5/1993 | Pelerin |
| 5,233,978 A | 8/1993 | Callaway |
| 5,243,971 A | 9/1993 | Sullivan |
| 5,245,995 A | 9/1993 | Sullivan |
| 5,265,595 A | 11/1993 | Rudolph |
| 5,267,557 A | 12/1993 | Her-Mou |
| 5,267,862 A | 12/1993 | Parker |
| 5,277,202 A | 1/1994 | Hays |
| 5,284,161 A | 2/1994 | Karell |
| 5,313,960 A | 5/1994 | Tomasi |
| 5,316,020 A | 5/1994 | Truffer |
| 5,320,533 A | 6/1994 | Lee |
| 5,336,086 A | 8/1994 | Simmen |
| 5,365,945 A | 11/1994 | Halstrom |
| 5,370,533 A | 12/1994 | Bushnell |
| 5,373,859 A | 12/1994 | Forney |
| 5,392,773 A | 2/1995 | Bertrand |
| 5,409,017 A | 4/1995 | Lowe |
| 5,415,544 A | 5/1995 | Oxman |
| 5,427,117 A | 6/1995 | Thornton |
| 5,456,264 A | 10/1995 | Series |
| 5,458,137 A | 10/1995 | Axe |
| 5,474,060 A | 12/1995 | Evans |
| 5,477,850 A | 12/1995 | Zegler |
| 5,499,633 A | 3/1996 | Fenton |
| 5,503,146 A | 4/1996 | Froehlich |
| 5,503,552 A | 4/1996 | Diesso |
| 5,517,983 A | 5/1996 | Deighan |
| 5,537,994 A | 7/1996 | Thornton |
| 5,537,999 A | 7/1996 | Dearman |
| 5,538,000 A | 7/1996 | Rudolph |
| 5,538,014 A | 7/1996 | Wilson |
| 5,540,223 A | 7/1996 | Starr |
| 5,551,419 A | 9/1996 | Froehlich |
| 5,551,872 A | 9/1996 | Mena |
| 5,554,024 A * | 9/1996 | Ueda .................... A61C 9/0006 433/37 |
| 5,558,090 A | 9/1996 | James |
| RE35,339 E | 10/1996 | Rapoport |
| 5,560,354 A | 10/1996 | Berthon-Jones |
| 5,562,449 A | 10/1996 | Jacobs |
| 5,566,683 A | 10/1996 | Thornton |
| 5,570,704 A | 11/1996 | Buzzard |
| 5,582,517 A | 12/1996 | Adell |
| 5,592,935 A | 1/1997 | Elstran |
| 5,611,485 A | 3/1997 | Davis |
| 5,657,751 A | 8/1997 | Karr, Jr. |
| 5,657,752 A | 8/1997 | Landis |
| 5,662,101 A | 9/1997 | Ogden |
| 5,676,133 A | 10/1997 | Hickle |
| 5,678,567 A | 10/1997 | Thornton |
| 5,681,164 A | 10/1997 | Bass |
| 5,687,715 A | 11/1997 | Landis |
| 5,709,548 A * | 1/1998 | Oxman ................ A61C 9/0006 433/218 |
| 5,713,349 A | 2/1998 | Keaney |
| 5,718,244 A | 2/1998 | Thornton |
| 5,718,500 A | 2/1998 | Vinci guera |
| 5,720,280 A | 2/1998 | Elstran |
| 5,720,302 A | 2/1998 | Belfer |
| 5,724,965 A | 3/1998 | Handke |
| 5,746,201 A | 5/1998 | Kidd |
| 5,752,510 A | 5/1998 | Goldstein |
| 5,755,219 A | 5/1998 | Thornton |
| 5,807,100 A | 9/1998 | Thornton |
| 5,810,749 A | 9/1998 | Maas |
| 5,829,441 A | 11/1998 | Kidd |
| 5,832,918 A | 11/1998 | Pantino |
| 5,846,082 A | 12/1998 | Thornton |
| 5,887,587 A | 3/1999 | Groenke |
| 5,891,372 A | 4/1999 | Besset |
| 5,954,048 A | 9/1999 | Thornton |
| 5,983,892 A | 11/1999 | Thornton |
| 5,988,166 A | 11/1999 | Hayek |
| 6,012,455 A | 1/2000 | Goldstein |
| 6,012,919 A | 1/2000 | Cross, III |
| 6,044,844 A | 4/2000 | Kwok |
| 6,083,442 A | 7/2000 | Gabilly |
| 6,109,265 A | 8/2000 | Frantz |
| 6,119,694 A | 9/2000 | Correa |
| 6,123,071 A | 9/2000 | Berthon-Jones |
| 6,155,262 A | 12/2000 | Thornton |
| 6,209,542 B1 | 4/2001 | Thornton |
| 6,247,926 B1 | 6/2001 | Thornton |
| 6,263,871 B1 | 7/2001 | Brown |
| D448,473 S | 9/2001 | Barnett |
| 6,305,376 B1 | 10/2001 | Thornton |
| 6,318,997 B1 | 11/2001 | Mayweather |
| 6,325,064 B1 | 12/2001 | Thornton |
| 6,374,824 B1 | 4/2002 | Thornton |
| 6,405,729 B1 | 6/2002 | Thornton |
| 6,412,488 B1 | 7/2002 | Barnett |
| 6,450,167 B1 | 9/2002 | David |
| 6,464,924 B1 | 10/2002 | Thornton |
| 6,494,206 B1 | 12/2002 | Bergamaschi |
| 6,516,805 B1 | 2/2003 | Thornton |
| 6,520,177 B1 | 2/2003 | Bonhomme |
| 6,536,439 B1 | 3/2003 | Palmisano |
| 6,571,798 B1 | 6/2003 | Thornton |
| 6,604,527 B1 | 8/2003 | Palmisano |
| 6,645,413 B2 | 11/2003 | Jacobs |
| 6,675,802 B1 | 1/2004 | Thornton |
| 6,758,212 B2 | 7/2004 | Swann |
| 6,769,910 B1 | 8/2004 | Pantino |
| 6,845,774 B2 | 1/2005 | Gaskell |
| 6,857,428 B2 | 2/2005 | Thornton |
| 6,877,513 B2 | 4/2005 | Scarberry |
| 7,036,508 B2 | 5/2006 | Kwok |
| 7,077,138 B2 | 7/2006 | Bateman |
| 7,174,895 B2 | 2/2007 | Thornton |
| 7,255,811 B2 | 8/2007 | Hirschmann |
| 7,520,281 B1 | 4/2009 | Nahabedian |
| 7,597,103 B2 | 10/2009 | Thornton |
| 7,650,885 B2 | 1/2010 | Paoluccio |
| 7,677,889 B2 | 3/2010 | Thornton |
| 7,721,741 B2 | 5/2010 | Thornton |
| 7,748,386 B2 | 7/2010 | Thornton |
| 7,823,590 B2 | 11/2010 | Bibi |
| 7,832,403 B2 | 11/2010 | Halstrom |
| 7,909,035 B2 | 3/2011 | Thornton |
| 7,992,558 B2 | 8/2011 | Thornton |
| 8,020,276 B2 | 9/2011 | Thornton |
| 2002/0000230 A1 | 1/2002 | Gaskell |

(56) References Cited

U.S. PATENT DOCUMENTS

| | | | |
|---|---|---|---|
| 2002/0129818 A1 | 9/2002 | Morgan | |
| 2002/0139366 A1 | 10/2002 | Gaschke | |
| 2003/0217753 A1 | 11/2003 | Thornton | |
| 2003/0234022 A1 | 12/2003 | Belfer | |
| 2004/0079374 A1 | 4/2004 | Thornton | |
| 2004/0226563 A1 | 11/2004 | Xu | |
| 2004/0237965 A1 | 12/2004 | Bibi | |
| 2005/0016544 A1 | 1/2005 | Thornton | |
| 2005/0028827 A1 | 2/2005 | Halstron | |
| 2005/0034733 A1 | 2/2005 | Liddle | |
| 2005/0061324 A1 | 3/2005 | Tadros | |
| 2005/0268914 A1 | 12/2005 | Paoluccio | |
| 2006/0005837 A1 | 1/2006 | Thornton | |
| 2006/0084024 A1* | 4/2006 | Farrell | A61C 7/08 433/6 |
| 2006/0124131 A1 | 6/2006 | Chandran | |
| 2006/0154195 A1* | 7/2006 | Mather | A61C 7/00 433/6 |
| 2007/0006879 A1 | 1/2007 | Thornton | |
| 2007/0074729 A1 | 4/2007 | Magnin | |
| 2007/0079835 A1* | 4/2007 | Croll | A63B 71/085 128/859 |
| 2007/0125388 A1 | 6/2007 | Thornton | |
| 2007/0163594 A1 | 7/2007 | Ho | |
| 2007/0235037 A1 | 10/2007 | Thornton | |
| 2007/0292819 A1* | 12/2007 | Scarberry | A61F 5/566 433/140 |
| 2008/0006273 A1 | 1/2008 | Thornton | |
| 2008/0006274 A1 | 1/2008 | Thornton | |
| 2008/0032256 A1 | 2/2008 | Thornton | |
| 2008/0041390 A1 | 2/2008 | Radney | |
| 2008/0060648 A1 | 3/2008 | Thornton | |
| 2008/0127984 A1 | 6/2008 | Thornton | |
| 2008/0295850 A1 | 12/2008 | Lesniak | |
| 2009/0014013 A1* | 1/2009 | Magnin | A61F 5/566 128/848 |
| 2009/0130624 A1 | 5/2009 | Sun | |
| 2010/0065067 A1 | 3/2010 | Lee | |
| 2010/0154802 A1 | 6/2010 | Fuselier | |
| 2010/0261133 A1 | 10/2010 | Lax | |
| 2010/0263676 A1 | 10/2010 | Thornton | |
| 2011/0168187 A1 | 7/2011 | Nelissen | |

FOREIGN PATENT DOCUMENTS

| | | |
|---|---|---|
| DE | 2 320 501 | 11/1974 |
| DE | 35 43 931 A1 | 6/1987 |
| DE | 37 07 952 A1 | 9/1988 |
| DE | 37 19 009 A1 | 12/1988 |
| DE | 2950651.2 | 7/1995 |
| DE | 44 38 512 A1 | 5/1996 |
| DE | 198 46 686 A1 | 7/1999 |
| EP | 0 312 368 A1 | 4/1989 |
| EP | 0 359 135 A1 | 3/1990 |
| FR | 2 658 725 A1 | 8/1991 |
| FR | 2731624 | 9/1996 |
| GB | 1 569 129 | 6/1980 |
| GB | 2 072 567 A | 10/1981 |
| WO | WO 91/12777 | 9/1991 |
| WO | WO 97/25010 | 7/1997 |
| WO | WO 98/20924 | 5/1998 |
| WO | WO 98/26736 | 6/1998 |
| WO | WO 98/46177 | 10/1998 |
| WO | WO 2000/015283 | 3/2000 |
| WO | WO 2006/108209 | 10/2004 |
| WO | WO 2007/146523 | 6/2006 |

OTHER PUBLICATIONS

Official Action; dated Sep. 24, 2015; Application No. 12 714 192.7.
2nd Office Action, Chinese Patent Office; App. No. 201280027519.8; 17 pages including English translation, dated Jun. 30, 2015.
Communication pursuant to Article 94(3) EPC; Application No. 13 005 701.1-1654; 4 pages, dated Jul. 31, 2015.
Australian Office Action; Pat. App. No. 2012240097; W. Keith Thornton; 5 pages, dated Nov. 13, 2015.
"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.
CPAP-PRO—Introducing a New Comfort Level for CPAP Users brochure, 2 pages, Not Dated.
PCT, Notification of Transmittal of the International Search Report and the Written Opinion of the International Searching Authority, or the Declaration, PCT/US06/26622, 11 pages, dated Feb. 21, 2007.
European Patent Office Communication, Application No. 03 809 555.0-1257, Applicant: W. Keith Thornton, 4 pages, dated Aug. 7, 2009.
Canadian Intellectual Property Office, Application No. 2,502,280, Applicant: W. Keith Thornton, 3 pages, dated Feb. 23, 2010.
Personally Moulded Sleep Apnea Masks, http://;web.archive.org/web/20030618145716/www.sleepapneamasks.com.au/default.asp, downloaded Aug. 17, 2009 (2 pgs)).
Acurest, The Logic Sleep Mask http://sleepapneamasks.com.au/, 2002.
Whitestone et al., Fabrication of Total Contract Burn Masks Using Non-Contact Surface Scanning: A New Standard of Care, 1997, pp. 1-8, dated 1997.
PCT, Notification of Transmittal of the International Search Report and the Written Opinion of the International Searching Authority, or the Declaration, International Application No. PCT/US2011/039231, filed Jun. 6, 2011 (11 pgs), dated Sep. 12, 2011.
Japanese Patent Office, Action re patent application 2004/500750, dated Oct. 14, 2008.
Australian Office Action re patent application No. 2007/243957 dated Mar. 9, 2012.
PCT Notification of Transmittal of the International Search Report and the Written Opinion of the International Searching Authority, or the Declaration; dated Jul. 13, 2012; International app No. PCT/US2012/032407; 18 pages.
European Search Report; dated Mar. 3, 2014; Application No. 13005701.1-1654/2705811.
IPO of the People's Republic of China, Chinese Office Action and Translation of Text of the First Office Action issued by State Intellectual Property Office, Application No. 20120027519.8; dated Dec. 1, 2014 (15 pages).
Mayo Clinic Health Letter; Reliable Information for a Healthier Life; Snoring: Laser Surgery Joins Battle to Restore Peace and Quiet; vol. 13, No. 7, 8 pages, dated Jul. 1995.
Photocopies of 2-piece dental device manufactured by Currie-Gibson Dental Lboratory, Inc., prior to Apr. 13, 1993, 5 pages, Prior to Apr. 13, 1993.
Farrar, et al, A Clinical Outline of Temporomandibular Joint Diagnosis and Treatment, Normandie Study Group for TMJ Dysfunction, 3 pages, dated 1983.
Professional Positioners; Dedicated to Excellence brochure, 3 pages, Unknown.
Great Lakes Orthodontics, Ltd.; Nocturnal Airway Patency Applicance; 2 pages, Not Dated.
Schmidt-Nowara, et al.; An American Sleep Disorders Association Review; Oral Appliances for the Treatment of Snoring and Obstructive Sleep Apnea: A Review; pp. 501-510, dated 1995.
George, Peter; Treatment of Snoring and Obstructive Sleep Apnea with a Dental Device; 5 pages, dated Jul.-Aug. 1993.
Database WOI, Section PQ, Week 9039, Derwent Publications, Ltd., London, GB; XP-002116355 Abstract—Surgical Mouth Air Duct; 1 page, dated Dec. 15, 1989.
PCT Notification of Transmittal of the International Search Report or the Declaration for International Application No. PCT/US97/08708, dated Aug. 12, 1997.
PCT Invitation to Pay Additional Fees for International Application No. PCT/US03/13705, dated Oct. 10, 2003.
PCT, Notification of Transmittal of the International Search Report and the Written Opinion of the International Searching Authority, or the Declaration, PCT/US07/02736, 10 pages, dated Oct. 26, 2007.

(56) References Cited

OTHER PUBLICATIONS

PCT, Notification of Transmittal of the International Search Report and the Written Opinion of the International Searching Authority, or the Declaration, PCT/US2010/051136, 10 pages, dated Mar. 4, 2011.
Craig, William H., et al.; "Skeletal class II treatment with the Chateau appliance," The Journal of Pedondontics (vol. 11:120); pp. 120-138, dated 1987.
Samuel T. Kuna, M.D., et al., "Effect of Progressive Mandibular Advancement on Pharyngeal Airway Size in Anesthetized Adults," National Institute of Health; NIH Public Access Author Manuscript; Published Oct. 2008; Anesthesiology; 109(4); 16 pages.
PCT, Notification of Transmittal of the International Search Report and the Written Opinion of the International Searching Authority, or the Declaration, PCT/US2012/032407, 18 pages, dated Jul. 13, 2012.
PCT Invitation to Pay Additional Fees for International Application No. PCT/US2012/028885; (0306 Foreign), dated May 30, 2012.
PCT Invitation to Pay Additional Fees for International Application No. PCT/US2012/032407; (0314 Foreign), dated May 30, 2012.
PCT, Notification of Transmittal of the International Search Report and the Written Opinion of the International Searching Authority, or the Declaration, PCT/ US2012/028885, 18 pages, dated Jul. 17, 2012.
Office Action; European Patent Office; Re: Appl. No. 12 714 192.7-1122; 3 pages, dated Sep. 12, 2018.
Office Action; Canadian Intellectual Property Office; Re: Appl. No. 2,832,533; 4 pages, dated Apr. 17, 2018.
Communication pursuant to Article 94(3) EPC; Appln No. 12 714 192.7-1122; 5 pages, dated Jul. 31, 2019.

* cited by examiner

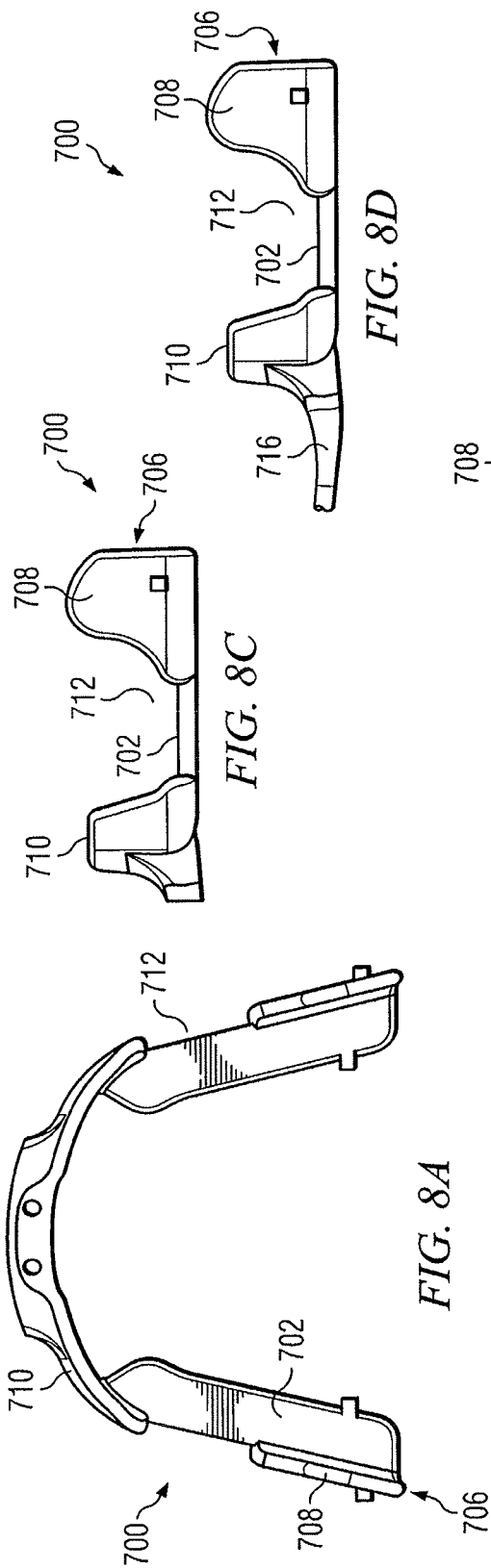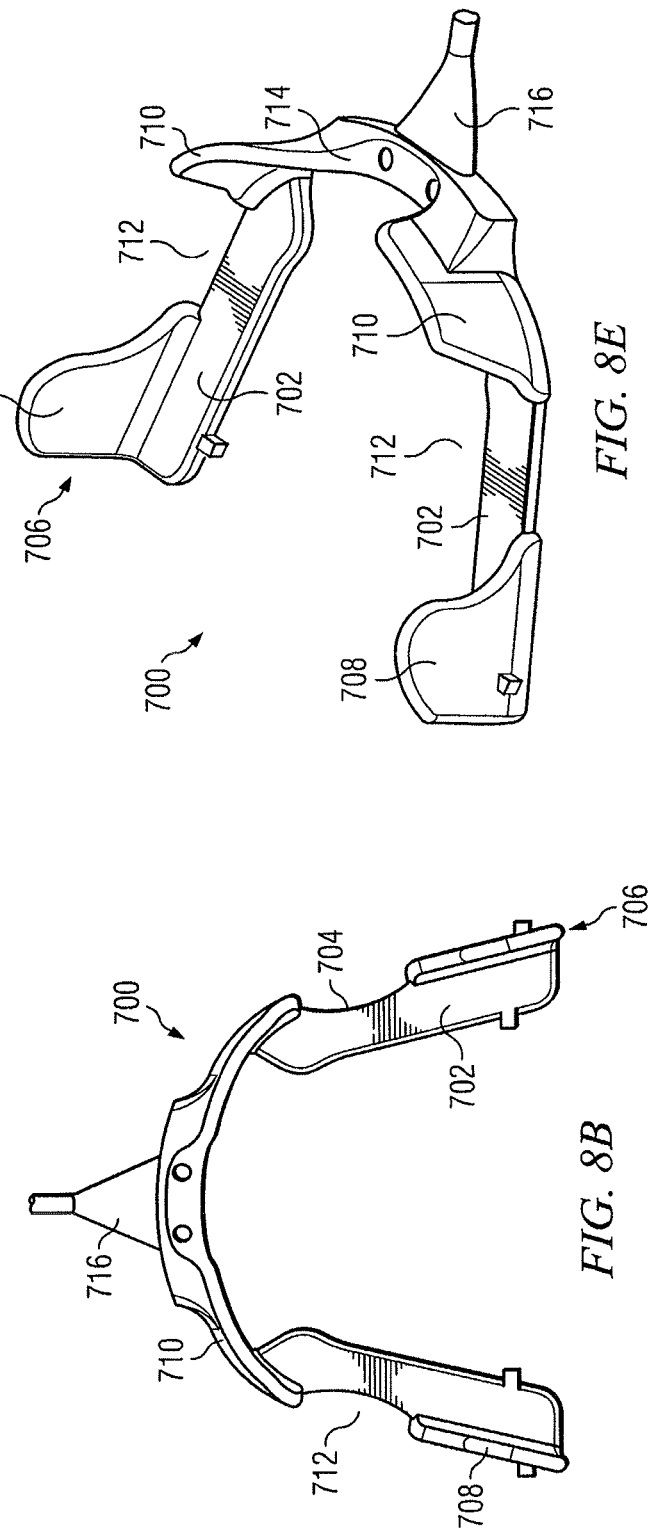

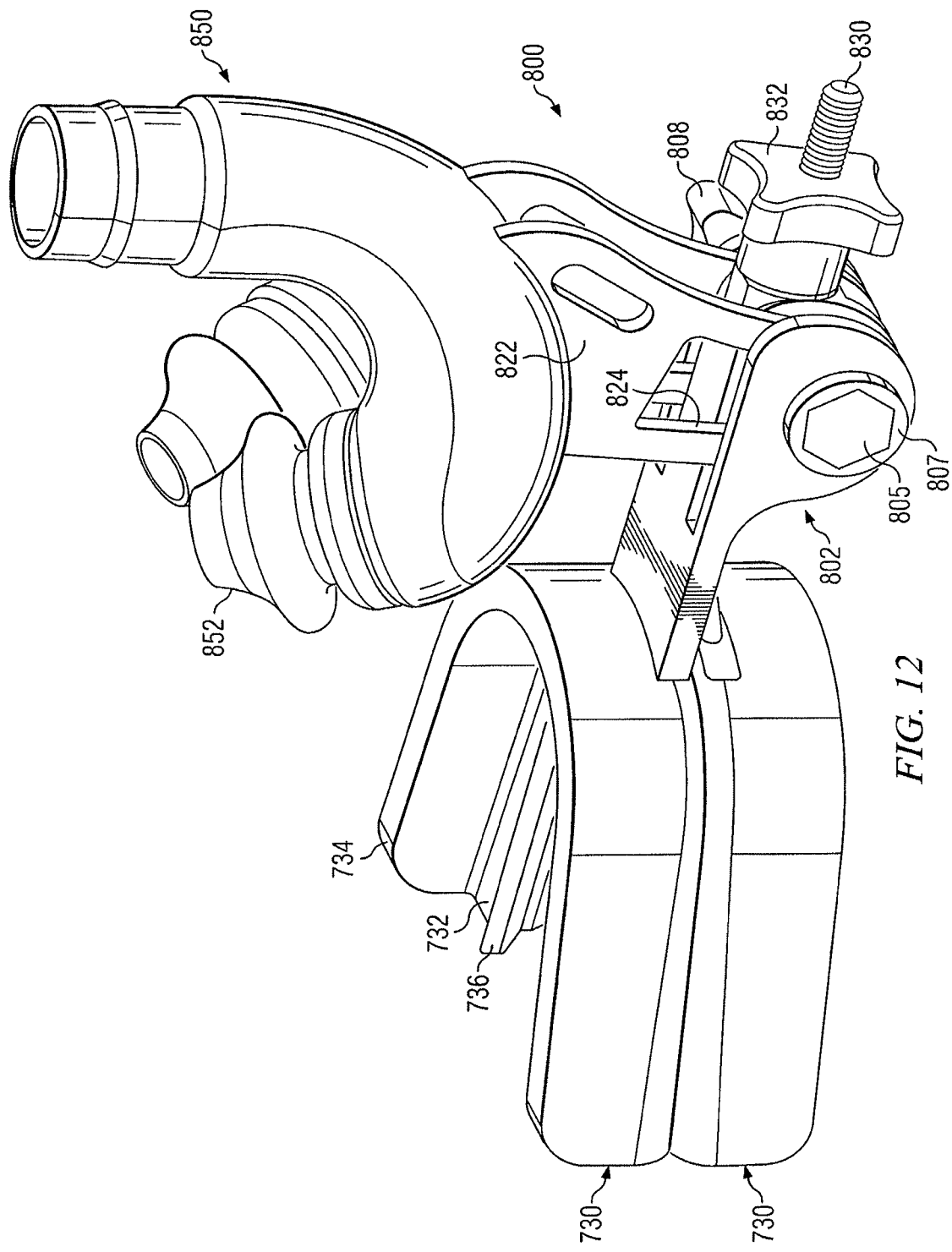

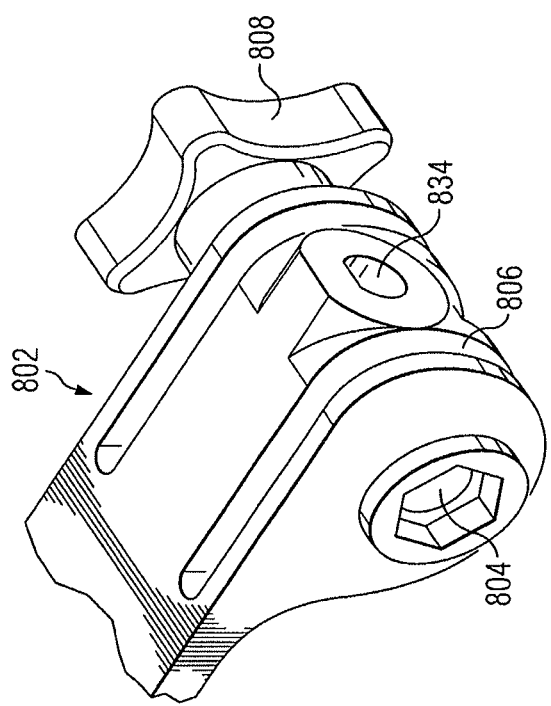
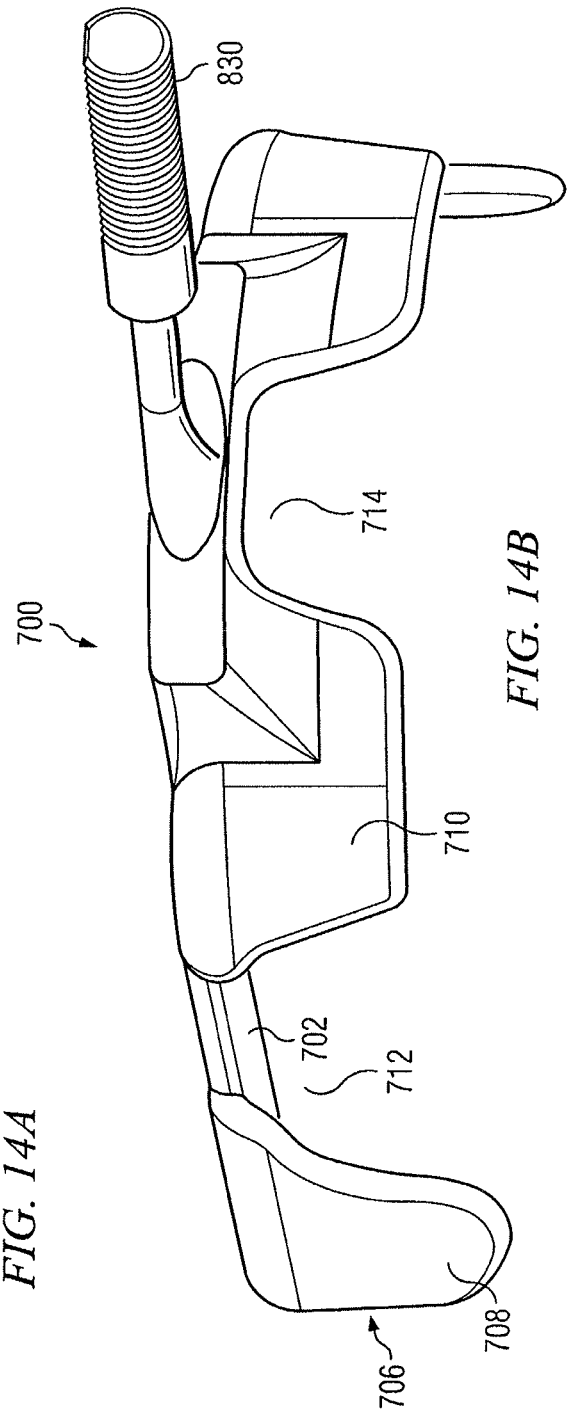
FIG. 14A
FIG. 14B

APPARATUS FOR IMPROVED BREATHING

RELATED APPLICATIONS AND CLAIM TO PRIORITY

This application is a continuation of U.S. Ser. No. 14/009,821, filed Nov. 1, 2013, which is a U.S. National Stage Filing under 35 U.S.C. § 371 of International Patent Application Serial No. PCT/US2012/032407, filed Apr. 5, 2012 and entitled "Apparatus for Improved Breathing," which is a continuation of U.S. application Ser. No. 13/080,167, filed Apr. 5, 2011 and entitled "Universal Oral Appliance with a Universal Coupler," U.S. application Ser. No. 13/080,050, filed Apr. 5, 2011 and entitled "Custom Dental Appliance and Method of Creating a Custom Dental Appliance," and U.S. application Ser. No. 13/080,103, filed Apr. 5, 2011 and entitled "Apparatus for Prevention of Snoring and Improved Breathing." This application claims priority to each of PCT/US2012/032407 and U.S. application Ser. Nos. 14/009,821, 13/080,167, 13/080,050, and 13/080,103.

TECHNICAL FIELD OF THE INVENTION

This invention relates generally to medical and dental devices; and more particularly to an apparatus for improving a user's breathing.

BACKGROUND

Many people experience difficulty in sleeping because of breathing problems. These problems may result in snoring, or the more serious condition of sleep apnea. One treatment for sleep breathing disorders involves the use of dental devices for extending forward the lower jaw of the patient. These devices operate to more fully open the breathing passageway, thereby allowing for easier breathing, whether that breathing be through the nose or through the mouth. Furthermore, many people suffer from degraded teeth or jaw pain arising from bruxing or the grinding of teeth during sleep. One treatment for grinding involves the use of dental devices that put pressure on a patient's front teeth to relax and unclench the patient's jaw.

These dental devices may be created in labs after a dentist sends in a patient's dental impressions. This procedure can cost the patient substantial time and money because the dentist creates a dental impression and then the lab creates the dental device after the dentist sends in the dental impression. Also, these lab-created dental devices are often designed to target particular problems. For example, a device for treating snoring may not help a patient who grinds his teeth.

People who suffer from sleep problems may seek help from a sleep laboratory. Doctors at the laboratory may perform tests on patients as they sleep. Doctors may further test the effectiveness of various dental devices on the patients as treatment options. During tests, doctors may need quick access inside a patient's mouth, and dental devices that hook or attach inside the patient's mouth may hinder the doctors' ability to gain quick access inside the mouth. This scenario may also occur during surgery when a patient is unconscious, and a dental device is inserted into the mouth to maintain the patient's airway.

Another treatment for sleep breathing disorders involves the use of masks to deliver air to users. These masks may also be used to deliver oxygen or other gases to a user. One difficulty with these masks is that they often move while the user is sleeping or they are uncomfortable to the user when worn.

SUMMARY OF THE INVENTION

In accordance with the teachings of the present invention, a dental device is provided which may reduce or eliminate disadvantages and problems associated with prior art devices.

In one embodiment, a dental device is provided comprising an arched frame and a moldable tray. The arched frame may be configured to be positioned proximate to the occlusal surface of a user's dental arch such that the arched frame extends beyond the cuspids of the user's dental arch. The arched frame may define a plurality of apertures and may comprise an adjustment mechanism. The moldable tray may be coupled to the arched frame and may engage the plurality of apertures. The moldable tray may comprise a channel configured to engage at least some of the teeth of the user's dental arch.

In a particular embodiment, a dental device is provided comprising an arched frame, a moldable tray, a second arched frame, and a second moldable tray. The arched frame may be configured to be positioned proximate to the occlusal surface of a user's maxillary arch such that the arched frame extends beyond the cuspids of the user's maxillary arch. The arched frame may define a plurality of apertures and may comprise an adjustment mechanism. The adjustment mechanism may comprise a hook and a threaded adjustor. The moldable tray may be coupled to the arched frame and may engage the plurality of apertures. The moldable tray may comprise a channel configured to engage at least some of the teeth of the user's maxillary arch. The second arched frame may be configured to be positioned proximate to the occlusal surface of a user's mandibular arch such that the second arched frame extends beyond the cuspids of the user's mandibular arch. The second arched frame may define a second plurality of apertures and may comprise a receiving mechanism coupled to the lingual portion of the lower arched body. The second moldable tray may be coupled to the second arched frame and may engage the plurality of apertures. The second moldable tray may comprise a second channel configured to engage at least some of the teeth of the user's mandibular arch. The hook may engage the receiving mechanism, and the threaded adjustor may adjust the forward position of the arched frame relative to the second arched frame.

In another embodiment, a dental device may include an arched frame configured to be positioned proximate to the occlusal surface of a user's dental arch such that the arched frame extends beyond the cuspids of the user's dental arch. The arched frame may define a plurality of apertures. The dental device may further include an adjustment mechanism coupled to the arched frame. The dental device may further include a moldable tray coupled to the arched frame. The moldable tray may engage the plurality of apertures and may comprise a channel configured to engage at least some of the teeth of the user's dental arch.

In another embodiment, a dental device may include an arched frame configured to be positioned proximate to the occlusal surface of a user's maxillary arch such that the arched frame extends beyond the cuspids of the user's maxillary arch. The arched frame may define a plurality of apertures. The dental device may further include an adjustment mechanism coupled to the arched frame. The adjustment mechanism may comprise a hook and a threaded adjustor. The dental device may further include a moldable tray coupled to the arched frame. The moldable tray may engage the plurality of apertures and may comprise a channel configured to engage at least some of the teeth of the user's maxillary arch. The dental device may further include a second arched frame configured to be positioned proximate to the occlusal surface of a user's mandibular arch such that the arched frame extends beyond the cuspids of the user's mandibular arch. The second arched frame may define a second plurality of apertures. The dental device may further include a receiving mechanism coupled to the lingual portion of the second arched frame and a second moldable tray coupled to the second arched frame. The second moldable tray may engage the second plurality of apertures and may comprise a second channel configured to engage at least some of the teeth of the user's mandibular arch. The hook may engage the receiving mechanism and the threaded adjustor may adjust the forward position of the arched frame relative to the second arched frame.

In another embodiment, a universal oral appliance is provided comprising an arched frame. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler configured to removably engage a dental attachment. The universal coupler may comprise a substantially planar surface proximate to and extending across the midline of the arched frame. The universal coupler may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot.

In another embodiment, a kit for use in constructing a universal oral appliance is provided. The kit may comprise an arched frame and a plurality of dental attachments. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler. The universal coupler may comprise a substantially planar surface proximate to and extending across the midline of the arched frame. The substantially planar surface may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot. The kit may further comprise a plurality of dental attachments comprising a rounded projection configured to be the point of contact between the user's upper and lower dental arches to prevent the user from clenching his jaw. The plurality of dental attachments may further comprise a hook configured to engage a receiving mechanism such that the forward position of a second arched frame may be adjusted relative to the position of the arched frame.

In another embodiment, a universal oral appliance is provided comprising an arched frame, a moldable tray, and a plurality of dental attachments. The arched frame may be configured to be positioned proximate to the occlusal surface of a user's dental arch such that the arched frame extends beyond the cuspids of the user's dental arch when the universal oral appliance is inserted in the user's mouth. The arched frame may have a midline that aligns substantially with the anterior midline of the user's mouth when the universal oral appliance is inserted in the user's mouth. The arched frame may define a plurality of apertures and may comprise a universal coupler. The universal coupler may comprise a substantially planar surface proximate to and extending across the midline of the arched frame. The substantially planar surface may be configured to be positioned proximate to the occlusal surface of a user's incisors when the universal oral appliance is inserted in the user's mouth. The universal coupler may further comprise a first rail coupled to a first end of the substantially planar surface and a second rail coupled to a second end of the substantially planar surface. The first rail, second rail, and substantially planar surface may define a slot. The moldable tray may be coupled to the arched frame and may comprise a channel configured to engage at least some of the teeth of the user's dental arch. The dental attachment may include a substantially rounded projection configured to be the point of contact between the user's upper and lower dental arches to prevent the user from clenching his jaw. The dental attachment may be an adjustable hook configured to engage the receiving mechanism such that the forward position of the arched frame is adjustable relative to the position of a second arched frame. The dental attachment may be a handle.

In another embodiment, a dental device is provided comprising an arch, a dental attachment with an anchoring element, a second arch with a second anchoring element, and a tension element. The arch may be configured to engage at least some of the teeth of a user's dental arch and may have a midline that aligns substantially with the anterior midline of the user's mouth when the arch is inserted in the user's mouth. The dental attachment may be configured to engage the arch along the midline of the arch. The dental attachment may comprise an anchoring element configured to be outside the user's mouth when the arch is inserted in the user's mouth. The second arch may be configured to engage at least some of the teeth of a user's second dental arch. The second arch may have a midline that aligns substantially with the anterior midline of the user's mouth when the second arch is inserted in the user's mouth. The second anchoring element may be coupled to the second arch along the midline of the second arch. The tension element may be configured to engage the second anchoring element. The tension element may be further configured to couple to the anchoring element outside the user's mouth when the arch is inserted in the user's mouth.

In another embodiment, a kit for constructing a dental device is provided. The kit may comprise an arch, a dental attachment with an anchoring element, a second arch with a second anchoring element, and a tension element. The arch may be configured to engage at least some of the teeth of a user's dental arch and may have a midline that aligns substantially with the anterior midline of the user's mouth when the arch is inserted in the user's mouth. The dental attachment may be configured to engage the arch along the midline of the arch. The dental attachment may comprise an anchoring element configured to be outside the user's mouth when the arch is inserted in the user's mouth. The second arch may be configured to engage at least some of the teeth of a user's second dental arch. The second arch may have a midline that aligns substantially with the anterior midline of the user's mouth when the second arch is inserted in the user's mouth. The second anchoring element may be coupled to the second arch along the midline of the second arch. The tension element may be configured to engage the second anchoring element. The tension element may be further configured to couple to the anchoring element outside the user's mouth when the second arch is inserted in the user's mouth.

In another embodiment, a dental device is provided comprising an arched frame, a moldable tray, a dental attachment with an anchoring element, a second arched frame with a second anchoring element, a second moldable tray, and a tension element. The arched frame may be configured to be positioned proximate to the occlusal surface of a user's maxillary arch such that the arched frame extends beyond the cuspids of the user's maxillary arch. The arched frame may define a plurality of apertures. The moldable tray may be coupled to the arched frame and may engage the plurality of apertures. The moldable tray may comprise a channel configured to engage at least some of the teeth of the user's maxillary arch. The dental attachment may be configured to removably engage the arch along the midline of the arch. The dental attachment may comprise an anchoring element configured to be outside the user's mouth when the arch is inserted in the user's mouth. The second arched frame may be configured to be positioned proximate to the occlusal surface of a user's mandibular arch such that the second arched frame extends beyond the cuspids of the user's mandibular arch. The second arched frame may define a second plurality of apertures. The second moldable tray may be coupled to the second arched frame and may engage the second plurality of apertures. The second moldable tray may comprise a channel configured to engage at least some of the teeth of the user's mandibular arch. The second anchoring element may be coupled to the second arch along the midline of the second arch. The tension element may be configured to removably engage the second anchoring element. The tension element may be configured to couple to the anchoring element outside the user's mouth when the second arch is inserted in the user's mouth. The dental attachment may comprise a post and a buckle coupled to a first end of the post. A second end of the post may engage the arch. The tension element may comprise a coupler and a strap coupled to the coupler. The coupler may engage the second anchoring element. A length of the strap may be configured to engage the buckle. The buckle may be configured to substantially secure the length of the strap engaging it. By increasing the length of the strap engaging the buckle, the forward position of the arched frame relative to the second arched frame may be adjusted.

In another embodiment, a coupler includes a support structure, at least one flange, and an elongated fastener. The support structure includes a first channel and a slot passing through the first channel and being substantially orthogonal to the first channel. The flange is partially within the first channel and the flange has a slot disposed through the flange. The elongated fastener is disposed within the slot of the support structure and passes through the slot of the flange to engage the flange, such that the flange is adjustably positioned within the first channel. The coupler is attached to an oral appliance having an occlusal surface and to a mask configured to deliver gas to a user, such that the orientation of the mask to the oral appliance is adjustable by rotating the flange about the fastener and adjustable in a direction substantially orthogonal to the occlusal surface of the oral appliance.

In another embodiment, an apparatus for use in forming a dental device includes a substantially rigid arched frame configured to be positioned proximate to the occlusal surface of a user's dental arch, such that the arched frame extends beyond the cuspids of the user's dental arch. The arched frame includes a first occlusal surface, a second occlusal surface, and a flange. The first occlusal surface is configured to be positioned proximate to the occlusal surface of the user's left molars. The second occlusal surface is configured to be positioned proximate to the occlusal surface of the user's right molars. The second occlusal surface is separated from the first occlusal surface. The flange connects the first and second occlusal surfaces, the flange extends in a direction substantially orthogonal to the first and second occlusal surfaces, and the flange is configured to be positioned labial to the user's dental arch.

In another embodiment, a dental device includes a substantially rigid arched frame and a thermoplastic material. The substantially rigid arched frame is configured to be positioned proximate to the occlusal surface of a user's dental arch, such that the arched frame extends beyond the cuspids of the user's dental arch. The arched frame includes an occlusal surface configured to be positioned proximate to the occlusal surface of the user's dentition. The thermoplastic material encloses at least a portion of the arched frame, such that occlusal surface of the arched frame is substantially enclosed by the thermoplastic material.

In another embodiment, an improved breathing device includes a mask, an oral appliance, and a tension element. The mask includes an opening configured to be positioned in front of the user's mouth when the mask is positioned on the user's face. The mask further includes a coupling element proximate to the opening. The oral appliance includes a maxillary arch with an anchor point proximate to the midline of the maxillary arch. The tension element is configured to couple to the a dental device at the anchor point and to couple to the mask at the coupling element. In certain embodiments, the tension element may be adjusted to pull the mask towards the oral appliance. In a particular embodiment, the coupling element is a strap that extends across a portion of the opening and includes one or more apertures through which the tension element may extend, the tension element includes a hook and a threaded knob, and the anchor point includes a loop, such that the mask is pulled toward the oral appliance as the threaded knob is turned while hook is coupled to the loop and extends through an aperture in the strap.

Previous dental devices may be constructed in labs independent of a dentist's office. Labs could not construct custom dental devices for particular patients without first having the patients' dental impressions. Labs may also charge patients an extra fee for constructing the dental devices. In particular embodiments, the dental device may be constructed at the dentist's office without sending dental impressions to a lab, thus saving patients time and money. Furthermore, previous dental devices may be created to treat only one disorder (such as, for example, snoring or jaw-clenching). In particular embodiments, the dental device may be customized to treat multiple dental problems. As an example, and not by way of limitation, the dental device may comprise a universal coupler configured to engage various dental attachments. Each dental attachment may be designed to treat a different disorder. Additionally, previous dental devices may limit the lower jaw's range of motion when the dental devices were inserted in the user's mouth. Previous dental devices may also limit a third party's access to the user's mouth when the dental device is in the user's mouth. In particular embodiments, the dental device may comprise a tension element engaging an anchoring element outside the user's mouth. The tension element and anchoring element may pull the user's lower jaw forward without locking the user's lower jaw in place. Furthermore, a third party may pull on the tension element to open the user's airway, or a third party may release the tension element from the anchoring element to quickly gain access to a user's mouth. Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

FIGS. 8A through 8E illustrate an example arched frame.
FIG. 12 illustrates example moldable trays, an example post, and an example mask.
FIG. 14A illustrates an example post.
FIG. 14B illustrates an example arched frame and tension element.

DETAILED DESCRIPTION OF THE INVENTION

Figure 1:
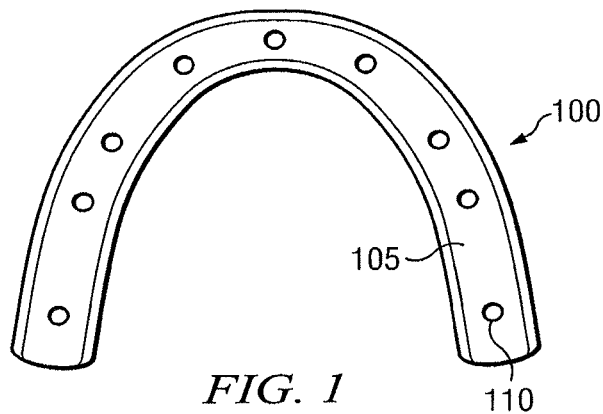
FIG. 1 illustrates an example arched frame.
Figure 2A:
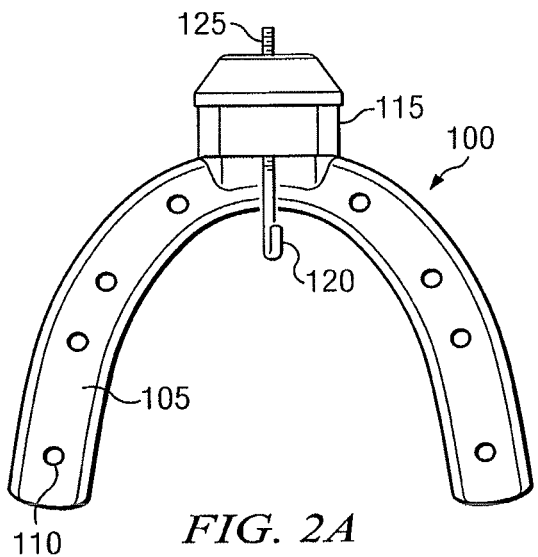
FIG. 2A illustrates an example arched frame comprising an adjustment mechanism.
Figure 2B:
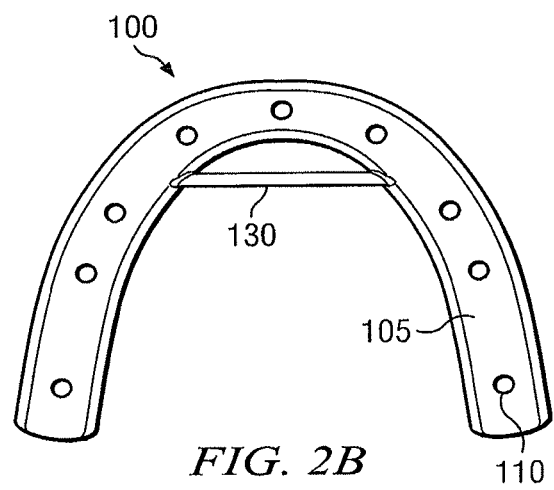
FIG. 2B illustrates an example arched frame comprising a receiving mechanism.
Figure 2C:
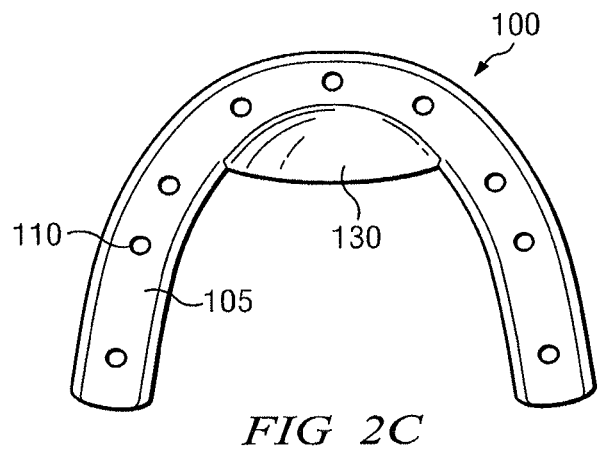
FIG. 2C illustrates an example arched frame comprising a receiving mechanism.

FIG. 1 illustrates an example arched frame 100. Arched frame 100 may comprise an arched body 105 that defines a plurality of apertures 110 through arched frame 100. In particular embodiments, arched frame 100 may be configured to be positioned proximate to the occlusal surface of a user's dental arch. In some embodiments, arched frame 100 may extend beyond the cuspids of the user's dental arch when arched frame 100 is inserted in the user's mouth. In some embodiments, arched frame 100 may have a consistent thickness between 1.5 and 2 millimeters. FIG. 2A illustrates an example arched frame comprising an adjustment mechanism. As shown in FIG. 2A, an arched frame 100 is provided comprising an arched body 105 defining a plurality of apertures 110 and an adjustment mechanism 115. In particular embodiments, arched body 105 may define a plurality of grooves, or a slot. Adjustment mechanism 115 may be coupled to arched body 105 along the midline of arched frame 100. In certain embodiments, Adjustment mechanism 115 may comprise a hook 120 and a threaded adjustor 125. FIGS. 2B and 2C illustrate arched frames each comprising a receiving mechanism. As shown in FIGS. 2B and 2C, an arched frame 100 is provided comprising an arched body 105 defining a plurality of apertures 110 and a receiving mechanism 130. In particular embodiments, receiving mechanism 130 may be a bar spanning a portion of the arch of arched body 105. In other embodiments, receiving mechanism 130 may be a surface coupled to the lingual portion of arched frame 100. In some embodiments, the surface may be rounded.

In particular embodiments, arched frame 100 may be formed from any material suitable for dental uses, for example, a hard plastic. Arched frame 100 may be formed from methyl methacrylate or a polycarbonate resin thermoplastic such as that sold under the Registered Trademark Lexan. Such materials are known to those familiar with dental devices, and other suitable materials may be used to form arched frame 100 without departing from the intended scope of the present invention.

Figure 3B:
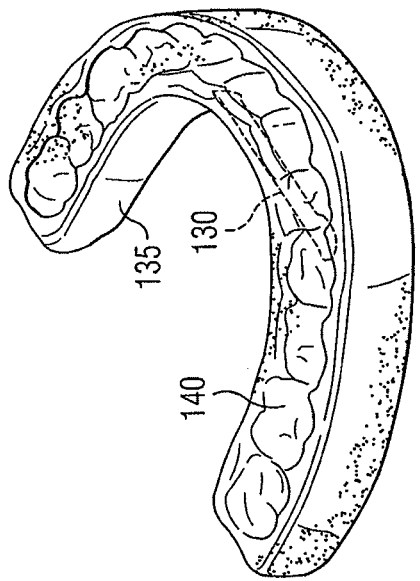
FIG. 3B illustrates an example arched frame comprising a receiving mechanism, and an example moldable tray.
Figure 3D:
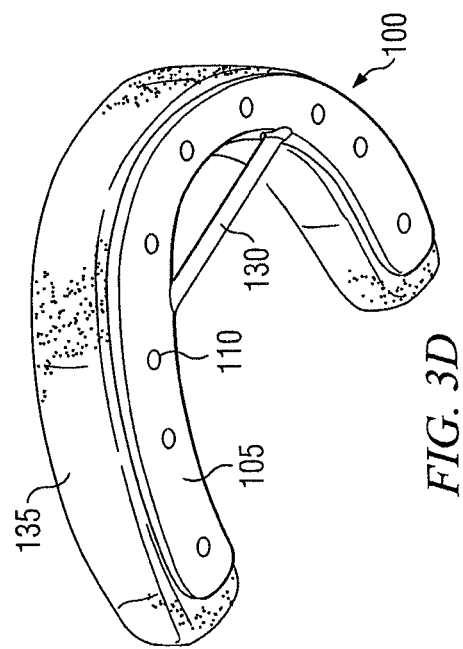
FIG. 3D illustrates an example arched frame comprising a receiving mechanism, and an example moldable tray.
Figure 3A:
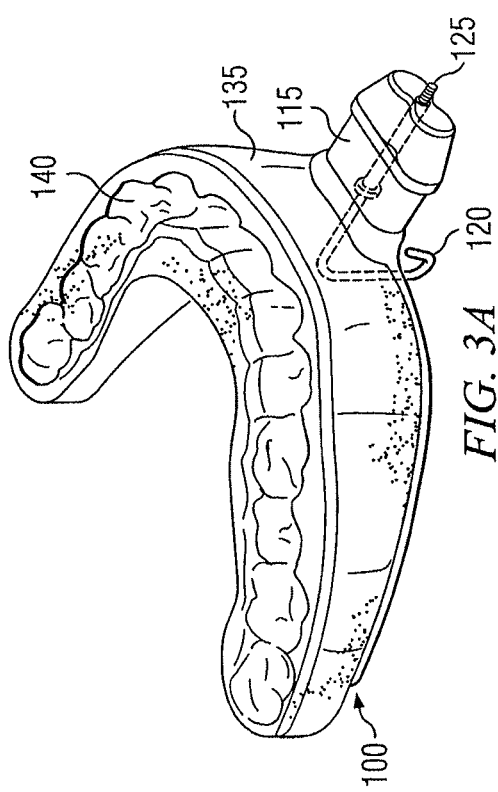
FIG. 3A illustrates an example arched frame comprising an adjustment mechanism, and an example moldable tray.
Figure 3C:
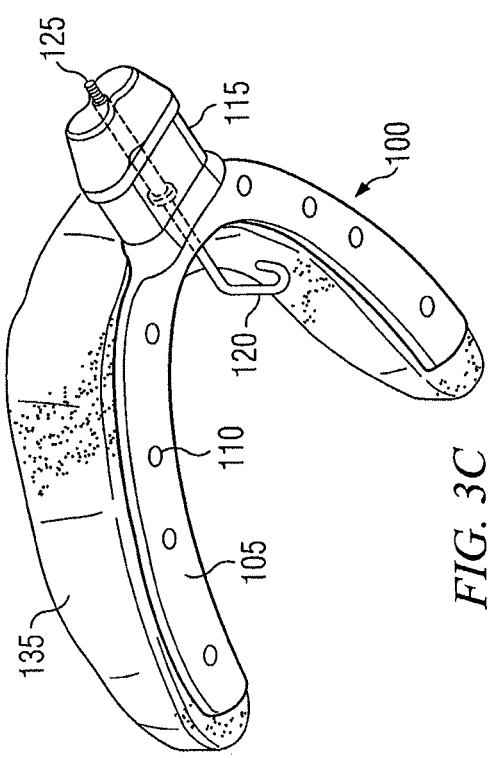
FIG. 3C illustrates an example arched frame comprising an adjustment mechanism, and an example moldable tray.

FIGS. 3A and 3C illustrate example arched frames each comprising an adjustment mechanism and example moldable trays. As shown in FIGS. 3A and 3C, an arched frame 100 and a moldable tray 135 are provided. Arched frame 100 may comprise an arched body 105 defining a plurality of apertures 110 and an adjustment mechanism 115. Moldable tray 135 may be coupled to arched frame 100 and may engage the plurality of apertures 110. In particular embodiments, moldable tray 135 may form through plurality of apertures 110 to couple to two sides of arched body 105. In some embodiments, moldable tray 135 may form into a plurality of grooves defined by arched body 105. In some embodiments, moldable tray 135 may be secured to arched frame 100 by forming through a slot defined by arched body 105. Moldable tray 135 may further comprise a channel 140 that is configured to engage at least some of a user's dental arch. In particular embodiments, channel 140 may engage the incisors and cuspids of the user's dental arch. In some embodiments, channel 140 may engage the incisors, cuspids, and some of the molars of the user's dental arch. In some embodiments, channel 140 may engage the incisors, cuspids, and all the molars of the user's dental arch. In particular embodiments, channel 140 may be shaped to conform to a generic user's teeth. In other embodiments, channel 140 may be a smooth channel that covers a user's teeth. In particular embodiments, channel 140 may be further shaped to conform to a particular user's teeth.

In particular embodiments, moldable tray 135 may comprise a polycaprolactone polymer or other aliphatic polyester. One or more of the polycaprolactone polymers may have the formula:

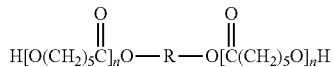

where R is an aliphatic hydrocarbon and n may range from approximately 300 to approximately 650. Certain embodiments may utilize polycaprolactone polymers using other suitable formulas. One particular embodiment may utilize Nylon.

Moldable tray 135 may include any suitable polycaprolactone polymer or other aliphatic polyester, for example, and not by way of limitation, the TONE P 700, TONE P 767, or TONE P 787 polycaprolactone polymers manufactured by Union Carbide Corporation, taken singly or in any combination. A suitable light cured material, another polymer, or any other suitable material, such as a filler, coloring agent, stabilizer, antioxidant, or antimicrobial agent, may be used to replace or combine with one or more of the polycaprolactone polymers in forming a deformable material 20 having any number of characteristics, properties, or uses.

The TONE polycaprolactone polymers are described in U.S. Pat. Nos. 5,112,225 and 4,784,123, and in literature distributed by Union Carbide Corporation, as homopolymers, block copolymers, graft copolymers, or other polymers that contain epsilon caprolactone. Polymerization may be initiated using one or more diols, for example, and not by way of limitation, ethylene glycol; diethylene glycol; neopentyl glycol; butane diol; hexane diol; or any other suitable diol.

In particular embodiments, moldable tray 135 may be custom molded to a user's teeth. For example, moldable tray 135 may comprise a material that is moldable when heated. Once heated, the material may be pressed around a user's dental arch to form a moldable tray 135 that conforms to the user's teeth. In particular embodiments, moldable tray 135 may be used with arched frame 100 to form a custom dental device. For example, arched frame 100 may comprise a hard plastic material. When moldable tray 135 is forming around a user's teeth, arched frame 100 may be pressed against moldable tray 135, so that mold tray 135 forms through plurality of apertures 110 defined by arched body 105. As moldable tray 135 cools and hardens, moldable tray 135 may couple to arched frame 100 through plurality of apertures 110. In some embodiments, moldable tray 135 may couple to arched frame 100 through a slot or by forming into a plurality of grooves. In particular embodiments, arched frame 100 may provide structural support for moldable tray 135 as moldable tray 135 engages the user's teeth. For example, as moldable tray 135 engages the user's teeth, arched frame 100 may prevent moldable tray 135 from deforming or shifting under the stresses caused by movement of the user's mouth.

In particular embodiments, a custom dental device may comprise arched frame 100 and moldable tray 135. A dentist may be able to construct the custom dental device for a patient without having to send the patient's dental impressions to a lab. The dentist may heat moldable tray 135 and press moldable tray 135 around the user's teeth. The dentist may then press arched frame 100 against moldable tray 135 to construct the custom dental device. As a result, the patient may not have to wait for the lab to create the dental device, nor does the patient have to pay an extra fee charged by the lab.

FIGS. 3B and 3D illustrate example arched frames each comprising a receiving mechanism, and example moldable trays. As shown in FIGS. 3B and 3D, an arched frame 100 and a moldable tray 135 are provided. Arched frame 100 may comprise an arched body 105 defining a plurality of apertures 110 and a receiving mechanism 130. Receiving mechanism 130 may be coupled to arched body 105. In particular embodiments, receiving mechanism 130 may be a bar that spans a portion of the arch of arched body 105. Moldable tray 135 may comprise a channel 140 that is configured to engage at least some of the teeth of a user's dental arch.

Figure 4:
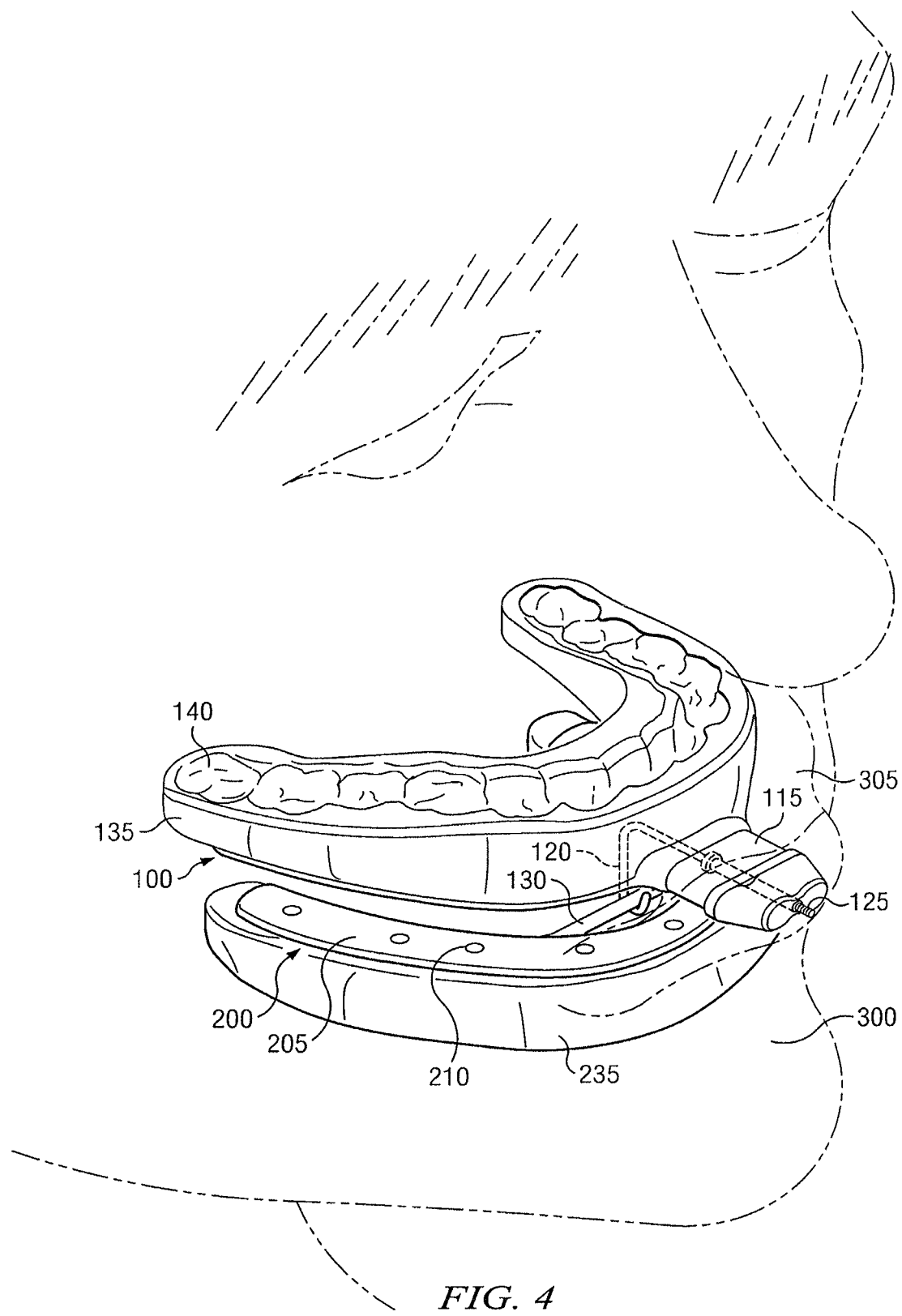
FIG. 4 illustrates an example dental device in a user's mouth.

FIG. 4 illustrates an example dental device in a user's mouth. As shown in FIG. 4, a dental device is provided that comprises an arched frame 100, a moldable tray 135, a second arched frame 200, and a second moldable tray 235. Arched frame 100 may comprise an adjustment mechanism 115 that comprises a hook 120 and a threaded adjustor 125. Moldable tray 135 may be coupled to arched frame 100. Moldable tray 100 may comprise a channel 140. In some embodiments, channel 140 may be shaped to conform to a generic user's maxillary arch 305. In other embodiments, channel 140 may be a smooth channel that covers some of teeth of a user's maxillary arch 305. In particular embodiments, channel 140 may be further shaped to conform to a particular user's maxillary arch 305. Second arched frame 200 may comprise a second arched body 205 defining a second plurality of apertures 210. Second arched frame 200 may further comprise a receiving mechanism 130 coupled to the lingual portion of second arched body 205. In some embodiments, receiving mechanism 130 may be a bar that spans a portion of the arch of second arched body 205. Second moldable tray 235 may be coupled to second arched frame 200 and may engage second plurality of apertures 210. Second moldable tray 235 may be configured to engage some of the teeth of the user's mandibular arch 300. In particular embodiments, hook 120 may engage receiving mechanism 130. Threaded adjustor 125 may be used to adjust the forward position of arched frame 100 relative to second arched frame 200. The relative positions of the two arched frames 100 and 200 may adjust the position of the user's maxillary arch 305 relative to the user's mandibular arch 300. In some embodiments, the relative position of the user's maxillary and mandibular arches may help to improve a user's breathing and/or prevent the user from snoring while sleeping.

Figure 5A:
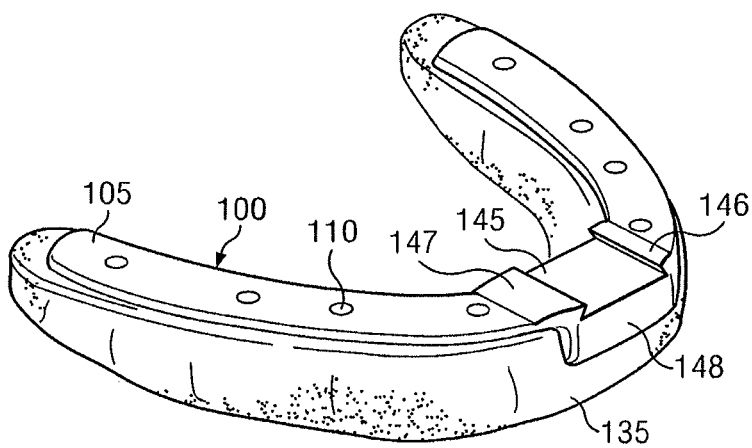
FIG. 5A illustrates an example universal oral appliance comprising a universal coupler.
Figure 5B:
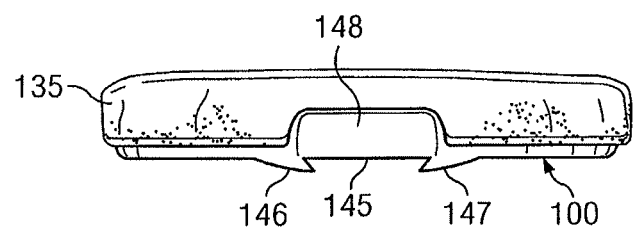
FIG. 5B illustrates an example universal oral appliance comprising a universal coupler.

FIGS. 5A and 5B each illustrate an example universal oral appliance comprising a universal coupler. As shown in FIGS. 5A and 5B, a universal oral appliance is provided comprising an arched frame 100 and a moldable tray 135 coupled to arched frame 100. Arched frame 100 may comprise an arched body 105 defining a plurality of apertures 110. In particular embodiments, arched frame 100 may be configured to be positioned proximate to the occlusal surface of a user's dental arch such that arched frame 100 extends beyond the cuspids of the user's dental arch when arched frame 100 is inserted in the user's mouth. Arched frame 100 may have a midline that aligns substantially with the anterior midline of the user's mouth when arched frame 100 is inserted in the user's mouth. Arched frame 100 may further comprise a universal coupler. In particular embodiments, the universal coupler may comprise a substantially planar surface 145, a first rail 146, and a second rail 147. Substantially planar surface 145 may be proximate to and extend across the midline of arched frame 100. In particular embodiments, substantially planar surface 145 may be configured to be positioned proximate to the occlusal surface of a user's incisors when the universal oral appliance is inserted in the user's mouth. First rail 146 may be coupled to a first end of substantially planar surface 145. In particular embodiments, first rail 146 may be distal to the midline of arched frame 100. In other embodiments, first rail 146 may be anterior to arched frame 100. Second rail 147 may be coupled to a second end of substantially planar surface 145. In particular embodiments, second rail 147 may be distal to the midline of arched frame 100. In other embodiments, second rail 147 may be posterior to arched frame 100. First rail 146 and second rail 147 may form an acute angle with substantially planar surface 145. In particular embodiments, first rail 146, second rail 147, and substantially planar surface 145 may define a slot. In particular embodiments, a dental attachment may slide into the slot and engage arched frame 100. In some embodiments, the universal coupler may comprise a locking mechanism (such as, for example, a screw, a tab, or a groove). The screw may secure a dental attachment to the universal coupler by screwing through the dental attachment and into the universal coupler. The tab may secure the dental attachment by engaging the exterior of the dental attachment or by engaging a slot in the dental attachment. The groove may secure the dental attachment by frictionally engaging the dental attachment. In particular embodiments, the universal coupler may further comprise a stop 148 coupled to substantially planar surface 145. Stop 148 may be coupled to the labial or lingual ends of substantially planar surface 145. Alternatively, stop 148 may be coupled to a distal end of substantially planar surface 145. Although this disclosure describes a universal oral appliance comprising arched frame 100, moldable tray 135, and a universal coupler coupled to arched frame 100, this disclosure contemplates a one-piece universal oral appliance and a universal coupler coupled to the universal oral appliance.

Figure 5C:
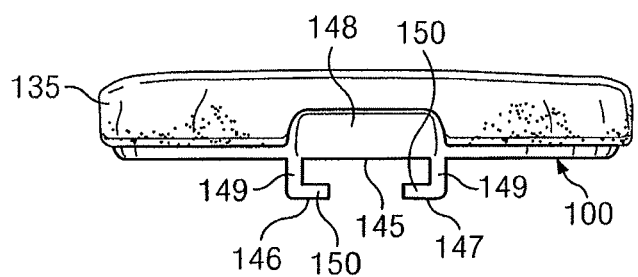
FIG. 5C illustrates an example universal oral appliance comprising a universal coupler.

FIG. 5C illustrates an example universal oral appliance comprising a universal coupler. As shown in FIG. 5C, a universal oral appliance is provided comprising an arched frame 100 and a moldable tray 135 coupled to arched frame 100. Arched frame 100 may comprise a universal coupler comprising a substantially planar surface 145, a first rail 146, a second rail 147, and a stop 148. In particular embodiments, each rail 146 and 147 may comprise a first segment 149 and a second segment 150. First segment 149 may be coupled at a first end to substantially planar surface 145, and second segment 150 may be coupled to a second end of first segment 149. In particular embodiments, first segment 149 and second segment 150 may be substantially perpendicular to each other.

Figure 5D:
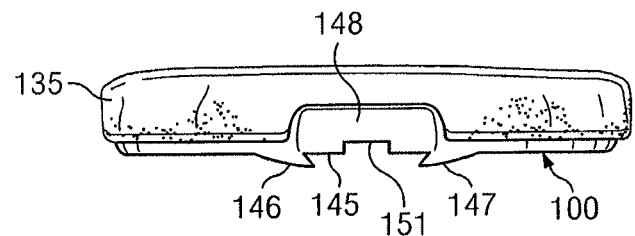
FIG. 5D illustrates an example universal oral appliance comprising a universal coupler comprising a guided channel.

FIG. 5D illustrates an example universal oral appliance comprising a universal coupler comprising a guided channel. As shown in FIG. 5D, a universal oral appliance is provided comprising an arched frame 100 and a moldable tray 135. Arched frame 100 may comprise a universal coupler comprising a substantially planar surface 145, a first rail 146, a second rail 147, and a stop 148. First rail 146, second rail 147, and substantially planar surface 145 may define a slot. In particular embodiments, the universal coupler may further comprise a guided channel 151. Guided channel 151 may be configured to guide a dental attachment through the slot.

Figure 5E:
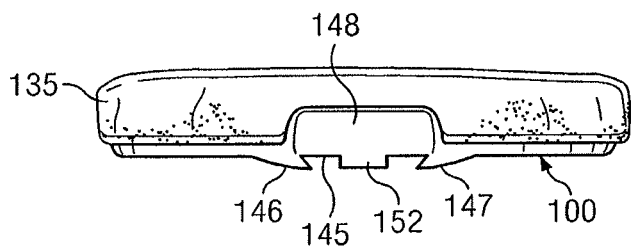
FIG. 5E illustrates an example universal oral appliance comprising a universal coupler comprising a raised surface.

FIG. 5E illustrates an example universal oral appliance comprising a universal coupler comprising a raised surface 152. As shown in FIG. 5E, a universal oral appliance is provided comprising an arched frame 100 and a moldable tray 135. Arched frame 100 may comprise a universal coupler comprising a substantially planar surface 145, a first rail 146, a second rail 147, and a stop 148. First rail 146, second rail 147, and substantially planar surface 145 may define a slot. In particular embodiments, the universal coupler may further comprise a raised surface 152. Raised surface 152 may be configured to guide a dental attachment through the slot. In particular embodiments, raised surface 152 may be further configured to secure or lock the dental attachment.

Figure 6:
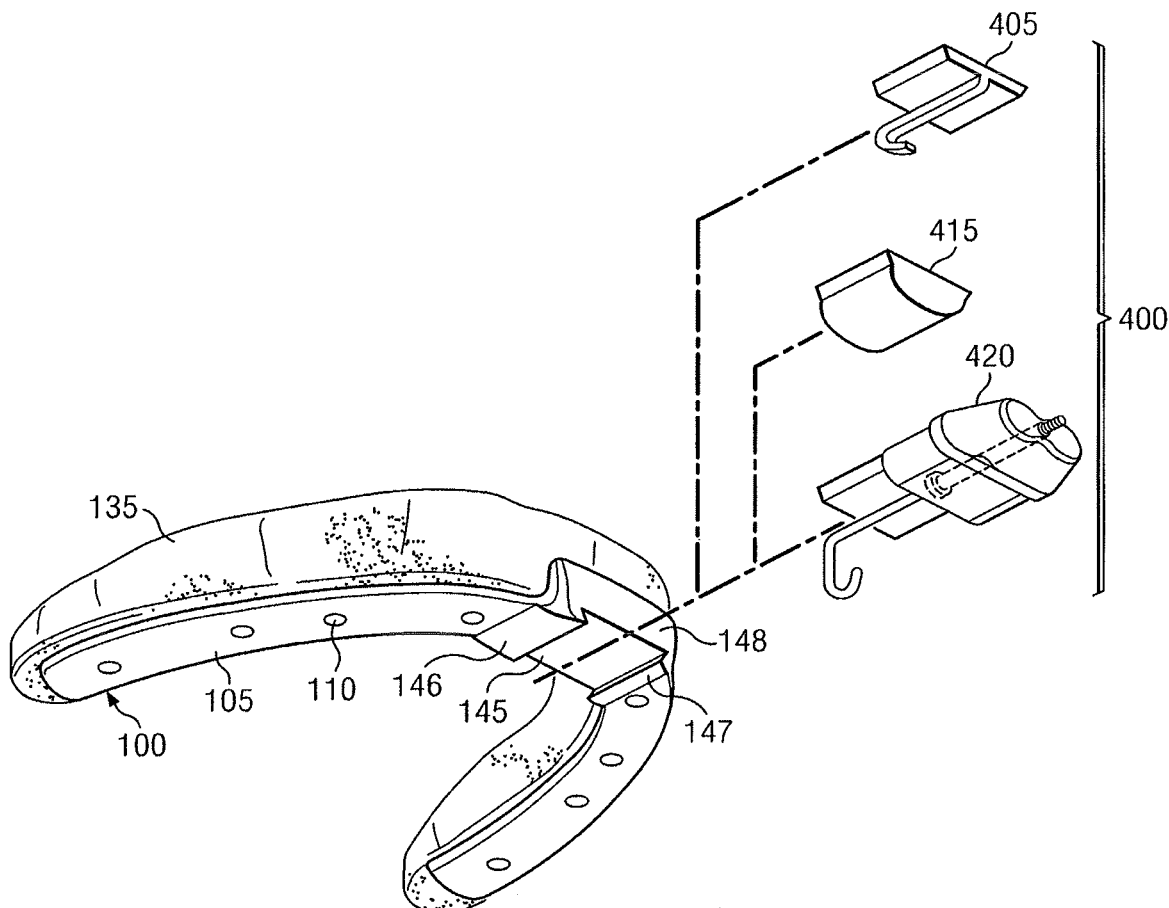
FIG. 6 illustrates an example universal oral appliance comprising a universal coupler, and an example plurality of dental attachments.

FIG. 6 illustrates an example universal oral appliance comprising a universal coupler, and an example plurality of dental attachments 400. As shown in FIG. 6, an example universal oral appliance is provided that comprises an arched frame 100 and a moldable tray 135. Arched frame 100 comprises an arched body 105 that defines a plurality of apertures 110. Arched frame 100 further comprises a universal coupler. The universal coupler may comprise a substantially planar surface 145, a first rail 146, a second rail 147, and a stop 148. In particular embodiments, first rail 146, second rail 147, and substantially planar surface 145 may define a slot. FIG. 6 also illustrates a plurality of dental attachments 400. In particular embodiments, the plurality of dental attachments 400 may comprise dental attachments configured to treat different disorders. For example, the plurality of dental attachments 400 may include a hook 405, a substantially rounded projection 415, and an adjustable hook 420. Other attachments may include a handle or any other appropriate attachment configured for use with an oral appliance. A user or a medical professional may choose which dental attachment to use without having to hire a lab to construct a new oral appliance. In some embodiments, dental attachments 400 may be configured to engage the slot.

Figure 7:
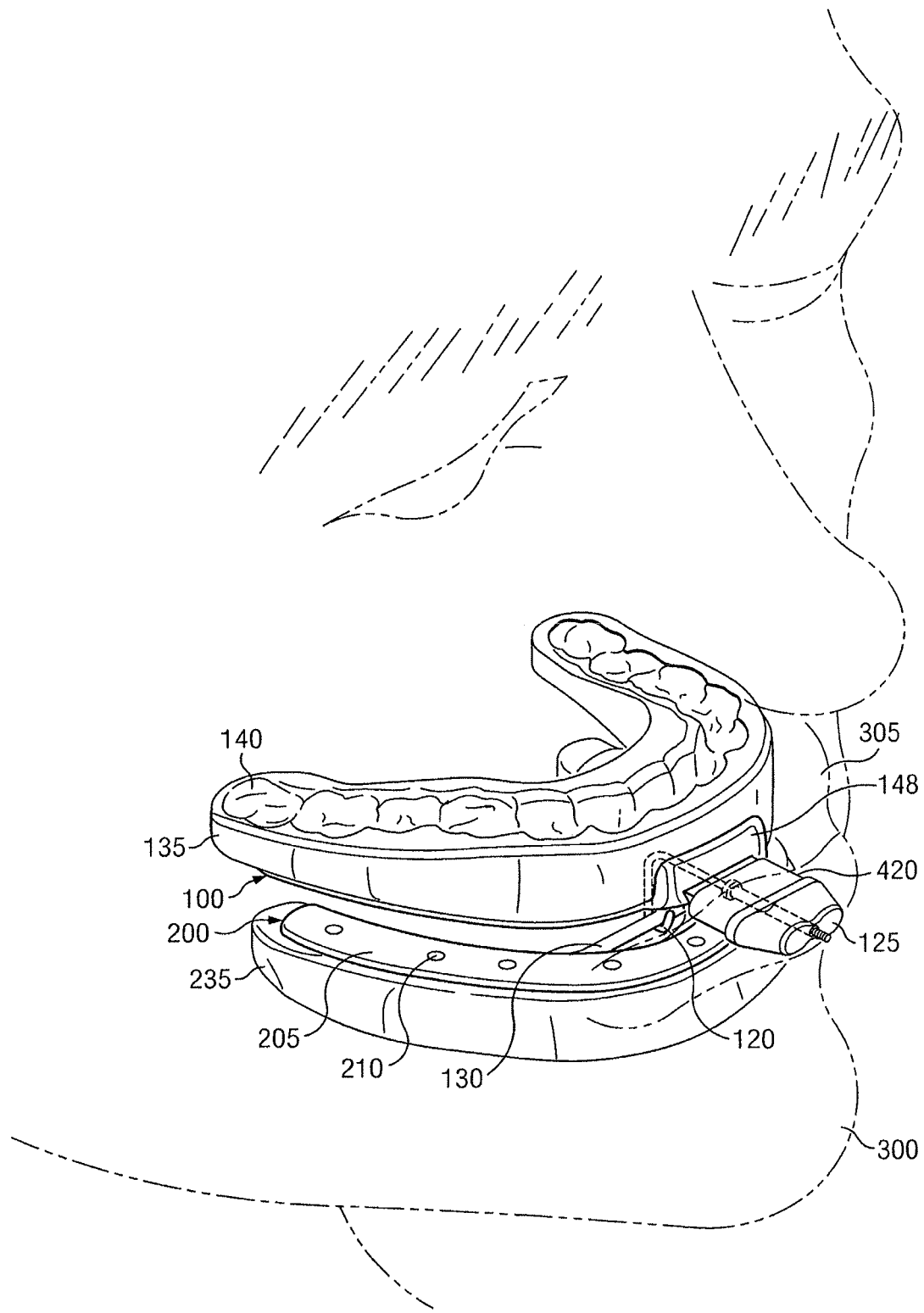
FIG. 7 illustrates an example dental device in a user's mouth.

FIG. 7 illustrates an example dental device in a user's mouth. As shown in FIG. 7, a dental device is provided that comprises an arched frame 100, a moldable tray 135 coupled to arched frame 100, a second arched frame 200, and a second moldable tray 235 coupled to arched frame 200. Arched frame 100 may comprise a universal coupler. The universal coupler may comprise a stop 148. Moldable tray 135 may comprise a channel 140 that is configured to engage at least some of the teeth of the user's maxillary arch 305. Second arched frame 200 may comprise a second arched body 205 that defines a second plurality of apertures 210. Second arched frame 200 may further comprise a receiving mechanism 130 that spans the lingual portion of second arched frame 200. In particular embodiments, receiving mechanism 130 may be a bar. Second moldable tray 235 may engage second plurality of apertures 210. The dental device further comprises a dental attachment that is configured to engage the universal coupler. In some embodiments, the dental attachment may be an adjustable hook 420 that comprises a hook 120 and a threaded adjustor 125. Hook 120 may engage receiving mechanism 130. Threaded adjustor 125 may be used to adjust the forward position of second arched frame 200 relative to arched frame 100. This adjustment may adjust the forward position of the user's mandibular arch 300 relative to the position of the user's maxillary arch 305. In some embodiments, this adjustment may help to prevent the user from snoring while sleeping.

FIG. 8A illustrates an example arched frame 700. Arched frame 700 may include an occlusal surface 702 and a flange 706. In particular embodiments arched frame 700 may be configured to be positioned proximate to a user's dental arch, with occlusal surface 702 positioned proximate to the occlusal surface of the user's dental arch. In certain embodiments, occlusal surface 702 may be contiguous throughout the length of arched frame 700. In alternative embodiments, as shown in FIG. 8A, occlusal surface 702 may not be contiguous throughout the length of arched frame 700. For example, occlusal surface 702 may have a first portion configured to be positioned proximate to the user's left bicuspid and first molar; and have a second portion configured to be positioned proximate to the user's right bicuspid and first molar. As shown in FIG. 8A, in certain embodiments, occlusal surface 702 may not extend to the area proximate to the user's incisors. Certain embodiments in which the occlusal surface 702 is not contiguous throughout the length of arched frame 700 may allow for improved flexibility of arched frame 700. In certain embodiments, arched frame 700 may be capable of flexing inward and/or outward, allowing arched frame 700 to conform to a wider variety of dental arch shapes and sizes. Such embodiments may also improve the ability of arched frame 700 to accommodate the overlap of the user's maxillary and mandibular incisors, allowing the user's jaw to close more fully. In certain embodiments, occlusal surface 702 may have a thickness of approximately 1.5 millimeters, although other thicknesses may be used.

Flange 706 may run along the labial edge of arched frame 700. In certain embodiments, flange 706 may be contiguous throughout the length of arched frame 700. In alternative embodiments, as shown in FIG. 8A, flange 706 may not be contiguous throughout the length of the arched frame. For example, flange 706 may include a distal flange portion 708 and a mesial flange portion 710, separated by a flange recess 712. In certain embodiments, because flange 706 is positioned proximate to the labial surface of the user's dental arch, it may be pushed outward by the labial surface of the user's dental arch when arched frame 700 is inserted into the user's mouth during the molding process, allowing arched frame 700 to automatically flex and align with the user's dental arch, which may improve the ability of arched frame 700 to accommodate different dental arch sizes and shapes. In certain embodiments, flange recesses 712 may allow for improved flexibility of arched frame 700. In addition, when arched frame 700 is used with deformable material, flange recesses 712 may allow the deformable material to form an improved mold of the user's teeth. In some embodiments, flange recess 712 may improve the user's ability to press moldable material against their teeth during the molding process, which allow for improved dental molds. In certain embodiments, mesial flange portion 710 may allow for an improved mold when arched frame 700 is pressed toward the user's teeth during fitting. As shown in FIG. 8A, in certain embodiments mesial flange portion 710 may have a thickness greater than that of distal flange portion 708. For example, mesial flange portion 710 may have a thickness of approximately 3 millimeters and distal flange portion 708 may have a thickness of approximately 1.5 millimeters, although other thicknesses may be used. In such embodiments, the greater thickness of mesial flange portion 710 may improve the stability of arched frame 700 during flexion and may provide a more secure anchor point for other attached structures, such as anterior structure 716 shown in FIG. 8B.

FIG. 8B illustrates another example arched frame 700 having occlusal surface 702, flange 706, and an anterior structure 716. As shown in FIG. 8B, in certain embodiments occlusal surface 702 may include an occlusal surface recess 704. When arched frame 700 is used with deformable material, occlusal surface recess 704 may allow the deformable material to form a closer mold of the user's teeth. As shown in FIG. 8B, certain embodiments may include anterior structure 716 which extends forward from mesial flange portion 710 in an anterior direction. In certain embodiments, anterior structure 716 may be fixed to arched frame 700, while in other embodiments anterior structure 716 may removeably coupled to arched frame 700. FIGS. 8C and 8D illustrate side views of example arched frames 700 having occlusal surface 702 and flange 706 with distal flange portion 708, flange recess 712, and anterior structure 710.

FIG. 8E illustrates an isometric view of an example arched frame 700. As shown in FIG. 8E, arched frame 700 may include anterior structure 710, occlusal surface 702 that is not contiguous throughout the length of arched frame 700, and flange 706 that includes a distal flange portion 708, a flange recess 712, a mesial flange portion 710, and a mesial flange recess 714. As shown in FIG. 8E, flange 706 may include mesial flange recess 714 located approximately at the midline of the arched frame. In such embodiments, mesial flange recess 714 may allow for improved conformity with the shape of the user's mouth. In certain embodiments, the distal ends of arched frame 700 may extend approximately to the user's first molar when the frame is inserted into the user's mouth. In alternative embodiments, arched frame 700 may extend to the user's second molar or to the user's third molar.

Figure 9A:
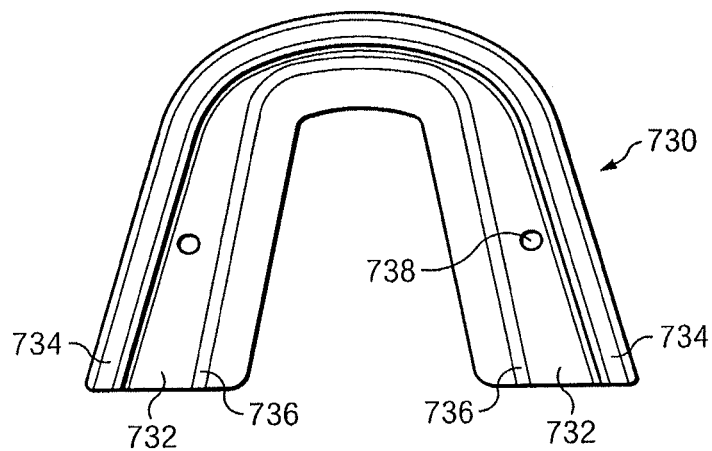
FIGS. 9A through 9D illustrate an example moldable tray.

FIGS. 9A through 9D illustrate example moldable trays 730. As shown in FIG. 9A, moldable tray 730 may include an occlusal surface 732, an outer rim 734, an inner rim 736, and recesses 738. Occlusal surface 732 may be configured to be placed proximate to the occlusal surface of a user's dental arch. Outer rim 734 may be configured to be positioned proximate to the labial surface of a user's dental arch. In certain embodiments, inner rim 736 may be configured to be positioned proximate to the lingual surface of a user's dental arch. In certain embodiments, inner rim 736 may lie mostly flat relative to the plane of occlusal surface 732 or may angle upward slightly. Such embodiments may make moldable tray 730 easier to slide into the user's mouth. In certain embodiments, inner rim 736 may be capable of being pushed upward or downward to engage with the lingual surface of the user's dental arch during the molding process.

As shown in FIG. 9A, in certain embodiments outer rim 734 may have a thickness greater than that of inner rim 736. For example, in certain embodiments, outer rim 734 may have a thickness of approximately 3 millimeters, while inner rim 736 may have a thickness of approximately 2 millimeters, although these dimensions are not required. Reduced thickness of inner rim 736 may allow moldable tray 730 to take up less space in the inner mouth area behind the teeth, which may allow the user to breath, swallow, and speak more easily and experience greater comfort. Reduced thickness of inner rim 736 may also help obviate any need to offer multiple sizes of moldable tray 730 and arched frame 700. In certain embodiments, reduced thickness of inner rim 736 may allow other medical and/or dental devices to be more easily inserted into the user's mouth. In certain embodiments, as shown in FIG. 9D, inner rim 736 may be shorter than outer rim 734. A shorter inner rim 736 may allow for easier insertion of moldable tray 730 into the user's mouth. A shorter inner rim 736 may also reduce the amount of moldable material in the inner mouth area, which may provide additional advantages as described above. In certain embodiments, distal portions of moldable tray 730 may have a reduced height, which may improve the fit of moldable tray 730 in the user's mouth.

As shown in FIG. 9A, in certain embodiments occlusal surface 732 may have one or more recesses 738, which may result from clamping or otherwise holding in place arched frame 700 during an overmolding process. In certain embodiments, arched frame 700 illustrated in FIGS. 8A through 8E may have a corresponding recess, which may allow for improved clamping and alignment during the manufacturing process.

Figure 9B:
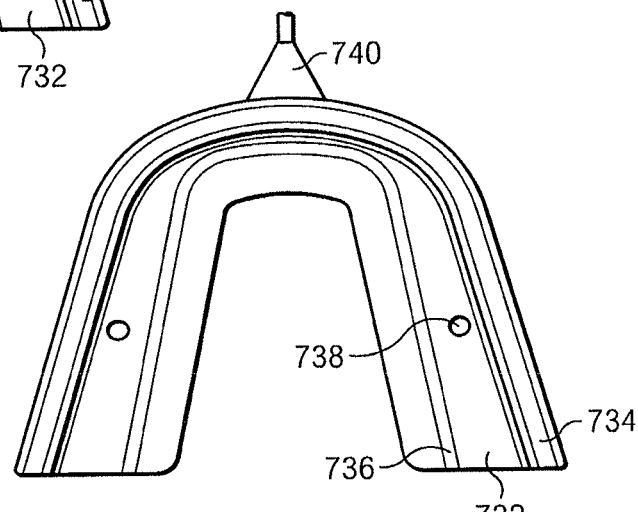
Figure 9C:
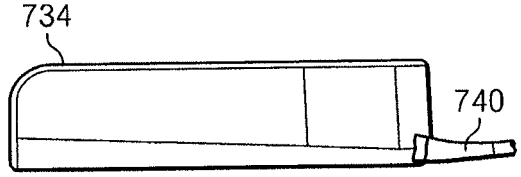
Figure 9D:
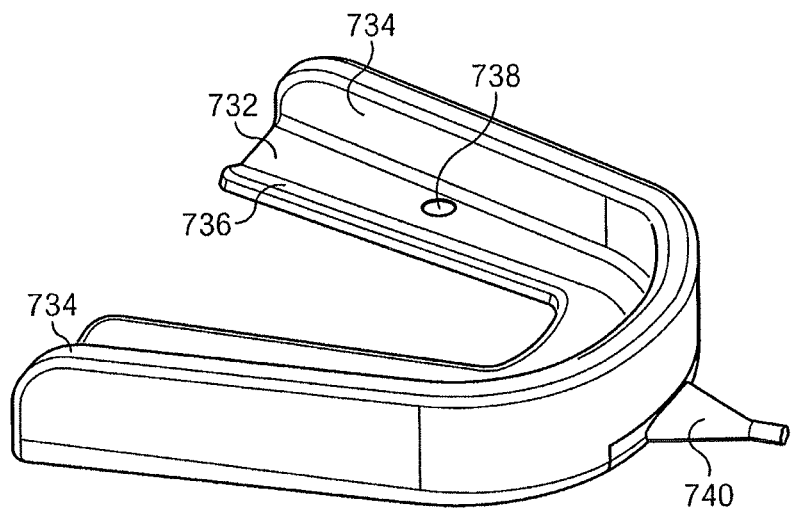

FIG. 9B shows another example moldable tray 730 having occlusal surface 732, outer rim 734, and inner rim 736. As shown in FIG. 9B, in certain embodiments moldable tray 730 may further include an anterior structure 740. It should be appreciated that in certain embodiments the optional anterior structure 740 may be fixed to moldable tray 730 or it may be removeably coupled to moldable tray 730.

In certain embodiments, moldable tray 730 may be composed of a material that can be heated to a temperature at which the material softens and becomes capable of being molded to a different shape. In certain embodiments, the material can be heated in hot water. In some embodiments, the temperature range at which the material softens may be approximately 40-80 degrees Celsius, although materials with other softening ranges may be used. In a particular embodiment, the target softening temperature may be approximately 60 degrees Celsius. In certain embodiments, this material may be a thermoplastic. Such thermoplastic materials may be heated to a temperature at which the thermoplastic becomes soft and moldable, at which point it may be molded to the shape of at least a portion of a user's dental arch and become at least temporarily fixed in that shape. As one example, moldable tray 730 may comprise a polycaprolactone polymer or other aliphatic polyester, as discussed above in reference to moldable tray 135. In particular embodiments, the thermoplastic material may comprise a cross-linked polycaprolactone reinforced with an aramid fiber such as the short length aramid fiber sold by Dupont under the brand name Kevlar®. In certain embodiments, using polycaprolacton combined with Kevlar® may allow moldable tray 730 to soften at low temperatures and set hard at temperatures of approximately 60 degrees Celsius. In certain embodiments, using polycaprolacton combined with Kevlar® may improve the hardness of moldable tray 730 following the molding process, which may improve the ability of moldable tray 730 to hold its shape when being used to adjust the user's jaw position and/or hold a mask or other breathing device in place. In certain embodiments, this increased hardness may also improve the ability of moldable tray 730 to hold its shape for longer periods of time. For example, in certain embodiments, this may allow moldable tray 730 to substantially hold its shape for periods longer than approximately 1 month, though such period is not required. Using polycaprolacton combined with Kevlar® may also allow for thinner embodiments of moldable tray 730, which may allow moldable tray 730 to take up less space in the user's mouth. Examples of polycaprolactone combined with an aramid fiber, including Kevlar® and a variety of other fibers, are described in U.S. application Ser. No. 11/368,991, publication number U.S. 2007/0004993 A1, which is incorporated herein by reference. Such embodiments may provide an improved moldable material that better maintains its form when heated, providing increased viscosity which may prevent the material from flowing excessively around the user's teeth and/or getting stuck on the user's teeth during the molding process. Such embodiments may also possess increased strength after molding. In certain embodiments, the thermoplastic material may be cross-linked by radiation, which may create cross-linking of certain molecules to improve the material's shape retention characteristics and/or make the material better able to return to its original shape after reheating. In certain embodiments, radiation may be applied after moldable tray 730 has been overmolded with arched frame 700, but before being molded to the user, though this is not required. Cross-linking by radiation is further described in U.S. Pat. No. 5,415,623, which is incorporated herein by reference. In certain embodiments, the material may exhibit slight shrinkage after being molded to the user's dental arch. In particular embodiments, such shrinkage may be less than 1%. Slight shrinkage of the material following the molding process may allow for improved fit with the user's dental arch. In some embodiments, slight shrinkage of the material following the molding process may allow moldable tray 730 to have a "snap" fit with the user's dental arch.

In some embodiments, arched frame 700 may be primarily composed of a substantially rigid material, such as Nylon or any other material providing substantial rigidity while allowing moderate flexion. In certain embodiments, arched frame 700 may be composed of a material whose form does not substantially changed when heated to the temperature required to soften the moldable material of moldable tray 730. For example, in some embodiments, arched frame 700 may be composed of a material that substantially maintains its shape when heated up to at least 100 degrees Celsius. Such materials may include polycarbonate, Nylon, acrylonitrile butadiene styrene (ABS), or polyethylene. In certain embodiments, arched frame 700 may be composed of a semi-flexible material, for example liquid silicone rubber (LSR), approximately having a Shore 30-90 hardness, although this particular hardness is not required.

Figure 10A:
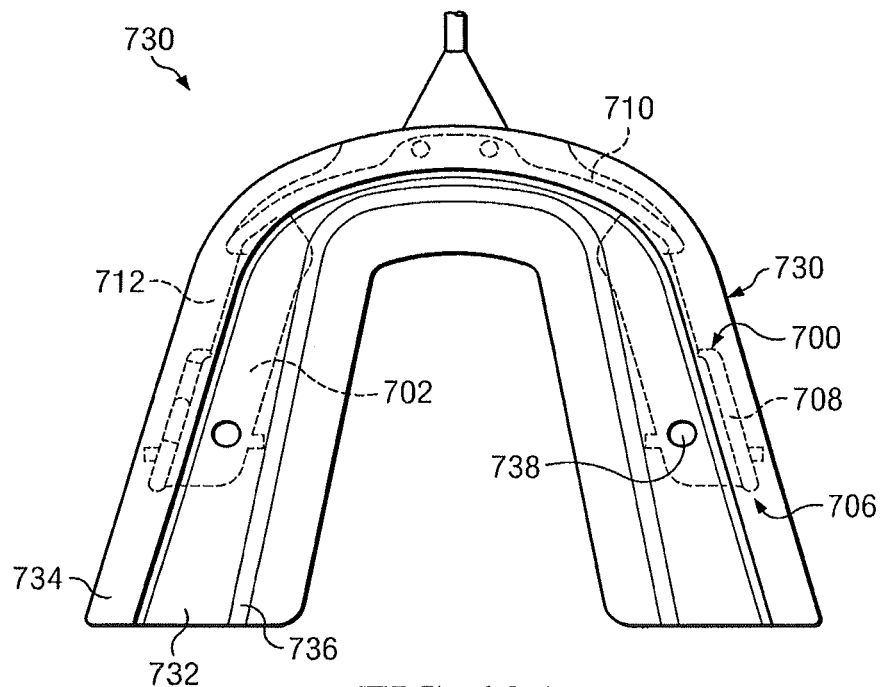
FIGS. 10A through 10C illustrate an example arched frame disposed within an example moldable tray.
Figure 10B:
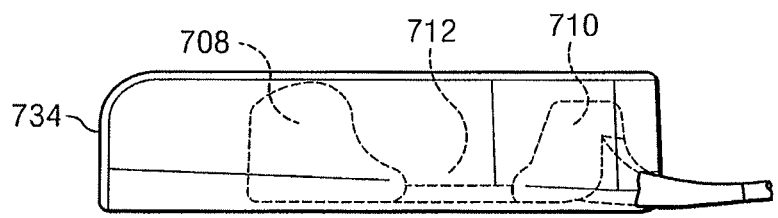
Figure 10C:
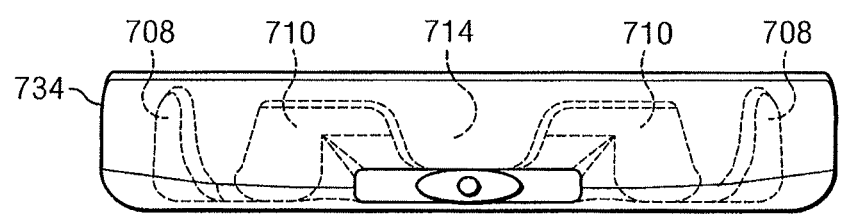

FIGS. 10A through 10C illustrate an example moldable tray 730 substantially surrounding an example arched frame 700. As shown in FIG. 10A, example moldable tray 730 may include occlusal surface 732, outer rim 734, and inner rim 736; and arched frame 700 may include occlusal surface 702 and flange 706. As shown in FIG. 10A, in certain embodiments the labial edge of outer rim 734 may extend outward beyond the labial edge of flange 706. The lingual edge of inner rim 736 may also extend inward beyond the labial edge of occlusal surface 702. As seen in FIG. 10B, in certain embodiments the distal end of moldable tray 730 may extend distally beyond the distal end of arched frame 700. In certain embodiments, the distal end of arched frame 700 may extend approximately to the user's first molar, while the distal end of moldable tray 730 extends approximately to the user's second or third molar. In alternative embodiments, the distal end of arched frame 700 may extend approximately to the user's second molar, while the distal end of moldable tray 730 extends approximately to the user's third molar. In still other embodiments, the distal ends of arched frame 700 and moldable tray 730 may be approximately coextensive.

In certain embodiments, when moldable tray 730 is oriented for placement on, for example, a user's maxillary arch, the superior surface of outer rim 734 may extend beyond the superior surface of flange 706 by approximately 2.5 millimeters while the inferior surface of moldable tray 730 may extend below the inferior surface of arched frame 700 by approximately 1.5 millimeters, although these dimensions are not required. In certain embodiments, moldable tray 730 may extend outward beyond the labial edge of arched frame 700 by approximately 1.5 millimeters, though other dimensions are possible. In certain embodiments, moldable tray 730 may extend inward beyond the lingual edge of arched frame 700 by approximately 1.5 millimeters, though other dimensions are possible.

In certain embodiments, flange 706 may help maintain the shape of outer rim 734. Moldable trays that substantially surround an arched frame may allow for reduced bulk between a user's incisors when the tray(s) are inserted into the user's mouth. By providing moldable trays with less material between the user's incisors, certain embodiments may allow users to close their mouths further with the trays inserted, which may improve comfort and/or effectiveness. Furthermore, moldable trays that substantially surround arched frame may allow for mouth pieces where only the moldable material touches the inner surfaces of the user's mouth, such as the user's gums, lips, and tongue. Such moldable trays may also allow for improved molding to the user's front teeth. Having arched frame 700 substantially surrounded by moldable tray 730 may also reduce the chances of damage to arched frame 700 and may help hold any broken pieces of arched frame 700 in place, preventing any such broken pieces from contacting the user's mouth or entering the user's airway.

In certain embodiments, arched frame 700 may include apertures in occlusal surface 702 and/or flange 706, though such apertures are not required. Such apertures may allow the moldable material to flow through arched frame 700 during the molding process, which may provide greater stiffness following the molding process and may allow for improved alignment of arched frame 700 with moldable tray 730.

Figure 11A:
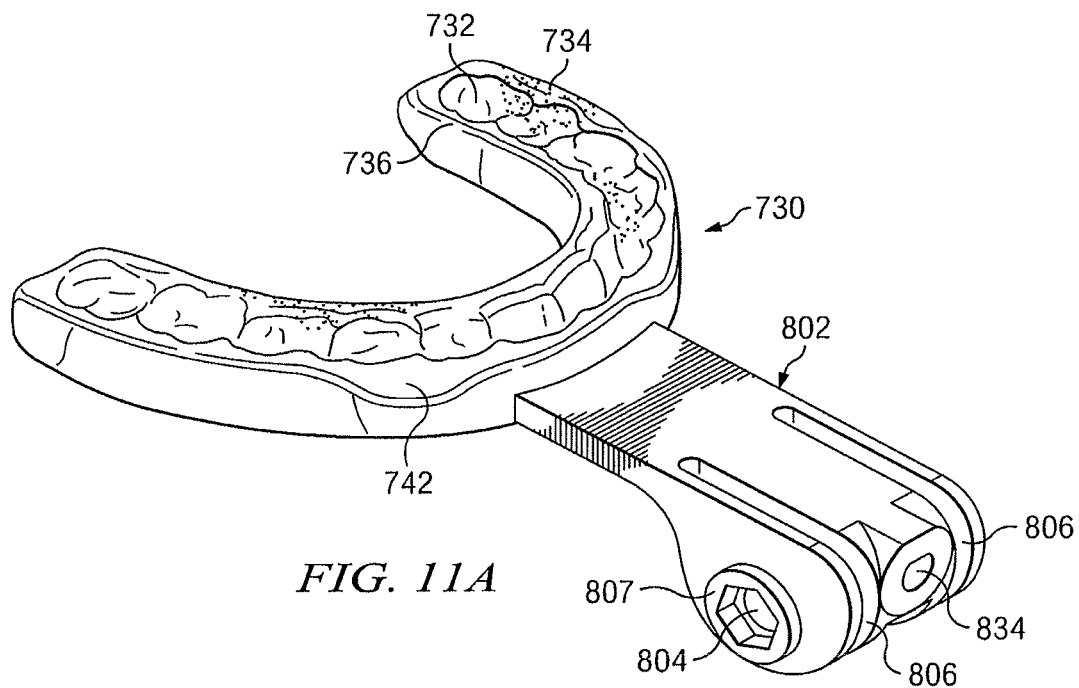
FIGS. 11A and 11B illustrate an example moldable tray and an example post.
Figure 11B:
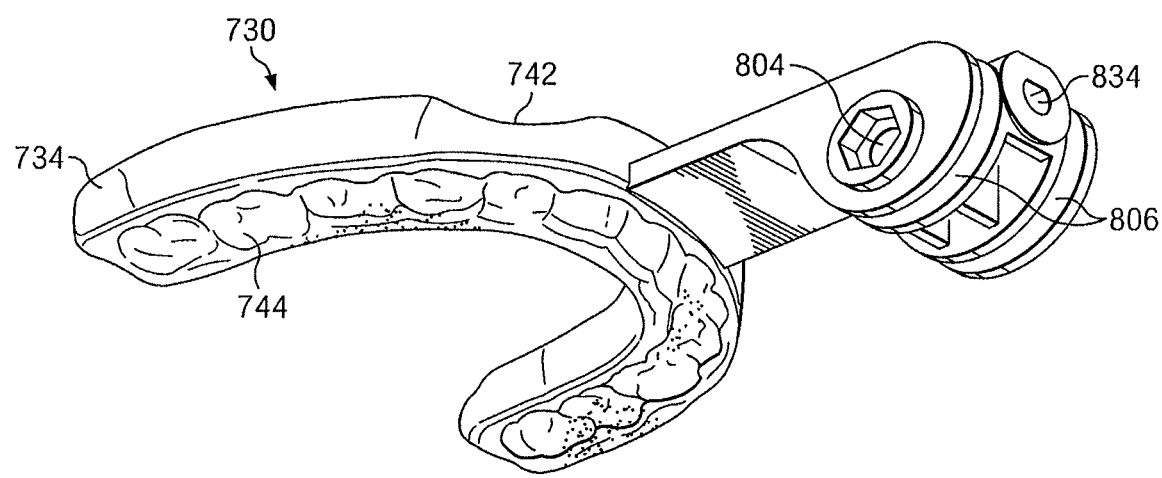

FIG. 11A illustrates another example moldable tray 730 having occlusal surface 732, outer rim 734, inner rim 736, and notches 742. In this embodiment, moldable tray 730 is attached to a post 802 having slot 804, channels 806, and tension element channel 834. FIG. 11B also illustrates a lower isometric view of the same embodiment showing outer rim 734, notch 742, and a lower surface 744. As shown in FIG. 11A, in certain embodiments moldable tray 730 may be custom molded to fit a particular user's dental arch. In particular embodiments moldable tray 730 may include one or more notches 742 which may facilitate grasping the moldable tray for improved insertion into and removal from the user's mouth. As shown in FIG. 11B, in certain embodiments lower surface 744 of the moldable tray 730 may also be molded to fit the user's second dental arch. In certain embodiments, molding lower surface 744 to the user's mandibular dental arch may be performed with the user's mandibular dental arch placed in a particular position relative to the user's maxillary dental arch. For example, the user's mandibular dental arch may be extended in the anterior direction, which may help open a user's airway allowing for improved breathing. Molding lower surface 744 to the user's mandibular dental arch may also help hold the user's jaw in a desired position, such as, for example, when upward force is applied to the user's mandible by a chin strap or other device.

In certain embodiments, a second moldable tray configured to engage with the user's second dental arch may be fused with moldable tray 730, locating the user's mandibular arch in a particular position relative to the user's maxillary arch. In such embodiments, the second moldable tray may be fused to moldable tray 730 prior to forming a mold of the user's dentition. In alternative embodiments, the second moldable tray may form a separate piece prior to being molded to the user's dentition. In such embodiments, the second moldable tray and moldable tray 730 may be heated and fused together during the molding process.

Alternative embodiments may utilize a custom-made tray rather than a moldable tray. In some embodiments, a custom-made tray may be pre-fitted and then molded from a substantially rigid material, such as, for example, acrylic. Certain embodiments may have two separate custom-made trays coupled together via an adjustment mechanism, such as, for example, those described in U.S. Pat. No. 7,748,386, which is incorporated herein by reference. In certain embodiments, such an adjustment mechanism may have wedges in the side that interact to move the user's lower jaw forward.

Figure 13:
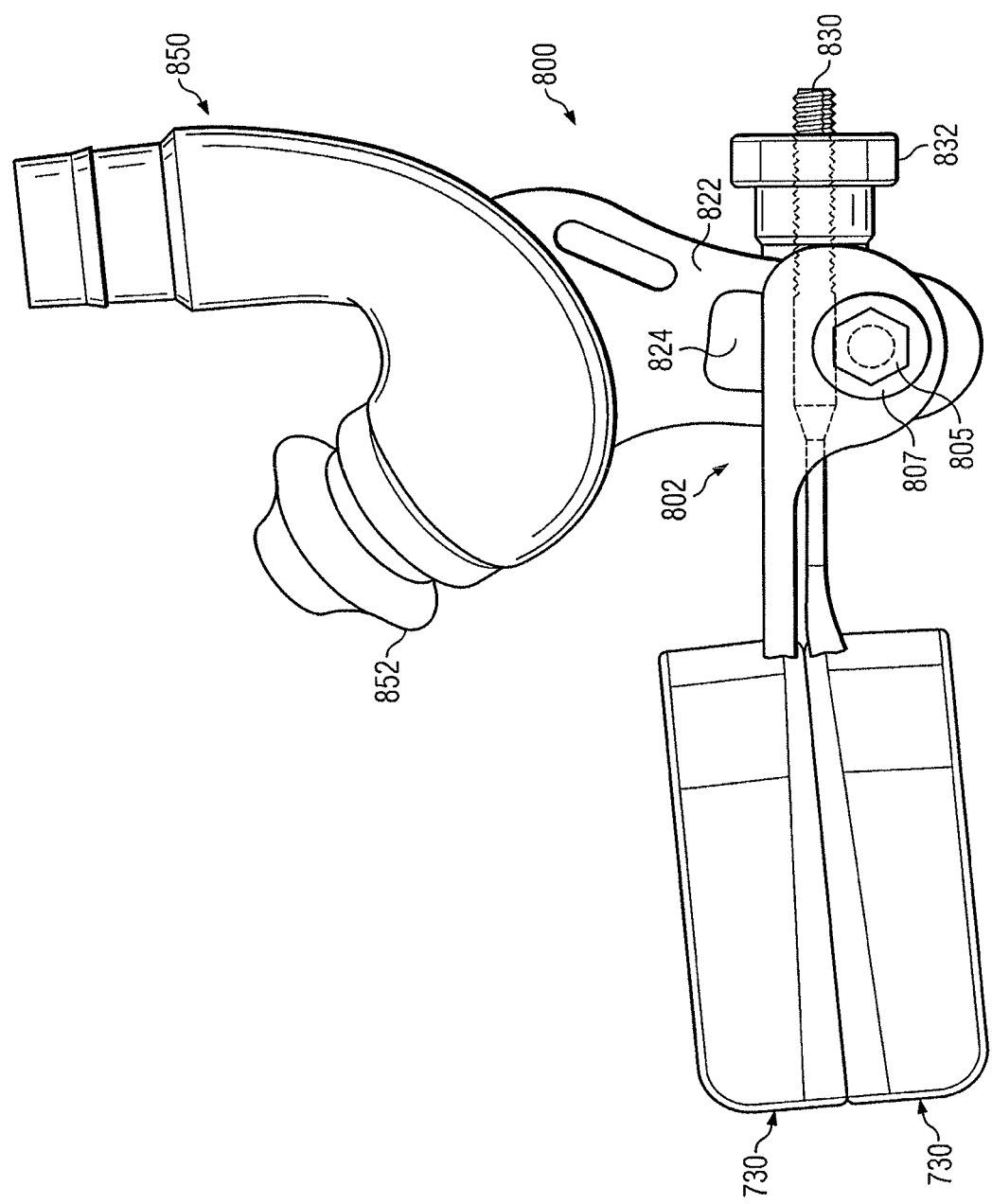
FIG. 13 illustrates example moldable trays, an example post, and an example mask.

FIG. 12 illustrates two moldable trays 730, a mask 850, and a coupler 800. FIG. 13 illustrates a side view of the components shown in FIG. 12. As shown, moldable trays 730 include occlusal surface 732, outer rim 734, and inner rim 736. Mask 850 is a device for directing the flow of air and/or other gases to a user. Coupler 800 adjustably couples mask 850 to at least one moldable tray 730. In the embodiment shown, two moldable trays 730 cooperate to form an adjustable oral appliance configured to adjustably position the lower arch of a user relative to the user's upper arch. As shown, upper moldable tray 730, includes post 802 that extends anterior to the user's mouth when upper moldable tray 730 is positioned proximate to the user's maxillary dentition. Similarly, lower moldable tray 730 includes tension element 830 that extends anterior to the user's mouth when lower moldable tray 730 is positioned proximate to the user's mandibular dentition. In this embodiment, post 802 includes a tension element channel 834 to receive tension element 830. In certain embodiments, tension element 830 may be threaded and may be coupled to adjustment knob 832, which may be turned to adjust the position of lower moldable tray 730 relative to upper moldable tray 730. Although tension element 830 is described as being threaded, other configurations may be used to adjust the relative positions of upper and lower moldable trays 730. In alternative embodiments, tension element 830 may attach to an adjustable oral appliance, such as the oral appliance described in U.S. Pat. No. 7,748,386. In certain embodiments, upper moldable tray 730 and lower moldable tray 730 may be used with or without a mask. In these embodiments, moldable trays 730 may function as an oral appliance only or may be used during surgery or post-surgery to maintain the user's airway during the administering of anaesthetics or during ventilation, or they may be in place in the event that resuscitation becomes necessary.

Mask 850 includes one or more flanges 822, with each flange 822 including a slot 824. Flange 822 may be fixed to or integrally formed with mask 850; or flange 822 may be removably coupled to mask 850. However, it should be appreciated that flange 822 may be fixed to or integrally formed with other mask types, or flange 822 may be removably coupled to and/or interchangeable with other mask types. In embodiments in which a single flange 822 is used, flange 822 may have a thickness of between 10-22 millimeters, though such dimensions are not required. In other embodiments, flange 822 may have a thickness of between 12-18 millimeters. In a particular embodiment, flange 822 may have a thickness of approximately 14 millimeters. In embodiments having multiple flanges 822, each flange 822 may have a thickness of between 1-4 millimeters, though this range is not required. In a particular embodiment having a multiple flanges 822, one or more of the flanges 822 may have a thickness of approximately 3 millimeters. In certain embodiments having multiple flanges 822, when the mask is oriented to the user's face, the distance between the right edge of the rightmost flange 822 and the left edge of the leftmost flange 822 may be similar to the ranges described above for a single flange 822. For example, in a particular embodiment having two flanges 822, the span between the inner edges of the flanges may be approximately 6 millimeters and the span between the outer edges of the flanges may be approximately 14 millimeters, though other dimensions may be used. Such embodiments may improve the ability of coupler 800 to prevent deformation outside of the sagittal plane.

As shown in FIG. 12, mask 850 is a pillow mask with nasal inserts 852 that may be configured to seal against the user's nostrils. In certain embodiments, nasal inserts 852 may be fitted independently to mask 850 and may be capable of rotating independently to the angle of the user's nostrils. In certain embodiments, nasal inserts 852 may be removeably coupled to mask 850 and may be interchangeable with different sizes of nasal inserts 852. In some embodiments, the user may select different sizes of nasal inserts 852 for each nostril. In alternative embodiments, nasal inserts 852 may be formed together as a pair and attached as one unit to mask 850. In other embodiments, nasal inserts 852 may be fixed permanently to mask 850. In certain embodiments, mask 850 may have an inlet that is fixed on the top of the frame for delivering air and/or other gases to mask 850. In some embodiments, mask 850 may have a ball joint, elbow, or a combination thereof delivering air and/or other gases to mask 850. In alternative embodiments, air and/or other gases may be delivered in the side or the bottom of mask 850. In certain embodiments, air and/or other gases may be delivered through several different tubes. In certain embodiments, the user may be able to select one or more connection points for delivery of air and/or other gases and plug or otherwise disable other connection points. In other embodiments, a main hose may attach directly to mask 850 or to an elbow joint or a ball joint. In certain embodiments, mask 850 may have a length of flexible tubing that may connect with a main hose. In certain embodiments, the optional flexible tubing may be approximately 50-300 millimeters long, though this is not required. In one example embodiment, mask 850 may have a 250 millimeter-long flexible tube. In certain embodiments, such tubing may be light, flexible, and have a smaller diameter than the main hose. In some embodiments, the flexible tubing may have a diameter of approximately 12-19 millimeters, while the main hose may have a diameter of approximately 22 millimeters, though these dimensions are not required. In one example embodiment, the flexible tubing may have an internal diameter of approximately 17 millimeters. In certain embodiments, there may be a connector between the short flexible tube and the main tube, and in some embodiments this connector may be capable of swiveling. In particular embodiments, the connector may be a ball joint or a straight connector. In certain embodiments, optional headgear may be supplied that attaches to mask 850, coupler 800, and/or moldable tray 730. Such headgear may pass along the side of the user's face and may be capable of holding the main hose or other air-delivery device in a particular position. For example, in certain embodiments, such headgear may hold the main hose in place on top of the user's head or to one or both sides of the user's head. In certain embodiments, such headgear may also be configured to help hold moldable tray 730, or any other oral appliance, in the user's mouth. In some embodiments, such headgear may be adjustable at a connection point on mask 850 and/or at one or more places around the user's head. In alternative embodiments, the headgear may be formed from a stretchable material and may require little or no manual adjustment. In one example embodiment, the headgear may be at least partially made from Breath-o-Prene®, which is a soft, breathable laminate. In another example embodiment, the headgear may be at least partially made from silicone or a molded thermoplastic/fabric composite. In other embodiments, the headgear may be formed from a combination of these materials, or from a combination of these and other materials. In certain embodiments, a chin strap may attach to mask 850, headgear, or moldable tray 730 or any other oral appliance. In some embodiments, mask 850 may have bias flow (vent holes) to flush out the user's exhaled breath. In such embodiments, mask 850 may have a plurality of holes to enable bias flow. In certain embodiments, mask 850 may have approximately 10-50 holes, though this is not required. In one example embodiment, mask 850 may have approximately 35 holes. In these embodiments, the holes may be approximately 0.75 millimeters in diameter, though these dimensions are not required. In certain embodiments, the holes may have non-uniform cross-sectional shapes throughout the length of the holes. In one example embodiment, one or more of the holes may be rounded and have an opening diameter of approximately 1.2 millimeters, the diameter of the hole falling to approximately 0.75 millimeters when moving through the hole and then expanding again to a diameter greater than 0.75 millimeters when moving through to the other end of the hole. In alternative embodiments, the holes may be tapered from one side or the other, or the holes may be straight throughout. In certain embodiments, having many small holes may slow the flow of gas and may reduce the draft and noise of such flow. In other embodiments, mask 850 may have no holes, which may enable closed-loop ventilation. In certain embodiments, mask 850 may be first formed in two or more distinct pieces and then joined, for example, by welding, gluing, clipping, screwing, latching, strapping, or otherwise fixing the pieces together. In other embodiments, the mask may initially be formed as a single piece. Furthermore, those skilled in the art will appreciate that the headgear, tubes, bias holes, chin straps, attachments, assembly features, and other aspects described above may also apply to other masks described herein.

Post 802 may include one or more channels 806 and a slot 804. In the embodiment shown, coupler 800 is formed by two flanges 822 engaging two channels 806. The movement of flanges 822 relative to channels 806 is limited by fastener 805 in slot 804. Fastener 805 may represent any structure that can restrict the movement of flanges 822 relative to channels 806. In certain embodiments, fastener 805 may be a pin, screw, or bolt. In the embodiment shown, fastener 805 is a threaded hex-head bolt that engages a hex-head counter sink 807 on one side of post 802 and a tightening knob 808 on the other side of post 802. In certain embodiments, a hex-head (or other appropriately shaped) countersink may prevent rotation of fastener 805 while tightening knob 808 or other appropriate structure is fixing the position of fastener 805. In a particular embodiment, both sides of post 802 may include a countersink, such that a user may select to position tightening knob 808 on either side of post 802. This flexibility may make the use of tightening knob 808 equally convenient to left-handed and right-handed users. In alternative embodiments, post 802 may include an additional tightening knob opposite tightening knob 808, enabling adjustment from either side of post 802.

FIG. 14A illustrates the anterior end of an example post 802 and FIG. 14B illustrates an example anterior view of an example arched frame 700 with a tension element 830. As shown in FIG. 14B, in certain embodiments at least a portion of the tension element may be threaded, and the threaded portion may engage with the tension element adjustor 832. In the embodiments shown, post 802 includes D-shaped slot 834 and tension element 830 has a corresponding D-shaped cross-section. In certain embodiments, the D-shaped slot 834 and tension element 830 may substantially prevent tension element 830 from rotating when adjustment knob 832 is used to adjust tension element 830. Although a D-shape is illustrated, other cross-sections may be used to prevent the rotation of tension element 830 in slot 834. As one example, slot 834 may have a "key" structure that corresponds with a channel in tension element 830.

Figure 15A:
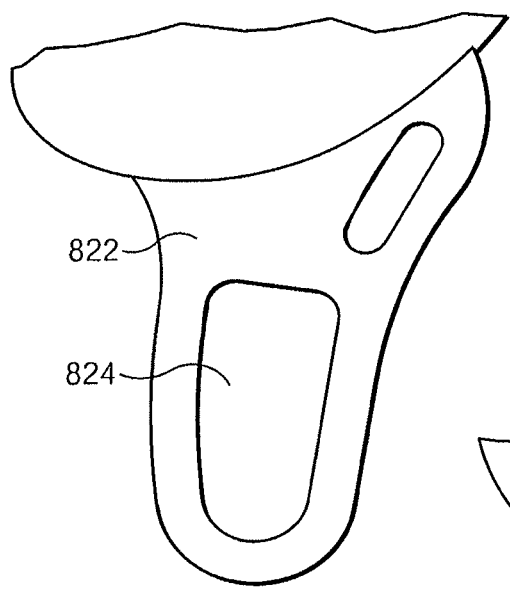
FIGS. 15A and 15B illustrate example flanges.
Figure 15B:
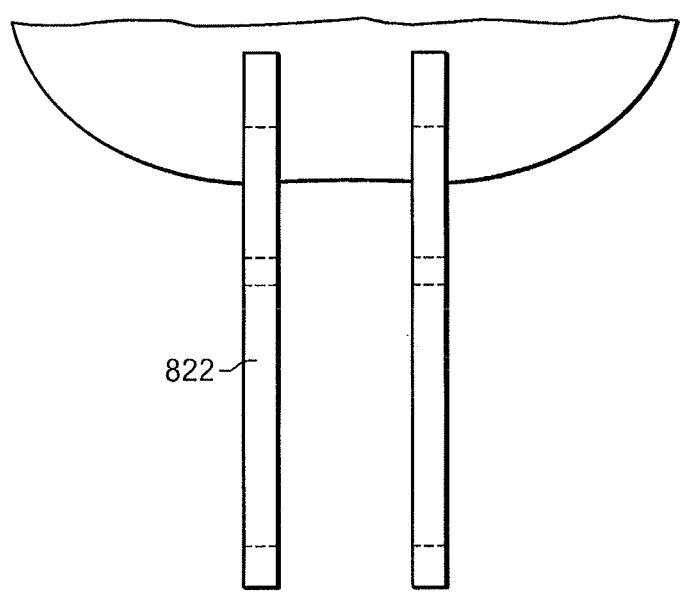

FIGS. 15A and 15B illustrate example flanges 822. As shown in FIG. 15A, flange 822 may include a slot 824. While FIG. 15B depicts two distinct flanges 822, alternative embodiments may have a single flange, multiple flanges, or any other structure which may be secured in place relative to post 802 by fastener 805. In alternative embodiments, slot 824 may have various shapes, sizes, and orientations. In certain embodiments, flanges 822 may be formed and/or molded as one part. In other embodiments, flanges 822 may be formed from multiple parts that may be assembled, clipped, screwed, or overmolded. In various embodiments, flanges 822 may consist of plastic and/or metal such as stainless steel.

Figure 16A:
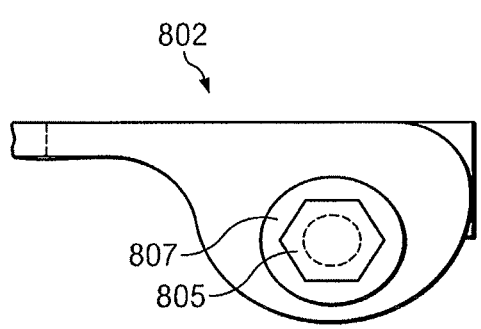
FIGS. 16A and 16B illustrate an example post.
Figure 16B:
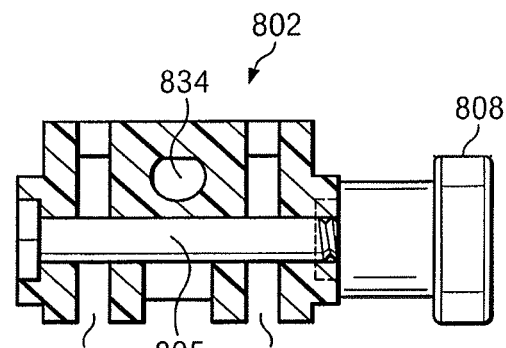

FIGS. 16A and 16B illustrate an example post 802 having a fastener 805, channels 806, countersink 807, tightening knob 808, and a tension element channel 834. As shown in FIG. 16A, an end of fastener 805 may be configured to engage with countersink 807. In certain embodiments, as shown in FIG. 16B, at least a portion of fastener 805 may be threaded. As shown in FIG. 16B, in some embodiments slot 804 (not shown) may cross laterally through post 802, allowing fastener 805 to pass laterally through post 802 across channels 806. In some embodiments, when flanges 822 are disposed in channel 806, slots 824 may substantially align with slot 804, allowing fastener 805 to pass through both slot 804 and slots 824. In such an embodiment, tightening knob 808 may be adjusted to increase or decrease lateral force exerted along the long axis of fastener 808. Adjusting tightening knob 808 in such an embodiment may operate to secure flanges 822 in place relative to post 802. In certain embodiments, an attached mask or breathing device may be moved into the desired position relative to the user's face and then fixed into that position by adjusting tightening knob 808.

In certain embodiments, post 802 may be formed and/or molded as one part. In other embodiments, post 802 may be formed from multiple parts that may be assembled, clipped, screwed, or overmolded. In various embodiments, post 802 may consist of plastic and/or metal such as stainless steel.

Figure 17A:
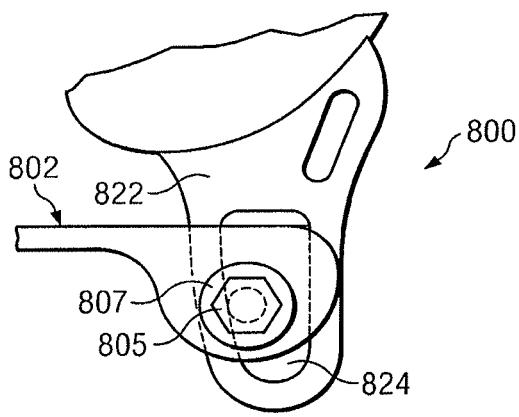
FIGS. 17A through 17F illustrate example flanges engaged with an example post.
Figure 17B:
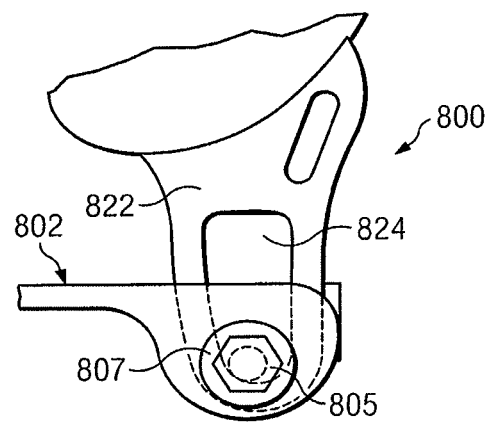
Figure 17C:
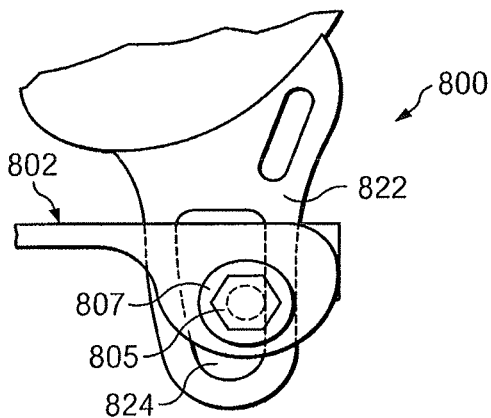
Figure 17D:
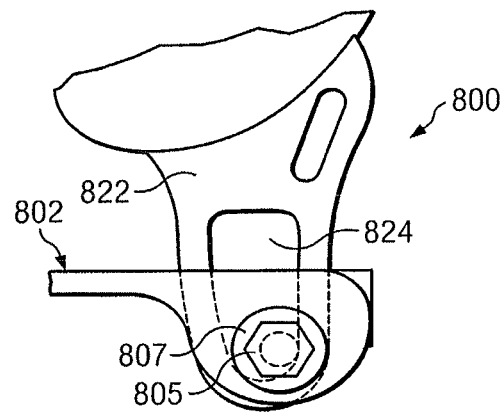
Figure 17E:
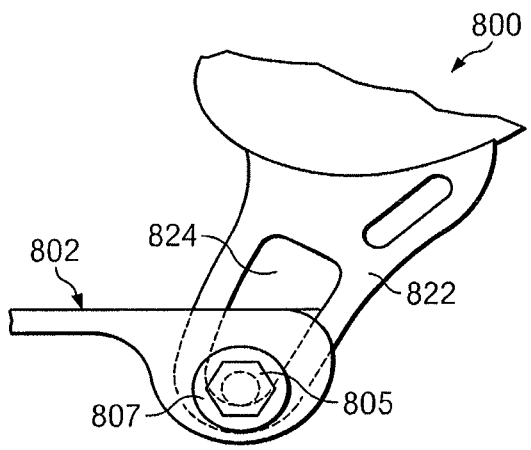
Figure 17F:
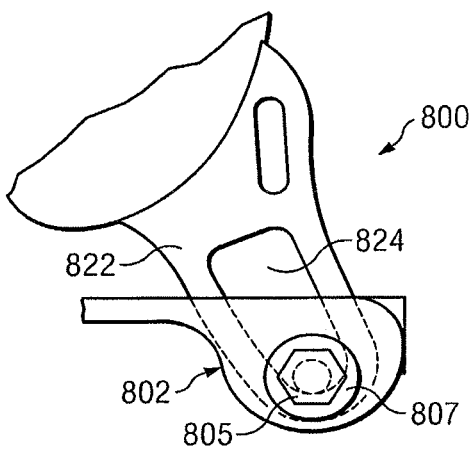

FIGS. 17A through 17F illustrate various positions of an example coupler 800. As shown in FIG. 17A, coupler 800 may include a flange 822 with slot 824 and a post 802 having a fastener 805 and countersink 807. As shown in FIGS. 17A through 17F, in certain embodiments, flange 822 may be capable of moving in the superior-inferior direction relative to post 802, moving in the anterior-posterior direction relative to post 802, and rotating around fastener 805. In alternative embodiments, flange 822 may be capable of moving in the superior-inferior direction relative to post 802 and rotating around fastener 805. In certain embodiments, flange 822 may be limited to adjustment, rotation, and/or movement within the sagittal plane. In some embodiments, post 802 may include an additional joint that may provide adjustment, rotation, and/or movement in one or more additional directions. In certain embodiments, flange 822 may be adjusted vertically approximately +/−10 mm, though other ranges may be used. For example, other embodiments may have vertical adjustment ranges of between +/−7 mm and +/−14 mm. In certain embodiments, flange 822 may be adjusted in the anterior-posterior direction approximately +/−5 mm, though other ranges may be used. For example, other embodiments may have horizontal adjustment ranges of between +/−3 mm and +/−8 mm. In certain embodiments, when flange 822 has a desired position and orientation, tightening knob 808 may be adjusted to secure flange 822 in place relative to post 802.

Figure 18:
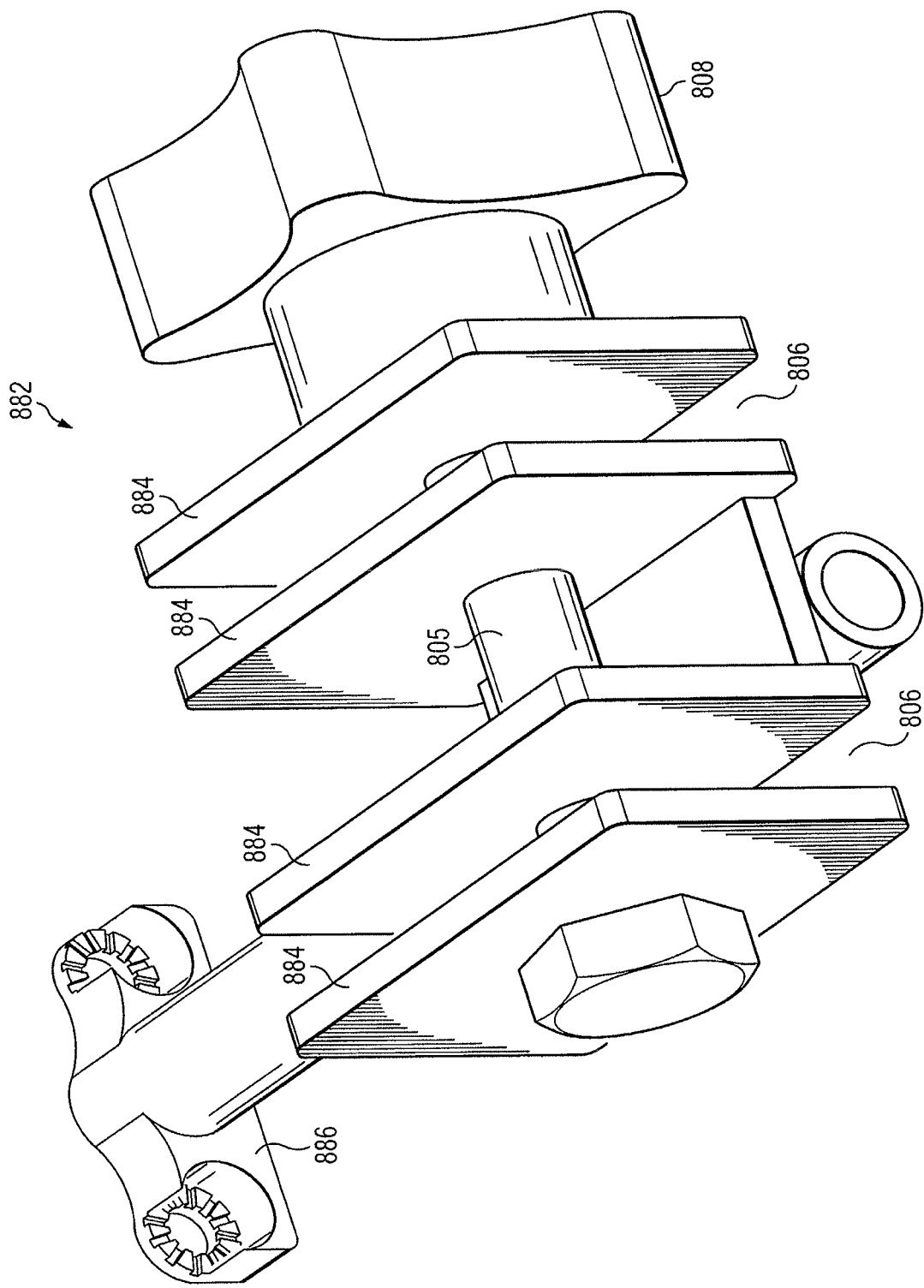
FIG. 18 illustrates an example post.

FIG. 18 illustrates another example post 882 having a fastener 805, plates 884, channels 806, tightening knob 808, and plate 886. In particular embodiments, plates 884 may define channels 806, which are configured to receive flanges 822. As shown in FIG. 18, post 882 may be cylindrical and hollow. In a particular embodiment, post 882 may consist of metal, such as stainless steal. In alternative embodiments, post 882 may have various structures, shapes, and densities and can be made from a wide variety of rigid materials. In some embodiments, plate 886 may be attached at the posterior end of post 882. Plate 886 may be configured to couple to the front of an oral appliance such as those described, for example, in U.S. Pat. No. 7,748,386, which is incorporated herein by reference.

Figure 19A:
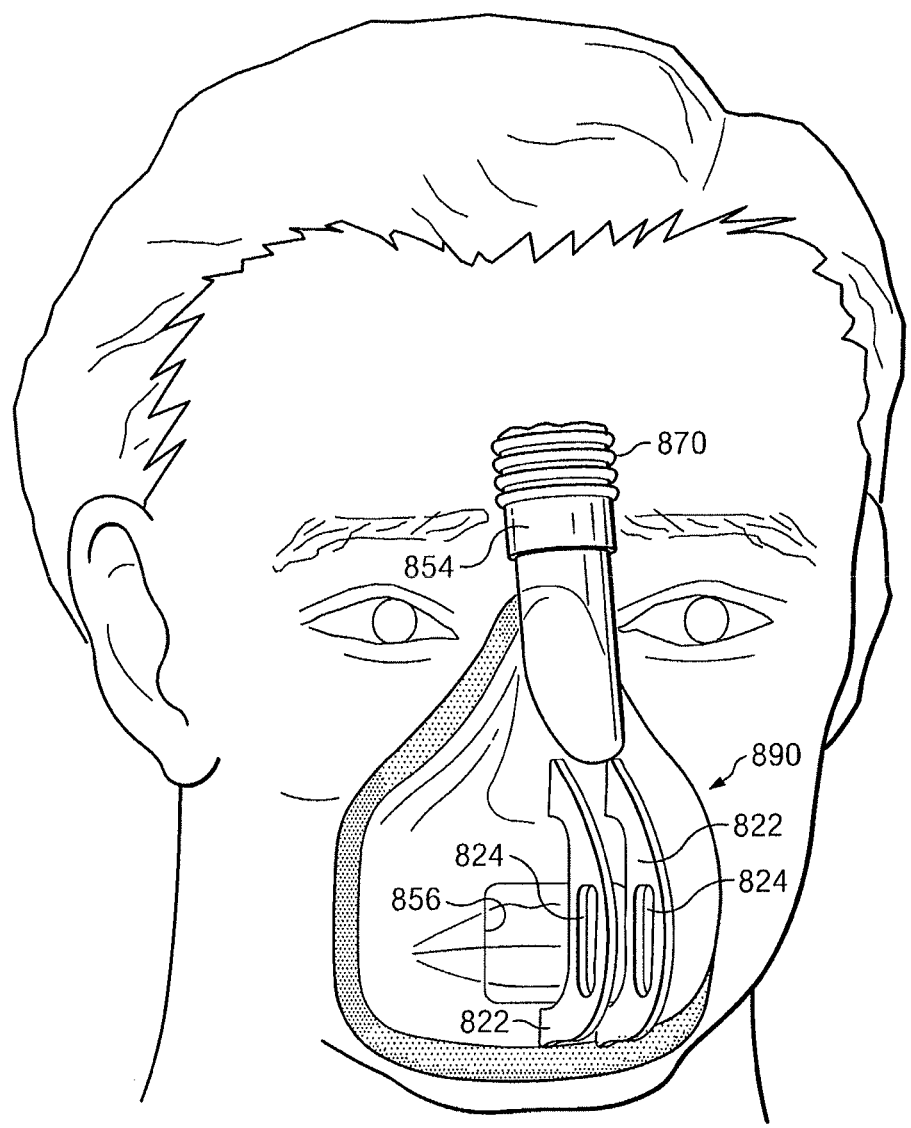
FIGS. 19A and 19B illustrate an example mask.
Figure 19B:
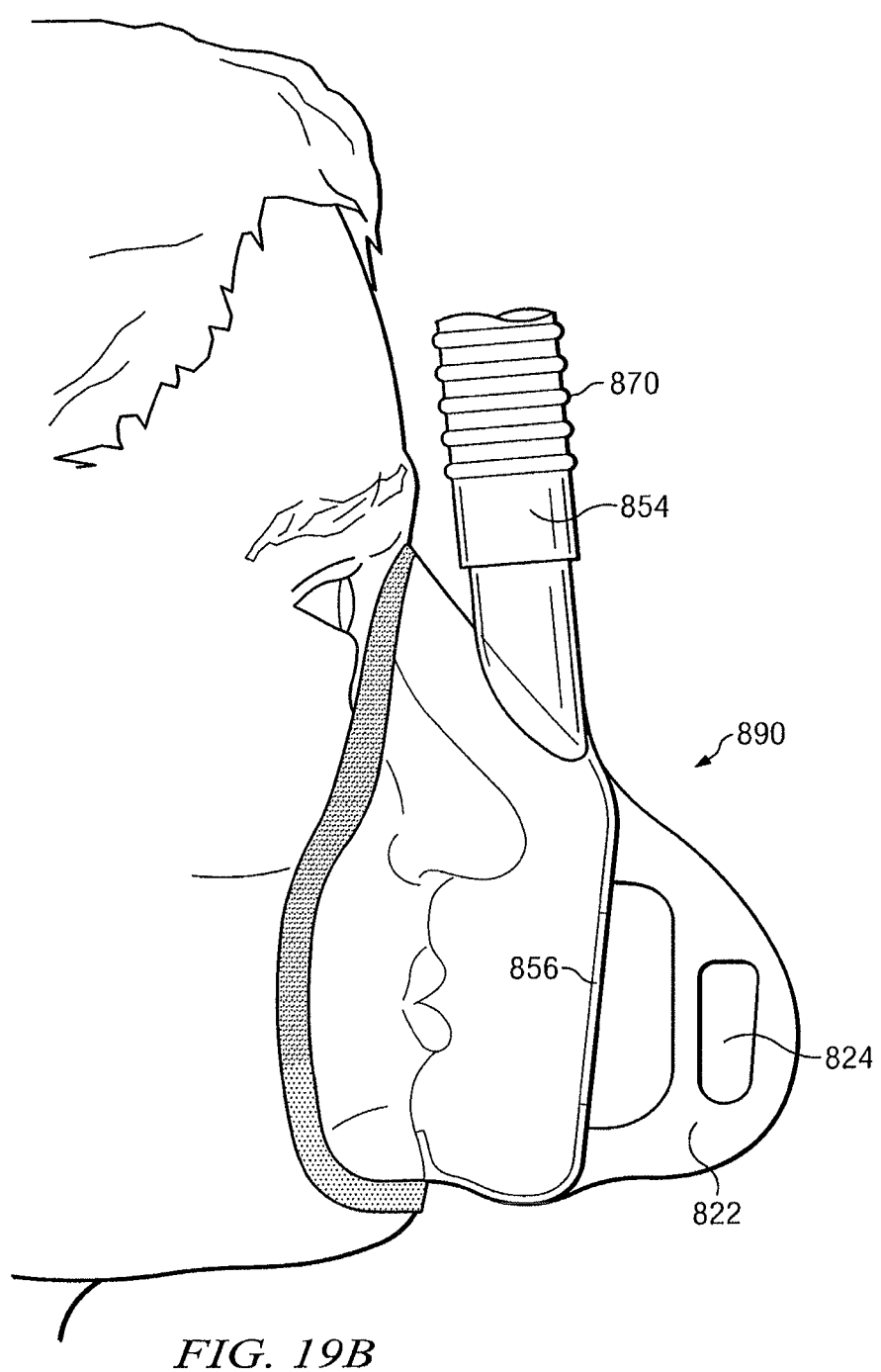

FIG. 19A illustrates an example mask 890 having flanges 822 with slots 824 and a hose coupler 854 coupled to a hose 870. FIG. 19B illustrates a side view of mask 890, showing opening 856 and flanges 822. In certain embodiments, as shown in FIG. 19B, flanges 822 may be fixed to or integrally formed with mask 890. In alternative embodiments, flanges 822 may be removably coupled to the anterior surface of mask 890. In some embodiments, opening 856 may allow structures, such as post 802 or post 882, to pass through the front of mask 890 and couple with flanges 824. In certain embodiments, opening 856 may be sized to accommodate various positions and orientations of post 802 relative to mask 890.

Figure 20:
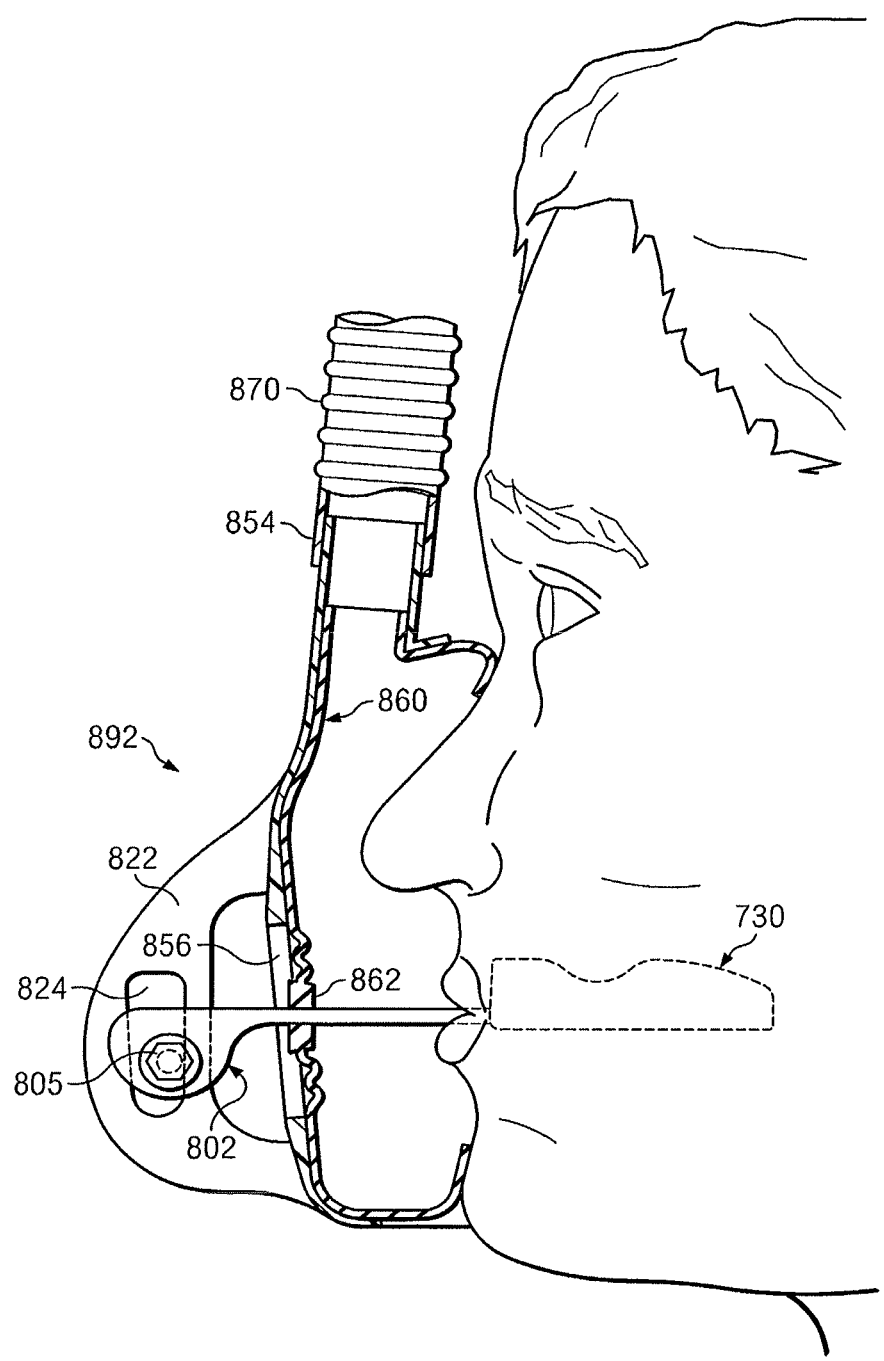
FIG. 20 illustrates an example mask, post, and oral appliance.

FIG. 20 illustrates an example mask 892 coupled to an example post 802. As shown, mask 892 includes a seal 860, opening 856, flanges 822, and a hose coupler 854. As shown, post 802 is attached to moldable tray 730 inside the user's mouth, allowing mask 892 to be adjustably oriented to the user's face. In certain embodiments, mask 892 may be adjusted vertically, adjusted in the anterior-posterior direction, and/or rotated in the sagittal plane. In certain embodiments, as shown in FIG. 20, seal 860 may include flexible gasket 862 which may be configured to allow post 802 to pass through it and couple with flanges 824, forming an air-tight seal around post 802. Flexible gasket 862 may also allow mask 892 to be adjusted to various positions and orientations relative to the user's face without significantly disturbing post 802 or breaking the airtight seal of seal 860. In some embodiments, as shown in FIG. 20, flexible gasket 862 may incorporate or be surrounded by creases, which may improve the ability of flexible gasket 862 to accommodate various positions of post 802, though such creases are not required. In certain embodiments, post 802, or another suitable post such as post 882, may attach to various oral appliances, allowing for various combinations of oral appliances, posts, and masks. In alternative embodiments, flanges 822 may be contained within a mask, providing the substantially similar movement and adjustment to mask 892. In such embodiments, fastener 805 may pass through a gasket in the mask's seal to a position outside the mask where it could be operated by a user.

Having mask 892 secured to the user's oral appliance may obviate the need for the user to wear stabilizing headgear. Such straps may shift accidentally, may be uncomfortable for the user, may leave marks on the user's face, and may irritate the user's face and scalp. Furthermore, since having mask 892 secured to the user's oral appliance may prevent substantial movement of mask 892 relative to the user's face and prevent leakage, these embodiments may reduce the need to tighten the mask to the user's face, which may result in reduced pressure on the user's face and reduced pressure sores. These embodiments may also provide greater mask stability during sleep for users who exhibit substantial movement during sleep. It should be appreciated that all such embodiments and advantages described with respect to mask 892 may also apply to other mask described herein, such as, for example, masks 850 and/or 894.

In alternative embodiments, mask 892 may be held in place by a tension element attached to an oral appliance, with the tension element pulling mask 892 toward the oral appliance and the user's face. In certain embodiments, the pull of the tension element may be adjusted by a screw, tightening knob, or other adjustment mechanism. Following adjustment, in certain embodiments mask 892 may be secured via a fastener, such as a hook.

Figure 21A:
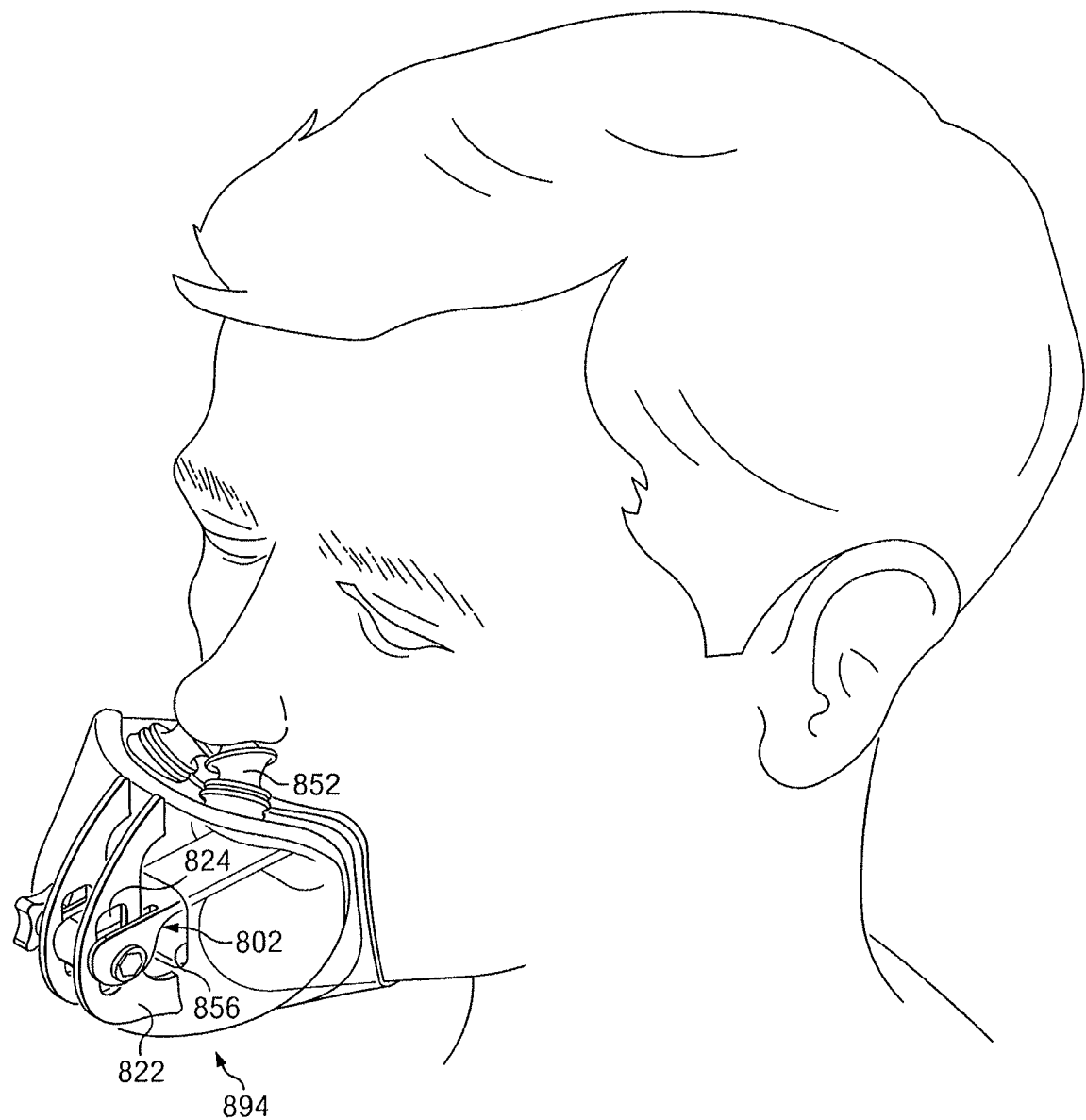
FIG. 21A illustrates an example mask and post.
Figure 21B:
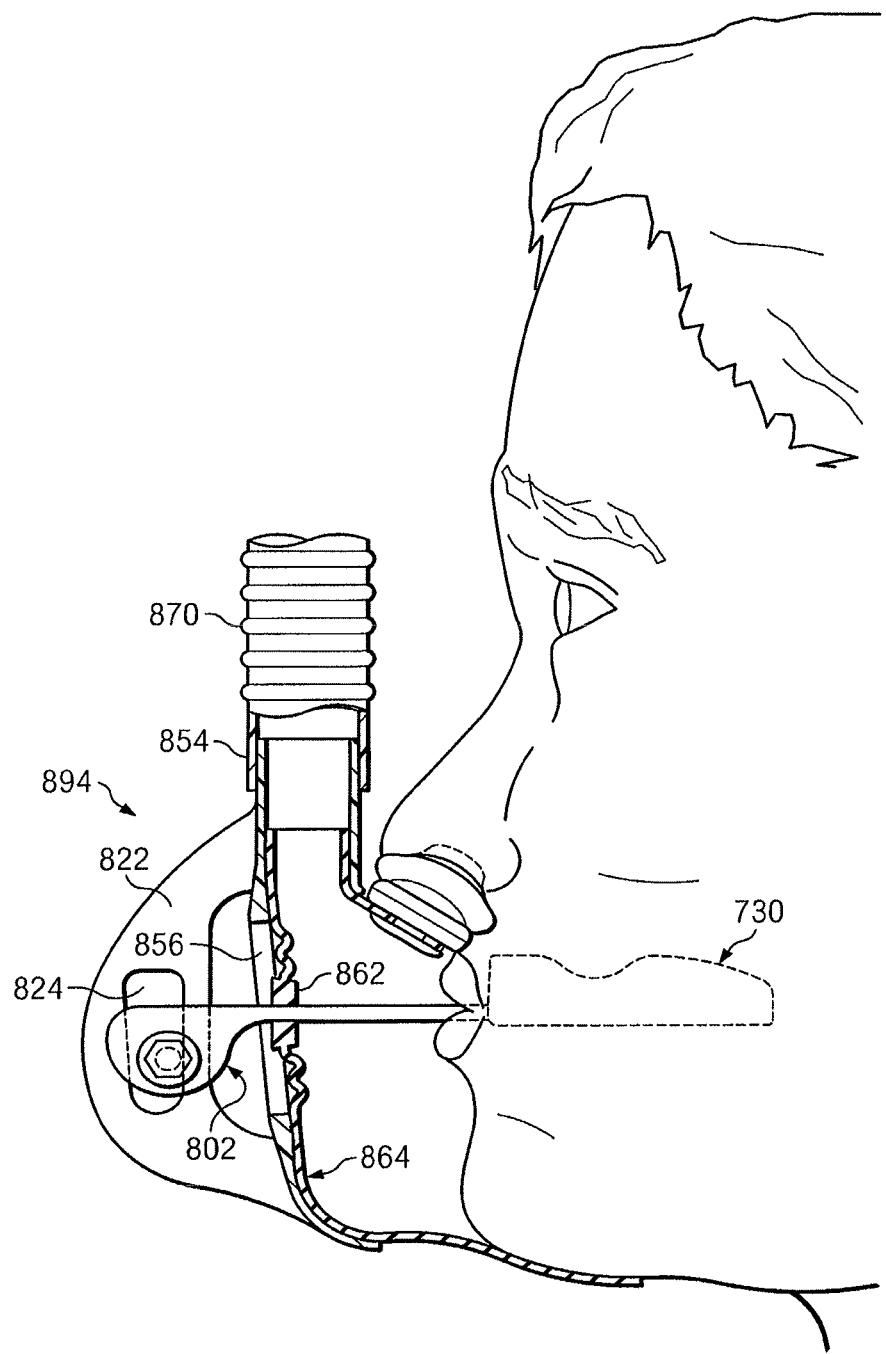
FIG. 21B illustrates an example mask, post, and oral appliance.

While FIG. 20 shows mask 892 as a full face mask covering the user's nose and mouth, FIGS. 21A and 21B illustrate an alternative mask 894 covering the user's mouth and delivering air and/or other gases to the user's nose via nasal inserts 852. In certain embodiments, as shown in FIG. 21B, seal 860 may extend below the user's chin. Masks with portions that extend below a user's chin may improve the function of the mask by preventing and/or reducing the occurrence of the user opening their mouth while using the mask. Still other embodiments incorporating different types of masks will be apparent to those skilled in the art. In certain embodiments, when flanges 822 of mask 894 are disposed in channels 806 of post 802, movement of mask 894 outside of the sagittal plane is strongly resisted, which may help prevent mask leakage if a user lays on his or her side, pushing mask 894 laterally against a surface such as a pillow.

Various types of masks may be used in other embodiments. For example, certain embodiments may use pillow masks, which seal against the user's nostrils; nasal masks, which cover the user's nose; full face masks, which cover both the user's mouth and nose; hybrid masks, which have one portion covering a user's mouth and another portion covering the user's nose or sealing against the user's nostrils; or oral masks, which cover the user's mouth. Such masks may be used for the delivery of pressurized air, oxygen, aerosols, gasses, or medication; and the masks may be vented or non-vented. Masks included in various embodiments may be used for continuous positive airway pressure treatment (CPAP), auto-CPAP, or bilevel or closed-loop ventilation; and masks may be custom-fitted to a particular user or they may be non-custom masks that conform to different face shapes.

In certain embodiments, a venting seal may be combined with the masks and/or oral appliances disclosed herein. In certain embodiments, the venting seal may be fixed or detachable. The venting seal may be positioned outside the user's mouth next to the user's lips or the venting seal may be positioned behind the user's lips next to the user's teeth. In certain embodiments, the venting seal may reduce or eliminate the venting of air or other gases from the user's mouth, such as for example when air or other gases are being supplied to the user's nose. An example venting seal is disclosed in U.S. Pat. No. 6,675,802, incorporated herein by reference. In certain embodiments, the venting seal may be attached to post 802, post 882, or other appropriate structure, either removably or permanently.

Figure 22A:
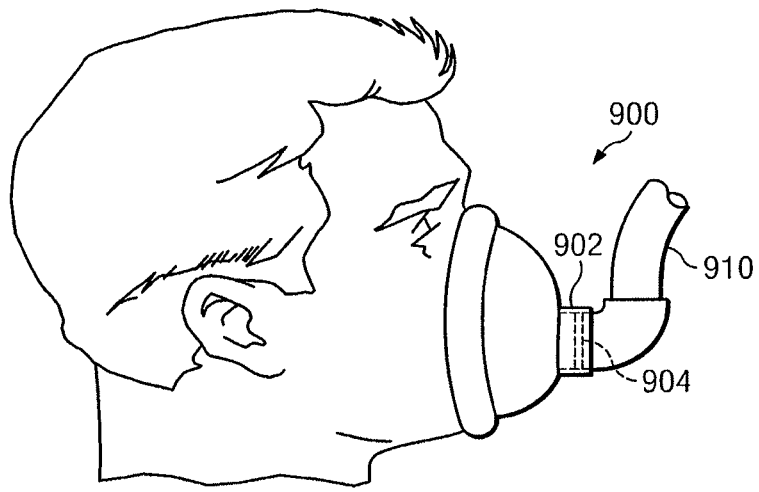
FIG. 22A illustrates an example mask including a strap.
Figure 22B:
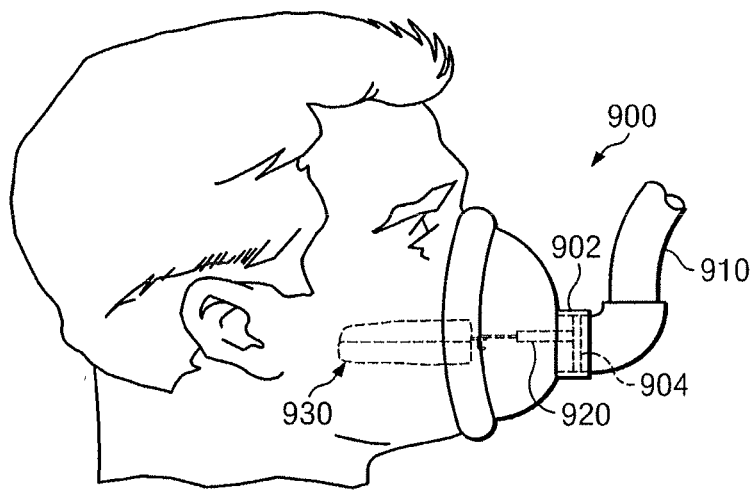
FIG. 22B illustrates an example tension element, oral appliance, and mask.
Figure 23A:
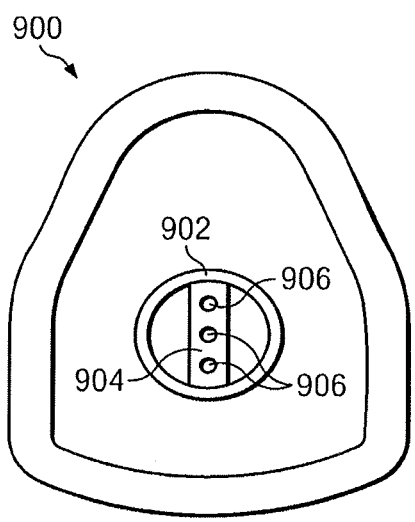
FIGS. 23A and 23B illustrate an example mask comprising a strap.
Figure 23B:
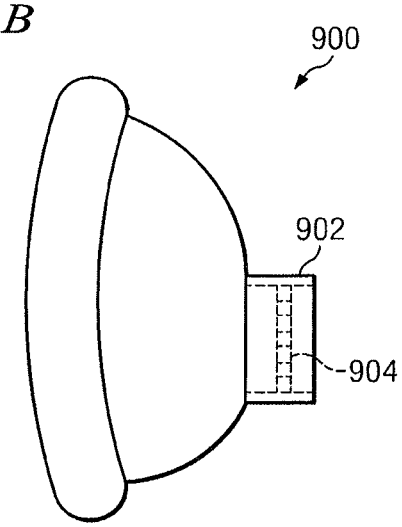
Figure 24:
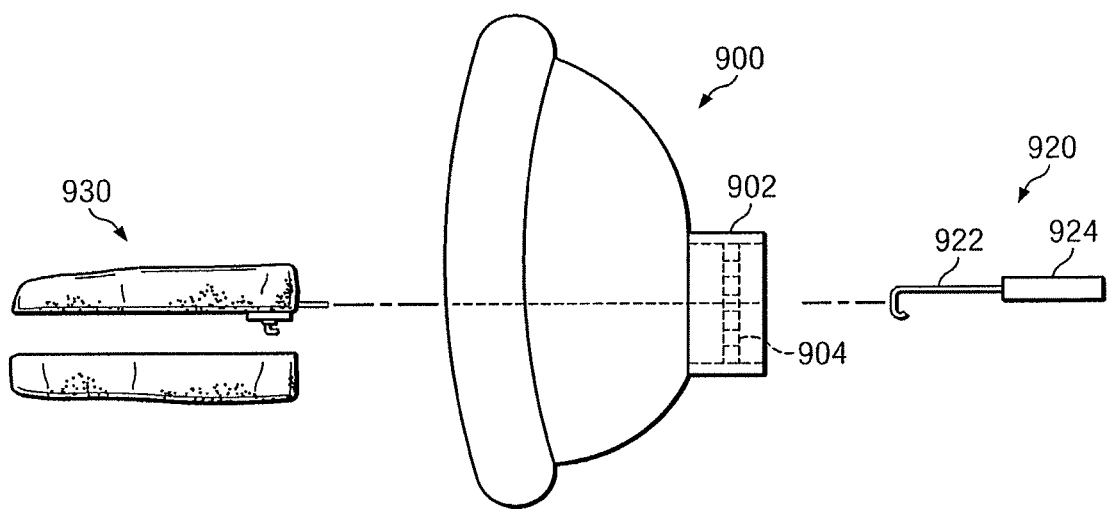
FIG. 24 illustrates an example tension element, oral appliance, and mask.

FIGS. 22A and 22B and FIG. 23 illustrate an example mask 900 having a hose coupler 902 and a strap 904 with a plurality of apertures 906. As shown in FIG. 22A, hose coupler 902 may be configured to attach to a hose 910 which may deliver air and/or other gases to mask 900. In certain embodiments, as shown in FIG. 23A, strap 904 may span the opening of hose coupler 902. As shown in FIG. 23A, strap 904 may have a plurality of apertures along its length. In certain embodiments, as shown in FIG. 22B, a tension element 920 may pass through one of the plurality of apertures 906 and attach to oral appliance 930, which may be any mouthpiece configured to couple to tension element 920. FIG. 24 illustrates an example oral appliance 930, mask 900, and tension element 920. As shown in FIG. 24, tension element 920 has a threaded knob 924 and a hook 922. Oral appliance 930 includes a receiver to engage tension element 920 to pull mask 900 towards oral appliance 930. In certain embodiments, the receiver in oral appliance 930 may be a loop, a latch, or a slot. In a particular embodiment, tension element 920 includes hook 922 and threaded knob 924. In alternative embodiments, tension element 920 may include one or more alternative structures to pull mask 900 towards oral appliance 930.

Figure 25A:
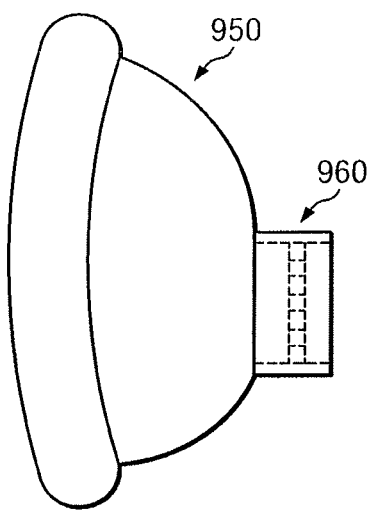
FIGS. 25A and 25B illustrate an example mask and adapter.
Figure 25B:
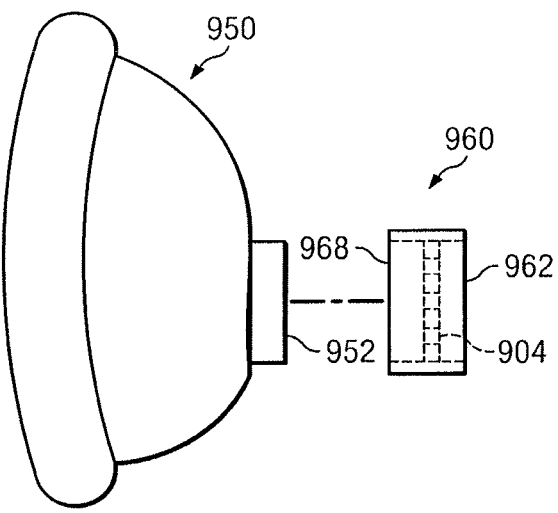
Figure 26A:
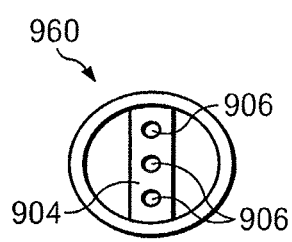
FIGS. 26A and 26B illustrate an example adapter.
Figure 26B:
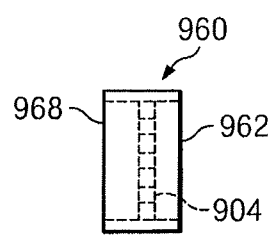

FIGS. 25A and 25B illustrate an example mask 950 and adapter 960. As shown in FIGS. 26A and 26B, in certain embodiments adapter 960 may include a hose coupler 962, a strap 904 having a plurality of apertures 906, and a mask coupler 968. In some embodiments, hose coupler 902 may be configured to couple with a hose 910. As shown in FIGS. 25A and 25B, mask coupler 968 may be configured to couple with hose coupler 952 of mask 950, allowing adapter 960 to couple with mask 950. When adapter 960 is coupled to mask 950, adapter 960 may allow mask 950 to interact with hose 910 and tension element 920 as described in the above description of mask 900.

Figure 27:
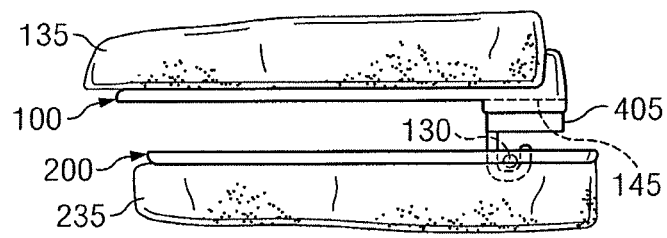
FIG. 27 illustrates an example dental device comprising a universal coupler and an example dental attachment.

FIG. 27 illustrates an example dental device comprising a universal coupler and an example dental attachment. As shown in FIG. 27, a dental device is provided comprising an arched frame 100, a moldable tray 135, a second arched frame 200, and a second moldable tray 235. Arched frame 100 may comprise a universal coupler comprising a substantially planar surface 145. In particular embodiments, a hook 405 may be configured to engage the universal coupler. In particular embodiments, second arched frame 200 may comprise a receiving mechanism 130 coupled to the lingual portion of second arched frame 200. Receiving mechanism 130 may be a bar that spans the lingual portion of second arched frame 200. In particular embodiments, hook 405 may engage receiving mechanism 130 to adjust the forward position of arched frame 100 relative to second arched frame 200. In certain embodiments, this adjustment may help to prevent a user from snoring when the dental device is inserted in the user's mouth.

Figure 28:
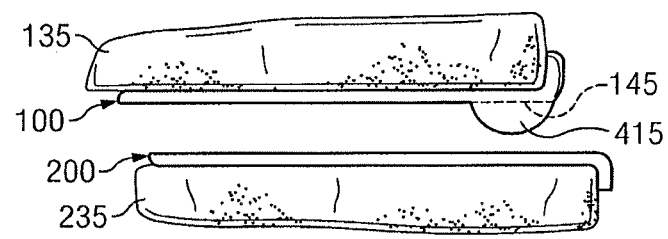
FIG. 28 illustrates an example dental device comprising a universal coupler and an example dental attachment.

FIG. 28 illustrates an example dental device comprising a universal coupler and an example dental attachment. As shown in FIG. 28, a dental device is provided comprising an arched frame 100, a moldable tray 135, a second arched frame 200, and a second moldable tray 235. Arched frame 100 may comprise a universal coupler comprising a substantially planar surface 145. In particular embodiments, a substantially rounded projection 415 may be configured to engage the universal coupler. In particular embodiments, rounded projection 415 may be the only point of contact between the user's upper and lower dental arches to prevent a user from clenching his jaw when the dental device is inserted in the user's mouth. In particular embodiments, rounded projection 415 may contact an opposing arch or may contact one or more incisors of the opposing dental arch to prevent a user from clenching his jaw when the dental device is inserted in the user's mouth. The opposing arch may have a contact surface that may be planar.

The universal oral appliance comprising a universal coupler may provide several advantages for a user. In particular embodiments, a universal oral appliance comprising a universal coupler may offer more use options to a user. For example, a user's appliance may be fitted with several different dental attachment options. The user may choose which dental attachment is best suited for his situation without having to hire a lab to construct another appliance. In particular embodiments, a particular user may also adjust the dental attachment to better suit the shape and size of the user's mouth. This disclosure contemplates the universal oral appliance being created from parts in a kit. A user may purchase the kit instead of a dental device created in a laboratory.

Figure 29:
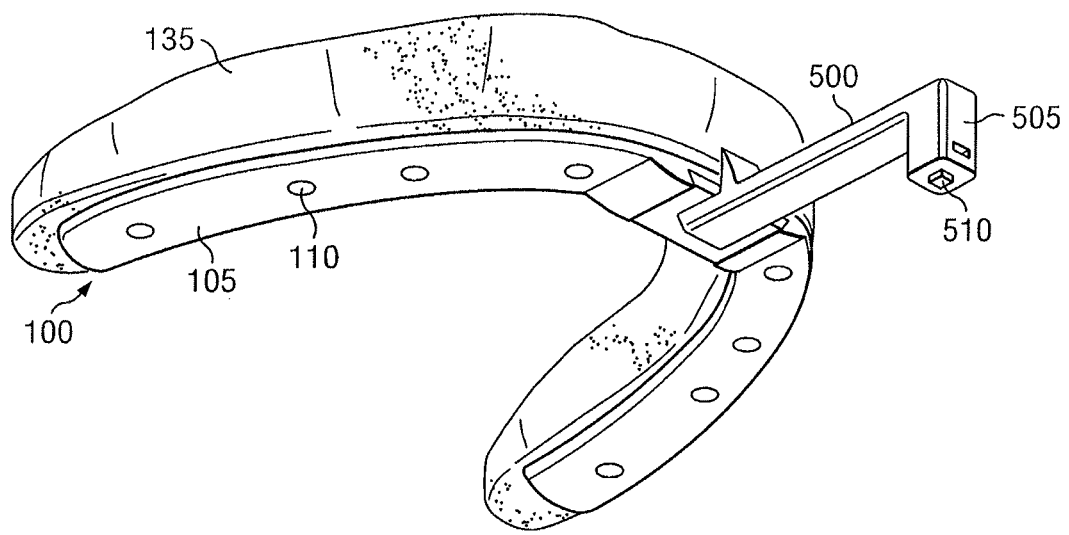
FIG. 29 illustrates an example arch comprising a dental attachment.

FIG. 29 illustrates an example arch comprising a dental attachment. As shown in FIG. 29, an arch is provided that comprises an arched frame 100 and a moldable tray 135 coupled to arched frame 100. Arched frame 100 comprises an arched body 105 that defines a plurality of apertures 110. The arch may further comprise a dental attachment configured to engage arched frame 100. In particular embodiments, the dental attachment is configured to engage arched frame 100 along the midline of arched frame 100. In particular embodiments, the dental attachment may comprise a post 500 and an anchoring element 505. Post 500 may be coupled at a first end to anchoring element 505. In particular embodiments, a second end of post 500 may engage arched frame 100. In some embodiments, post 500 may be configured to removably engage arched frame 100. In particular embodiments, anchoring element 505 may include a buckle, a slot, a clasp, a clamp, and/or any other appropriate element to anchor a tension element. In some embodiments, anchoring element 505 may be configured to be outside a user's mouth when the arch is inserted in the user's mouth. In some embodiments, the dental attachment may further comprise a release mechanism 510. As an example and not by way of limitation, release mechanism 510 may be a button or a latch. Although this disclosure describes certain types of release mechanisms 510, this disclosure contemplates any suitable release mechanism 510. Although this disclosure describes an arch comprising arched frame 100, moldable tray 135, and a dental attachment, this disclosure contemplates a one-piece arch comprising a dental attachment.

Figure 30:
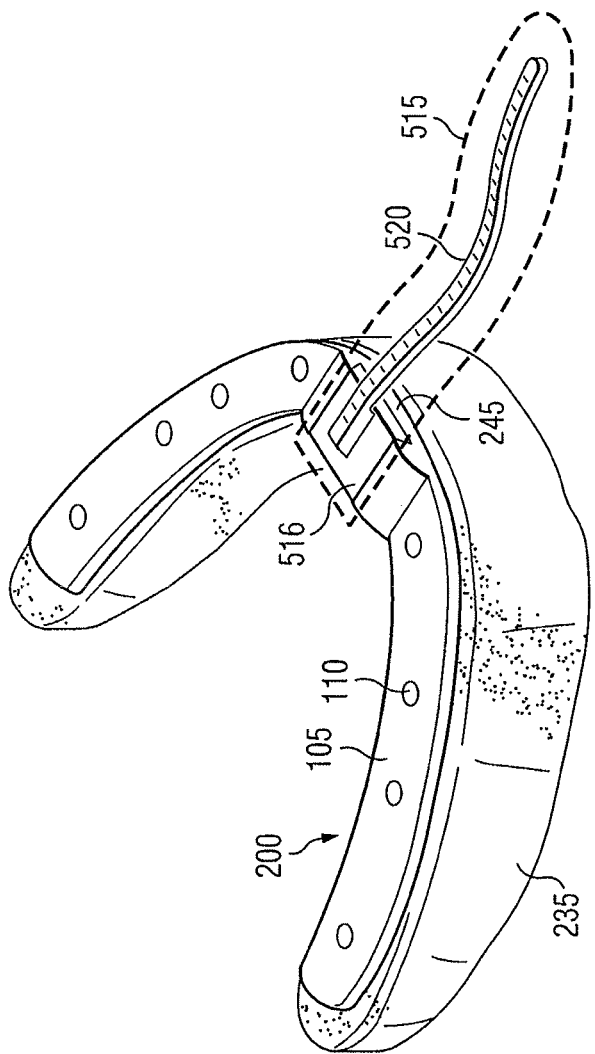
FIG. 30 illustrates an example arch comprising a tension element.

FIG. 30 illustrates an example arch comprising a second anchoring element and a tension element. As shown in FIG. 30, an arch is provided that comprises an arched frame 200 and a moldable tray 235 coupled to arched frame 200. Arched frame 200 comprises an arched body 205 that defines a plurality of apertures 210. The arch may further comprise a second anchoring element 245. In particular embodiments, second anchoring element 245 may be coupled to the arch along the midline of the arch. The arch may further comprise a tension element 515. In particular embodiments, tension element 515 may be flexible and may be configured to engage second anchoring element 245. In particular embodiments, tension element 515 may be further configured to couple to an anchoring element outside a user's mouth when the arch is inserted in the user's mouth. In some embodiments, tension element 515 may comprise a strap 520 and a coupler 516. Coupler 516 may be configured to engage the second anchoring element. In particular embodiments, coupler 516 may be configured to removably engage the second anchoring element. Strap 520 may be coupled to coupler 516. In particular embodiments, strap 520 may be configured to engage the anchoring element outside the user's mouth when the arch is inserted in the user's mouth. In particular embodiments, strap 520 may comprise a hard plastic, leather, or metal. In certain embodiments, strap 520 may be a zip tie. In other embodiments, strap 520 may be a wire, belt, string, or any other appropriate element to engage the anchoring element. Although this disclosure describes an arch comprising arched frame 200, moldable tray 235, and tension element 515, this disclosure contemplates a one-piece arch comprising tension element 515.

Figure 31:
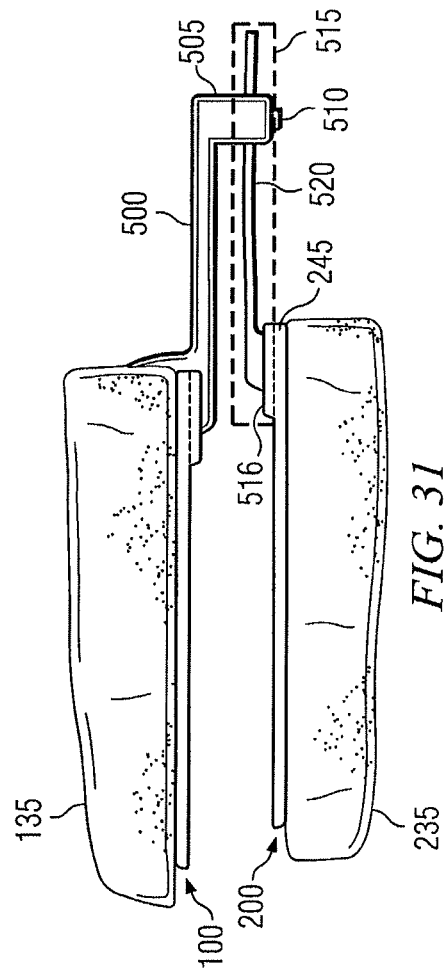
FIG. 31 illustrates an example dental device comprising a dental attachment and a tension element.

FIG. 31 illustrates an example dental device comprising a dental attachment, a second anchoring element, and a tension element. As shown in FIG. 31, a dental device is provided that comprises an arched frame 100 and a second arched frame 200. The dental device further comprises a moldable tray 135 coupled to arched frame 100 and a second moldable tray 235 coupled to second arched frame 200. The dental device may further comprise a dental attachment configured to engage arched frame 100. In particular embodiments, the dental attachment may comprise a post 500 and an anchoring element 505. The dental device may further comprise a second anchoring element 245. Second anchoring element 245 may be coupled to second arched frame 200. The dental device may further comprise a tension element 515. Tension element 515 may be configured to engage second anchoring element 245. In particular embodiments, tension element 515 may comprise a coupler 516 and a strap 520. In particular embodiments, strap 520 may be configured to engage anchoring element 505 outside the user's mouth when the dental device is inserted in the user's mouth. Anchoring element 505 may be configured to secure substantially the length of strap 520 engaged to anchoring element 505. In particular embodiments, increasing the length of strap 520 engaged to anchoring element 505 will adjust the forward position of arched frame 100 relative to second arched frame 200. In particular embodiments, the dental attachment may further comprise a release mechanism 510.

Figure 32:
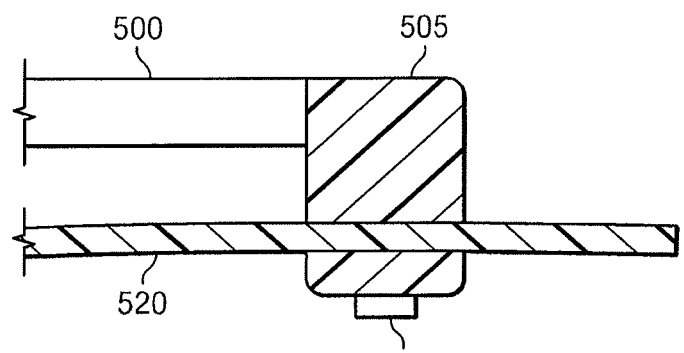
FIG. 32 illustrates an example dental attachment and tension element.

FIG. 32 illustrates an example dental attachment and tension element. As shown in FIG. 32, a dental attachment is provided comprising a post 500 and an anchoring element 505. Anchoring element 505 may be coupled to an end of post 500. A tension element is also provided comprising a strap 520. Strap 520 may be configured to engage anchoring element 505. Anchoring element 505 may be configured to secure the length of strap 520 engaged to anchoring element 505. In particular embodiments, the dental attachment may comprise a release mechanism 510. Release mechanism 510 may be configured to release strap 520 from anchoring element 505.

Figure 33:
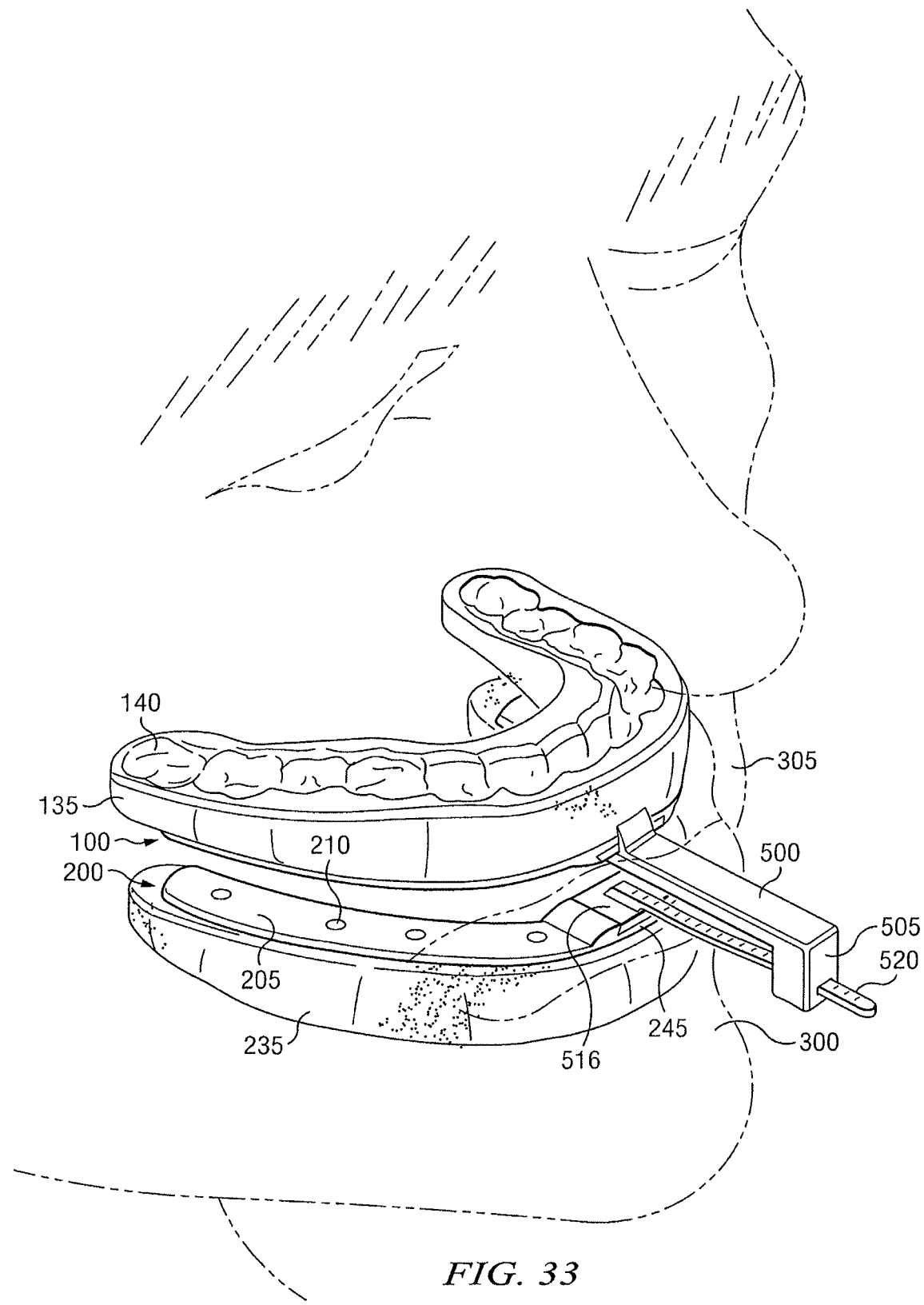
FIG. 33 illustrates an example dental device in a user's mouth.

FIG. 33 illustrates an example dental device in a user's mouth. As shown in FIG. 33, a dental device is provided that comprises an arched frame 100, a second arched frame 200, a moldable tray 135 coupled to arched frame 100, and a second moldable tray 235 coupled to second arched frame 200. Moldable tray 135 may comprise a channel 140 configured to engage at least some of the teeth of the user's maxillary arch 305. Second arched frame may comprise a second arched body 205 that defines a second plurality of apertures 210. The dental device may further comprise a dental attachment. The dental attachment may comprise a post 500 and an anchoring element 505. Anchoring element 505 may be coupled to an end of post 500, and a second end of post 500 may be configured to engage arched frame 100. Anchoring element 505 may be configured to be outside the user's mouth when the dental device is inserted in the user's mouth. The dental device may further comprise a second anchoring element 245 coupled to second arched frame 200. The dental device may further comprise a tension element comprising a coupler 516 and a strap 520. Coupler 516 may be configured to engage second anchoring element 245. Strap 520 may be coupled to coupler 516 and may be configured to engage anchoring element 520 outside the user's mouth when the dental device is inserted in the user's mouth. Anchoring element 505 may be configured to secure substantially the length of strap 520 engaged to anchoring element 505. In particular embodiments, increasing the length of strap 520 engaged to anchoring element 505 may adjust the forward position of arched frame 100 relative to second arched frame 200. In particular embodiments, adjusting the forward position of arched frame 100 relative to second arched frame 200 may adjust the forward position of the user's maxillary arch 305 relative to the user's mandibular arch 300. In particular embodiments, adjusting the forward position of the user's maxillary arch 305 relative to the position of the user's mandibular arch 300 may help to improve the user's breathing and/or prevent the user from snoring.

In particular embodiments, the dental device comprising a dental attachment and a tension element may allow a third party faster access to a user's mouth and airway. For example, if the user is a patient sleeping in a sleep laboratory, a doctor in the laboratory may quickly pull on the tension element to open an airway that closed while the patient slept. As another example, if the user is a patient undergoing surgery in a hospital, a surgeon may quickly release the tension element to open the patient's mouth for intubation or for insertion of an instrument while the patient is sedated. In particular embodiments, the dental device comprising a dental attachment and a tension element may pull the user's lower jaw forward without locking the lower jaw in place. The user's lower jaw will maintain a certain range of lateral motion while the dental device is inserted in the user's mouth. This disclosure contemplates the dental device comprising a dental attachment and a tension element being created from a kit. A patient, doctor, or surgeon may purchase the kit and create the dental device quickly. In particular embodiments, the dental device may be a disposable device that may be thrown out after one or more uses.

Figure 34:
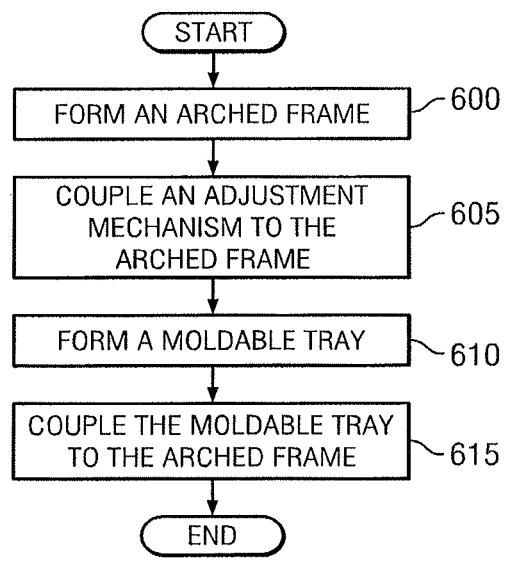
FIG. 34 illustrates an example process for creating a dental device.

FIG. 34 illustrates an example process for creating a dental device. At step 600, an arched frame is formed. In particular embodiments, the arched frame may be configured to be positioned proximate to the occlusal surface of a user's dental arch such that the arched frame extends beyond the cuspids of the user's dental arch. The arched frame may define a plurality of apertures. At step 605, an adjustment mechanism is coupled to the arched frame. In particular embodiments, the adjustment mechanism may comprise a hook and a threaded adjustor. At step 610, a moldable tray is formed. In particular embodiments, the moldable tray may comprise a channel configured to engage at least some of the teeth of the user's dental arch. In some embodiments, the channel may be shaped to conform to the teeth of a generic user's dental arch. In other embodiments, the channel may be a smooth channel configured to cover some of the teeth of the user's dental arch. In particular embodiments, the channel may be further shaped to conform to a particular user's dental arch. At step 615, the moldable tray is coupled to the arched frame. In particular embodiments, the moldable tray may engage the plurality of apertures. In particular embodiments the process may be repeated to form a second arched frame and a second moldable tray. In particular embodiments, the arched frame may comprise kevlar polycarbon, acrylic, polycarbonate resin thermoplastic, or any other suitable hard plastic polymer. In particular embodiments, the moldable tray may comprise polycaprolactone.

In particular embodiments, the process illustrated in FIG. 34 may lead to faster creation and production of dental devices. Users may avoid sending dental impressions to a laboratory to create a dental devices thus saving time and money.

Although example steps are illustrated and described, the present invention contemplates two or more steps taking place substantially simultaneously or in a different order. For example, step 605, coupling an adjustment mechanism to the arched frame, may be performed after step 610, forming a moldable tray. In addition, the present invention contemplates using methods with additional steps, fewer steps, or different steps, so long as the steps remain appropriate for creating a dental device.

Various embodiments disclosed herein may be used together in a variety of combinations. For example, in certain embodiments, the various posts, such as posts 802 and 882, may be coupled to any of the various oral appliances disclosed herein, including the oral appliances disclosed in U.S. Pat. No. 7,748,386. As another example, the various posts described herein may be coupled to any of the various masks disclosed, such as but not limited to masks 850, 890, 892, and 894. As another example, in certain embodiments, the various adjustment mechanisms may be used with the various oral appliances disclosed herein, including the adjustment mechanisms and oral appliances disclosed in U.S. Pat. No. 7,748,386. As another example, in certain embodiments the various oral appliances may be coupled with the various dental attachments disclosed herein.

Although the present invention has been described above in connection with several embodiments, changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. An oral appliance comprising:
a lower frame configured to be positioned within a user's mouth, the lower frame comprising:
  a left occlusal portion configured to be positioned proximate at least one of a left bicuspid or a left molar of a mandibular arch of the user but not proximate an incisor of the mandibular arch of the user;
  a right occlusal portion configured to be positioned proximate at least one of a right bicuspid or a right molar of the mandibular arch of the user, wherein the left and right occlusal portions define an open space between the left occlusal portion and the right occlusal portion, the space configured to be positioned above the incisor of the mandibular arch of the user when the lower frame is positioned within the user's mouth; and
  a flange coupled to the left occlusal portion and the right occlusal portion, the flange extending substantially perpendicular and mesial to the left and right occlusal portions;
a thermoplastic moldable tray coupled to the left occlusal portion, the right occlusal portion, and the flange such that the thermoplastic moldable tray extends beyond the flange in an inferior direction, the thermoplastic moldable tray comprising irradiated, cross-linked thermoplastic polymer not customized to any user's teeth, wherein the irradiated, cross-linked thermoplastic polymer softens to be moldable to a shape of a portion of the user's dental arch when the thermoplastic polymer is heated to 40 to 80 degrees Celsius; and
an adjustment mechanism coupled to the lower frame, the adjustment mechanism configured to adjust a forward position of the lower frame relative to an upper frame configured to be positioned proximate a maxillary arch of the user.

2. The oral appliance of claim 1, wherein the thermoplastic moldable tray comprises polycaprolactone.

3. The oral appliance of claim 1, wherein the lower frame comprises polycarbonate.

4. The oral appliance of claim 1, wherein the space is configured to be positioned superior to one or more incisors of the mandibular arch.

5. The oral appliance of claim 1, the upper frame comprises:
an upper left occlusal portion configured to be positioned proximate at least one of a left bicuspid or a left molar of the maxillary arch of the user; and
an upper right occlusal portion configured to be positioned proximate at least one of a right bicuspid or a right molar of the maxillary arch of the user.

6. The oral appliance of claim 1, wherein the lower frame comprises:
a left flange portion coupled to the left occlusal portion such that the left flange portion is substantially perpendicular to the left occlusal portion and buccal to the thermoplastic moldable tray; and
a right flange portion coupled to the right occlusal portion such that the right flange portion is substantially perpendicular to the right occlusal portion and buccal to the thermoplastic moldable tray.

7. The oral appliance of claim 1, wherein the thermoplastic moldable tray extends beyond a posterior edge of the left occlusal portion in a posterior direction and a posterior edge of the right occlusal portion in a posterior direction.

8. The oral appliance of claim 1, wherein:
the left occlusal portion defines an aperture through which the thermoplastic moldable tray couples to the left occlusal portion; and
the right occlusal portion defines an aperture through which the thermoplastic moldable tray couples to the right occlusal portion.

9. The oral appliance of claim 1, wherein:
the thermoplastic moldable tray is customizable to the user's teeth when heated to at least sixty degrees Celsius; and
the lower frame substantially maintains its shape when heated to one hundred degrees Celsius.

10. An oral appliance comprising:
a lower frame configured to be positioned within a user's mouth, the lower frame comprising:
  a left occlusal portion configured to be positioned proximate at least one of a left bicuspid or a left molar of a mandibular arch of the user but not proximate an incisor of the mandibular arch of the user; and
  a right occlusal portion configured to be positioned proximate at least one of a right bicuspid or a right molar of the mandibular arch of the user, wherein the left and right occlusal portions define an open space between the left occlusal portion and the right occlusal portion, the space configured to be positioned above the incisor of the mandibular arch of the user when the lower frame is positioned in the user's mouth;
a thermoplastic moldable tray coupled to the left occlusal portion and the right occlusal portion such that the thermoplastic moldable tray extends beyond a lingual edge of the left occlusal portion in a lingual direction and beyond a lingual edge of the right occlusal portion in a lingual direction, the thermoplastic moldable tray comprising irradiated, cross-linked thermoplastic polymer not customized to any user's teeth, wherein the irradiated, cross-linked thermoplastic polymer softens to be moldable to a shape of a portion of the user's dental arch when the thermoplastic polymer is heated to 40 to 80 degrees Celsius; and
an adjustment mechanism coupled to the lower frame, the adjustment mechanism configured to adjust a forward position of the lower frame relative to an upper frame configured to be positioned proximate a maxillary arch of the user.

11. The oral appliance of claim 10, wherein:
the lower frame further comprises a flange coupled to the right occlusal portion and the left occlusal portion, the flange extending substantially perpendicular to the left and right occlusal portions and extending mesial to the left and right occlusal portions; and
the thermoplastic moldable tray is further coupled to the flange such that the thermoplastic moldable tray extends beyond the flange in an inferior direction.

12. The oral appliance of claim 10, wherein the thermoplastic moldable tray comprises polycaprolactone.

13. The oral appliance of claim 10, wherein the lower frame comprises polycarbonate.

14. The oral appliance of claim 10, wherein the thermoplastic moldable tray is configured to extend beyond the flange in the inferior direction proximate an incisor of the mandibular arch of the user.

15. The oral appliance of claim 10, wherein:
the thermoplastic moldable tray is customizable to the user's teeth when heated to at least sixty degrees Celsius; and
the lower frame substantially maintains its shape when heated to one hundred degrees Celsius.

16. An oral appliance comprising:
a lower frame configured to be positioned within a user's mouth, the lower frame comprising:
  a left occlusal portion configured to be positioned proximate at least one of a left bicuspid or a left molar of a mandibular arch of the user but not proximate an incisor of the mandibular arch of the user;
  a right occlusal portion configured to be positioned proximate at least one of a right bicuspid or a right molar of the mandibular arch of the user, the left and right occlusal portions define an open space between the left occlusal portion and the right occlusal portion, the space configured to be positioned above the incisor when the lower frame is positioned within the user's mouth; and
  a flange coupled to the left and right occlusal portions, the flange extending substantially perpendicular and mesial to the left and right occlusal portions;
a thermoplastic moldable tray coupled to the left occlusal portion, the right occlusal portion, and the flange such that the thermoplastic moldable tray extends beyond the flange in an inferior direction and beyond a lingual edge of the left occlusal portion in a lingual direction and beyond a lingual edge of the right occlusal portion in a lingual direction, the thermoplastic moldable tray comprising irradiated, cross-linked thermoplastic polymer not customized to any user's teeth, wherein the irradiated, cross-linked thermoplastic polymer softens to be moldable to a shape of a portion of the user's dental arch when the thermoplastic polymer is heated to 40 to 80 degrees Celsius; and
an adjustment mechanism coupled to the lower frame, the adjustment mechanism configured to adjust a forward position of the lower frame relative to an upper frame configured to be positioned proximate a maxillary arch of the user.

17. The oral appliance of claim 16, wherein the lower frame comprises polycarbonate.

18. The oral appliance of claim 16, wherein the thermoplastic moldable tray extends beyond a posterior edge of the left occlusal portion in a posterior direction and a posterior edge of the right occlusal portion in a posterior direction.

19. An oral appliance comprising:
a lower frame configured to be positioned within a user's mouth, the lower frame comprising:
  a left occlusal portion configured to be positioned proximate at least one of a left bicuspid or a left molar of a mandibular arch of the user but not proximate an incisor of the mandibular arch of the user;
  a right occlusal portion configured to be positioned proximate at least one of a right bicuspid or a right molar of the mandibular arch of the user, wherein the left and right occlusal portions define an open space between the left occlusal portion and the right occlusal portion, the space configured to be positioned above the incisor of the mandibular arch of the user when the lower frame is positioned within the user's mouth;
  a mesial flange portion coupled to the left and right occlusal portions, the mesial flange extending substantially perpendicular and mesial to the left and right occlusal portions;
  a left flange portion coupled to the left occlusal portion such that the left flange portion is substantially perpendicular to the left occlusal portion and buccal to the thermoplastic moldable tray, the left flange portion and the mesial flange portion define a left space along the left occlusal portion that separates the left flange portion from the mesial flange portion; and
  a right flange portion coupled to the right occlusal portion such that the right flange portion is substantially perpendicular to the right occlusal portion and buccal to the thermoplastic moldable tray, the right flange portion and the mesial flange portion define a right space along the right occlusal portion that separates the right flange portion from the mesial flange portion;
a thermoplastic moldable tray coupled to the left occlusal portion, the right occlusal portion, and the mesial flange portion such that the thermoplastic moldable tray extends beyond the mesial flange portion in an inferior direction, the thermoplastic moldable tray comprising irradiated, cross-linked thermoplastic polymer not customized to any user's teeth, wherein the irradiated, cross-linked thermoplastic polymer softens to be moldable to a shape of a portion of the user's dental arch when the thermoplastic polymer is heated to 40 to 80 degrees Celsius; and
an adjustment mechanism coupled to the lower frame, the adjustment mechanism configured to adjust a forward position of the lower frame relative to an upper frame configured to be positioned proximate a maxillary arch of the user.

20. The oral appliance of claim 19, wherein the thermoplastic moldable tray comprises polycaprolactone.

21. The oral appliance of claim 19, wherein the lower frame comprises polycarbonate.

22. The oral appliance of claim 19, wherein the space is configured to be positioned superior to one or more incisors of the mandibular arch.

23. The oral appliance of claim 19, the upper frame comprises:
an upper left occlusal portion configured to be positioned proximate at least one of a left bicuspid or a left molar of the maxillary arch of the user; and
an upper right occlusal portion configured to be positioned proximate at least one of a right bicuspid or a right molar of the maxillary arch of the user.

24. The oral appliance of claim 19, wherein the thermoplastic moldable tray extends beyond a posterior edge of the left occlusal portion in a posterior direction and a posterior edge of the right occlusal portion in a posterior direction.

25. The oral appliance of claim 19, wherein:
the left occlusal portion defines an aperture through which the thermoplastic moldable tray couples to the left occlusal portion; and the right occlusal portion defines an aperture through which the thermoplastic moldable tray couples to the right occlusal portion.

26. The oral appliance of claim 19, wherein:

the thermoplastic moldable tray is customizable to the user's teeth when heated to at least sixty degrees Celsius; and the lower frame substantially maintains its shape when heated to one hundred degrees Celsius.

* * * * *